(12) United States Patent
Blobel et al.

(10) Patent No.: US 10,329,333 B2
(45) Date of Patent: Jun. 25, 2019

(54) CONTROLLED GENE EXPRESSION METHODS

(71) Applicant: The Children's Hospital of Philadelphia, Philadelphia, PA (US)

(72) Inventors: Gerd Blobel, Bala Cynwyd, PA (US); Wulan Deng, Berkeley, CA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 15/785,529

(22) Filed: Oct. 17, 2017

(65) Prior Publication Data

US 2018/0051059 A1 Feb. 22, 2018

Related U.S. Application Data

(62) Division of application No. 14/405,932, filed as application No. PCT/US2013/030650 on Mar. 13, 2013, now Pat. No. 9,815,877.

(60) Provisional application No. 61/656,961, filed on Jun. 7, 2012.

(51) Int. Cl.
*A61K 48/00* (2006.01)
*C07K 14/47* (2006.01)
*C12N 15/63* (2006.01)

(52) U.S. Cl.
CPC .......... *C07K 14/4702* (2013.01); *A61K 48/00* (2013.01); *C07K 14/47* (2013.01); *C12N 15/63* (2013.01); *C07K 2319/81* (2013.01)

(58) Field of Classification Search
CPC .... A61K 48/00; C07K 14/47; C07K 14/4702; C07K 2319/81; C12N 15/63
USPC ...................... 435/320.1, 325, 375
See application file for complete search history.

(56) References Cited

U.S. PATENT DOCUMENTS

| | | | |
|---|---|---|---|
| 6,933,113 B2 | 8/2005 | Case et al. | |
| 8,034,768 B2 | 10/2011 | Ahn et al. | |
| 8,071,370 B2 | 12/2011 | Wolffe et al. | |
| 2005/0048528 A1 | 3/2005 | Visvader et al. | |
| 2007/0105114 A1 | 5/2007 | Li et al. | |
| 2008/0220484 A1 | 9/2008 | Breuer et al. | |
| 2011/0016540 A1 | 1/2011 | Weinstein et al. | |

FOREIGN PATENT DOCUMENTS

| | | |
|---|---|---|
| WO | 2004/099402 A1 | 11/2004 |
| WO | 2005/047315 A1 | 5/2005 |
| WO | 2005039613 | 6/2005 |
| WO | 2007121326 | 10/2007 |

OTHER PUBLICATIONS

Matthews et al. 2003. EMBO Reports. 4:1132-1137 (Year: 2003).*
Deng et al. (2010. Blood (ASH Annual meeting abstracts, 116, Abstract 647). (Year: 2010).*
Carter et al., Long-range chromatin regulatory interactions in vivo, Nat. Genet., 2002, 32, 623-626.
Tripic et al., SCL and associated proteins distinguish active from repressive GATA transcription factor complexes, Blood, 2009, 113, 2191-2201.
Song et al., Multiple functions of Ldb1 required for beta-globin activation during erythroid differentiation, Blood, 2010, 116, 2356-64.
Xu et al., Identification of a TAL1 target gene reveals a positive role for the LIM domain-binding protein Ldb1 in erythroid gene expression and differentiation, Mol. Cell. Biol., 2003, 23, 7585-7599.
Dean et al., In the loop: long range chromatin interactions and gene regulation, Brief Funct. Genomics, 2011, 10, 3-10.
Kadauke et al., Chromatin loops in gene regulation, Biochim. Biophys. Acta, 2009, 1789:17-25.
Miele et al., Long-range chromosomal interactions and gene regulation, Mol. Biosyst., 2008, 4, 1046-1057.
Schoenfelder et al., The transcriptional interactome: gene expression in 3D, Curr. Opin. Genet. Dev., 2010, 20, 127-133.
Sexton et al., Genomic interactions: chromatin loops and gene meeting points in transcriptional regulation, Semin. Cell Dev. Biol., 2009, 20, 849-855.
Palstra et al., The beta-globin nuclear compartment in development and erythroid differentiation, Nat. Genet., 2003, 35,190-194.
Spilianakis et al., Long-range intrachromosomal interactions in the T helper type 2 cytokine locus, Nat. Immunol., 2004, 5,1017-1027.
Vernimmen et al., Long-range chromosomal interactions regulate the timing of the transition between poised and active gene expression, EMBO J., 2007, 26, 2041-2051.
Matthews et al., LIM—domain-binding protein 1:a multifunctional cofactor that interacts with diverse proteins, EMBO Rep., 2003, 4, 1132-1137.
Morcillo et al., Chip, a widely expressed chromosomal protein required for segmentation and activity of a remote wing margin enhancer in *Drosophila*, Genes Dev., 1997, 11, 2729-2740.
Thaler et al., LIM factor Lhx3 contributes to the specification of motor neuron and interneuron identity through cell-type-specific protein-protein interactions, Cell, 2002, 110, 237-249.
Bartsevich et al., Engineered zinc finger proteins for controlling stem cell fate, Stem Cells, 2003, 21, 632-637.
Tolhuis et al., Looping and interaction between hypersensitive sites in the active beta-globin locus, Mol. Cell. 2002, 10, 1453-65.
Jurata et al., Functional analysis of the nuclear LIM domain interactor NLI, Mol. Cell Biol., 1997, 17, 5688-98.
Deng et al., Manipulating higher order chromatin structure of the beta-globin locus by targeted tethering of a "looping" factor, Blood (ASH Annual Meeting Abstracts), 2010, 116, Abstract 647.
Lamonica et al., Bromodomain protein Brd3 associates with acetylated GATA1 to promote its chromatin occupancy at erythroid target genes, PNAS, 2011, 108, 22, e159-e168.
Deng et al., Do chromatin loops provide epigenetic gene expression states, Curr Opin Genet Dev, 2010, 20, 5, 548-554.
Deng et al., Controlling long-range genomic interactions at a native locus by targeted tethering of a looping factor, Cell, 2012, 149, 1233-1244.
Cross et al. LIM domain binding proteins 1 and 2 have different oligomeric states, J. Mole Biol., 2010, 399, 133-144.

(Continued)

*Primary Examiner* — Janet L Epps-Smith
(74) *Attorney, Agent, or Firm* — Robert C. Netter, Jr.; Dann, Dorfman, Herrell & Skillman

(57) ABSTRACT

Methods and compositions for controlling gene expression are disclosed.

Figure 1A:
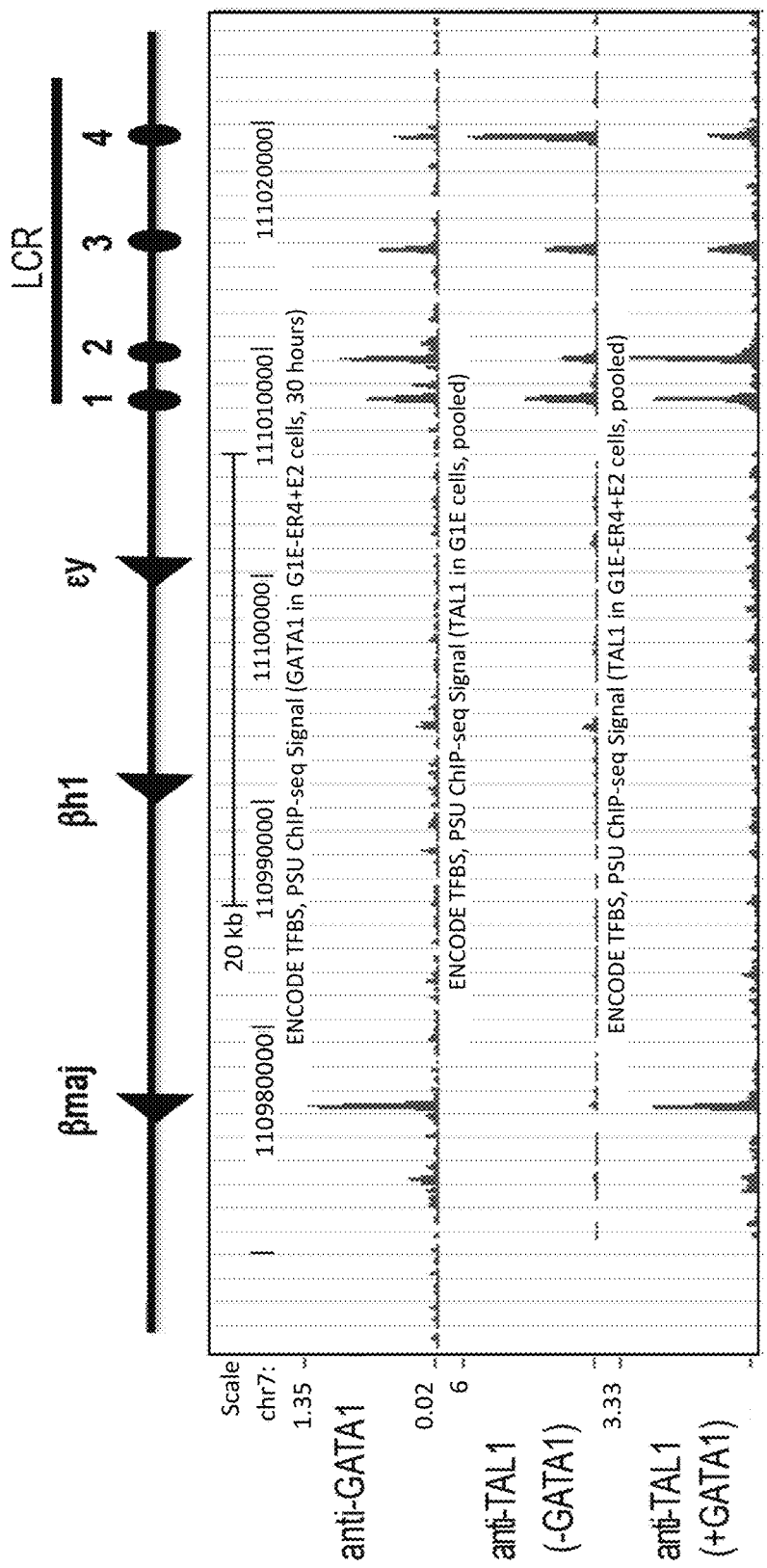

12 Claims, 28 Drawing Sheets
Specification includes a Sequence Listing.

(56) References Cited

OTHER PUBLICATIONS

Deane, J.E., et al., "Tandem LIM Domains Provide Synergistic Binding in the LMO4:Ldb1 Complex" EMBO J. (2004) 23:3589-3598.
Parchaliuk, D.L., et al. "Yeast Two-hybrid System: Part A: Screen Preparation" Tech. Tips Online (1999) 4:6-15.
Deng, W., et al., Abstract 1447/B863:"Manipulating Higher Order Chromatin Structure of an Endogenous Gene Locus by Targeted Tethering of a "Looping" Factor" Mol. Biol. Cell (2010) 21(24):4299 at p. 1109-1110.
Sadelain et al., Globin gene transfer for treatment of the beta-thalassemias and sickle cell disease, Best Pract Res Clin Haematol., 2004, 17, 517-534.
Weatherall et al., Phenotype-genotype relationships in monogenic disease: lessons from the thalassaemias, Nat Rev Genet., 2001, 2, 245-255.
Deng et al., Reactivation of Developmentally Silenced Globin Genes by Forced Chromatin Looping, Cell, 2014, 158, 849-860.
Klug et al., The discovery of zinc fingers and their applications in gene regulation and genome manipulation, Annu Rev Biochem., 2010, 79, 213-231.
Sawado et al., The β-globin locus control region (LCR) functions primarily by enhancing the transition from transcription initiation to elongation, Genes Dev., 2003, 17, 1009-1018.
Jing et al., Exchange of GATA factors mediates transitions in looped chromatin organization at a developmentally regulated gene locus, Mol Cell., 2008, 29, 232-242.

\* cited by examiner

1 MLDRDVGPTP MYPPTYLEPG IGRHTPYGNQ TDYRIFELNK RLQNWTEECD NLWWDAFTTE

61 FFEDDAMLTI TFCLEDGPKR YTIGRTLIPR YFRSIFEGGA TELYYVLKHP KEAFHSNFVS

121 LDCDQGSMVT QHGKPMFTQV CVEGRLYLEF MFDDMMRIKT WHFSIRQHRE LIPRSILAMH

181 AQDPQMLDQL SKNITRCGLS NSTLNYLRLC VILEPMQELM SRHKTYSLSP RDCLKTCLFQ

241 KWQRMVAPPA EPTRQQPSKR RKRKMSGGST MSSGGGNTNN SNSKKKSPAS TFALSSQVPD

301 VMVVGEPTLM GGEFGDEDER LITRLENTQF DAANGIDDED SFNNSPALGA NSPWNSKPPS

361 SQESKSENPT SQASQ

Figure 15A

1 MSVGCACPGC SSKSFKLYSP KEPPNGNAFP PFHPGTMLDR DVGPTPMYPP TYLEPGIGRH

61 TPYGNQTDYR IFELNKRLQN WTEECDNLWW DAFTTEFFED DAMLTITFCL EDGPKRYTIG

121 RTLIPRYFRS IFEGGATELY YVLKHPKEAF HSNFVSLDCD QGSMVTQHGK PMFTQVCVEG

181 RLYLEFMFDD MMRIKTWHFS IRQHRELIPR SILAMHAQDP QMLDQLSKNI TRCGLSNSTL

241 NYLRLCVILE PMQELMSRHK TYSLSPRDCL KTCLFQKWQR MVAPPAEPTR QQPSKRRKRK

301 MSGGSTMSSG GGNTNNSNSK KKSPASTFAL SSQVPDVMVV GEPTLMGGEF GDEDERLITR

361 LENTQFDAAN GIDDEDSFNN SPALGANSPW NSKPPSSQES KSENPTSQAS Q

Figure 15B

In adult erythroid cells

CONTROLLED GENE EXPRESSION METHODS

This application is a divisional application of U.S. patent application Ser. No. 14/405,932, filed Dec. 5, 2014, which is a § 371 application of PCT/US2013/030650, filed Mar. 13, 2013, which claims priority under 35 U.S.C. § 119(e) to U.S. Provisional Patent Application No. 61/656,961, filed on Jun. 7, 2012. The foregoing applications are incorporated by reference herein.

This invention was made with government support under Grant Nos. 5R37DK058044 and 2RO1DK054937 awarded by National Institutes of Health. The government has certain rights in the invention.

FIELD OF THE INVENTION

The present invention relates to the field of gene expression. More specifically, the invention provides compositions and methods for the controlling of gene expression through chromatin looping.

BACKGROUND OF THE INVENTION

Several publications and patent documents are cited throughout the specification in order to describe the state of the art to which this invention pertains. Each of these citations is incorporated herein by reference as though set forth in full.

Gene activity is controlled by a combination of proximal and distal regulatory elements that can be separated by up to hundreds of kilobases. Longstanding questions have been how these elements interact functionally to regulate gene expression, how gene specificity is achieved, and how unwanted effects on nearby irrelevant genes are avoided. The use of chromosome conformation capture (3C) and its derivatives has revealed that distant chromosomal elements can be juxtaposed to form chromatin loops, thus providing one mechanism of long-range enhancer function (Cullen et al. (1993) Science 261:203-206; Dekker et al. (2002) Science 295:1306-1311). Chromatin looping has been discovered at numerous gene loci, and reflects a widespread organizing principle of the chromatin fiber (Dean, A. (2011) Brief Funct. Genomics 10:3-10; Kadauke et al. (2009) Biochim. Biophys. Acta, 1789:17-25; Miele et al. (2008) Mol. Biosyst., 4:1046-1057; Schoenfelder et al. (2010) Curr. Opin. Genet. Dev., 20:127-133; Sexton et al. (2009) Semin. Cell Dev. Biol., 20:849-855). Although looping can occur at genes prior to their full activation, the onset of transcription is tightly associated with additional looped interactions (Palstra et al. (2003) Nat. Genet., 35:190-194; Spilianakis et al. (2004) Nat. Immunol., 5:1017-1027; Vernimmen et al. (2007) EMBO J., 26:2041-2051). However, based on studies using pharmacological inhibitors of transcription elongation, it has become clear that ongoing transcription is dispensable for sustaining preformed chromatin loops (Mitchell et al. (2008) Genes Dev., 22:20-25; Palstra et al. (2008) PLoS ONE 3:e1661). Moreover, chromatin looping is not limited to active genes. For example, upon repression of the Kit gene, loss of an enhancer-promoter loop is accompanied by de novo loop formation within the gene body (Jing et al. (2008) Mol. Cell., 29:232-242). These studies indicate that chromatin loops are highly dynamic and occur at active and repressed genes but leave open the question as to whether these long-range interactions are a cause or consequence of dynamic changes in transcription initiation.

SUMMARY OF THE INVENTION

In accordance with the present invention, compositions and methods are provided for modulating the expression of a gene of interest. Specifically, nucleic acid molecules encoding a polypeptide comprising a DNA binding domain and a looping factor are provided. The DNA binding domain and the looping factor may be linked through a covalent bond or an amino acid linker. In a particular embodiment, the DNA binding domain comprises a zinc finger polypeptide or a transcription activator-like effector polypeptide. The DNA binding domain may be designed to specifically bind a target sequence in the promoter of a gene of interest to modulate its expression. In a particular embodiment, the looping factor is LIM domain binding 1 (Ldb1) or a fragment thereof. In a particular embodiment, the fragment of Ldb1 comprises the self association domain of Ldb1 (e.g., amino acids 1 to about 200 of Ldb1). The polypeptide encoded the nucleic acid molecules are also encompassed by the instant invention. Compositions and vectors comprising at least one of the nucleic acid molecules are also provided herein.

In accordance with another aspect of the instant invention, methods of modulating the expression of a gene of interest in a cell are provided. The methods comprise expressing at least one nucleic acid molecule of the instant invention in the cell. The nucleic acid molecules may be introduced into the cell by any means (e.g., transfection or infection (e.g., via a viral vector)). The methods of the instant invention may further comprise expressing a first and second nucleic acid molecule in the cell, wherein the first and second nucleic acid molecule encode first and second polypeptides comprising a DNA binding domain and a looping factor and wherein the DNA binding domain of the first polypeptide specifically binds to a target sequence in the promoter of the gene of interest and the DNA binding domain of the second polypeptide specifically binds to a target sequence in the locus control region of the gene of interest.

In accordance with another aspect of the instant invention, methods of inhibiting, treating, and/or preventing a disease or disorder associated with aberrant protein expression are provided. In a particular embodiment, the method comprises administering at least one nucleic acid molecule of the instant invention to the subject.

BRIEF DESCRIPTIONS OF THE DRAWINGS

Figure 1B:
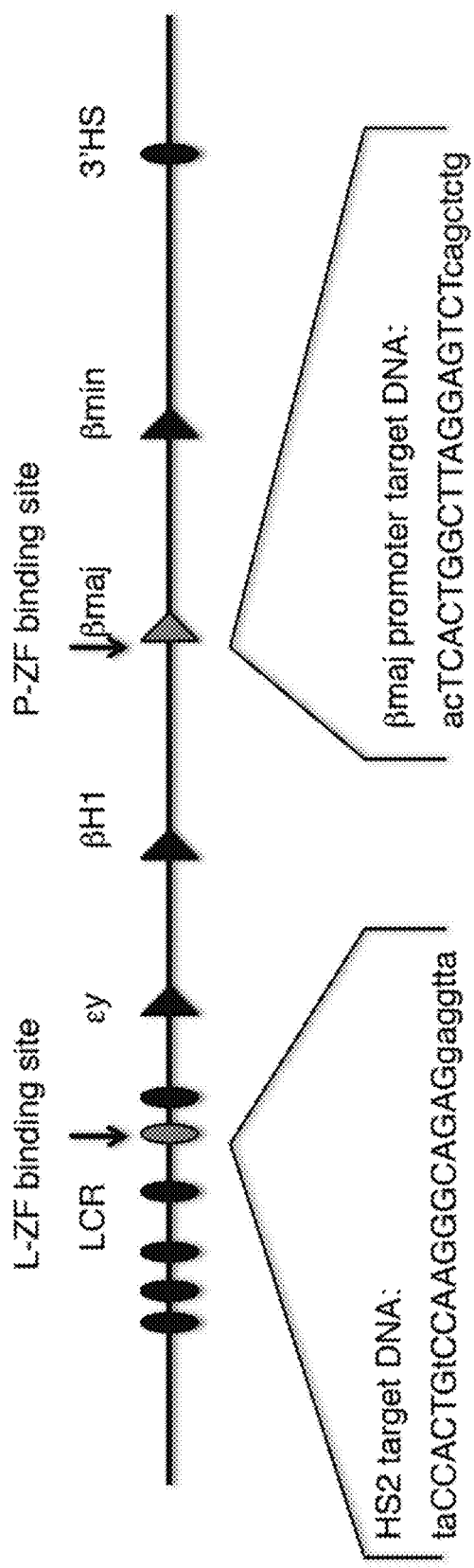

FIGS. 1A-1D show ZFs targeting of the β-globin locus. FIG. 1A shows anti-GATA1 (top) and anti-TAL1 (middle and bottom) ChIP-seq tracks encompassing the β-globin locus from parental G1E cells (middle) and G1E cells expressing induced GATA1-ER (top, bottom). TAL1 is a reliable indicator for the presence of Ldb1 since their occupancy patterns are virtually identical (Tripic et al. (2009) Blood 113:2191-2201). In the absence of GATA1, TAL1 is completely lost from the β-major globin promoter but not the LCR. FIG. 1B shows L-ZF and P-ZF target HS2 of the LCR (SEQ ID NO: 81) and the β-major promoter (SEQ ID NO: 82), respectively. The DNA sequences used for ELISA experiments are shown, including 18 nucleotides of ZF binding site (uppercase) and the flanking nucleotides (lowercase). Anti-HA ChIP profiles of HA tagged P-ZF (FIG. 1C) and L-ZF (FIG. 1D) in G1E cells were shown. N=3; error bars denote standard deviation.

Figure 2A:
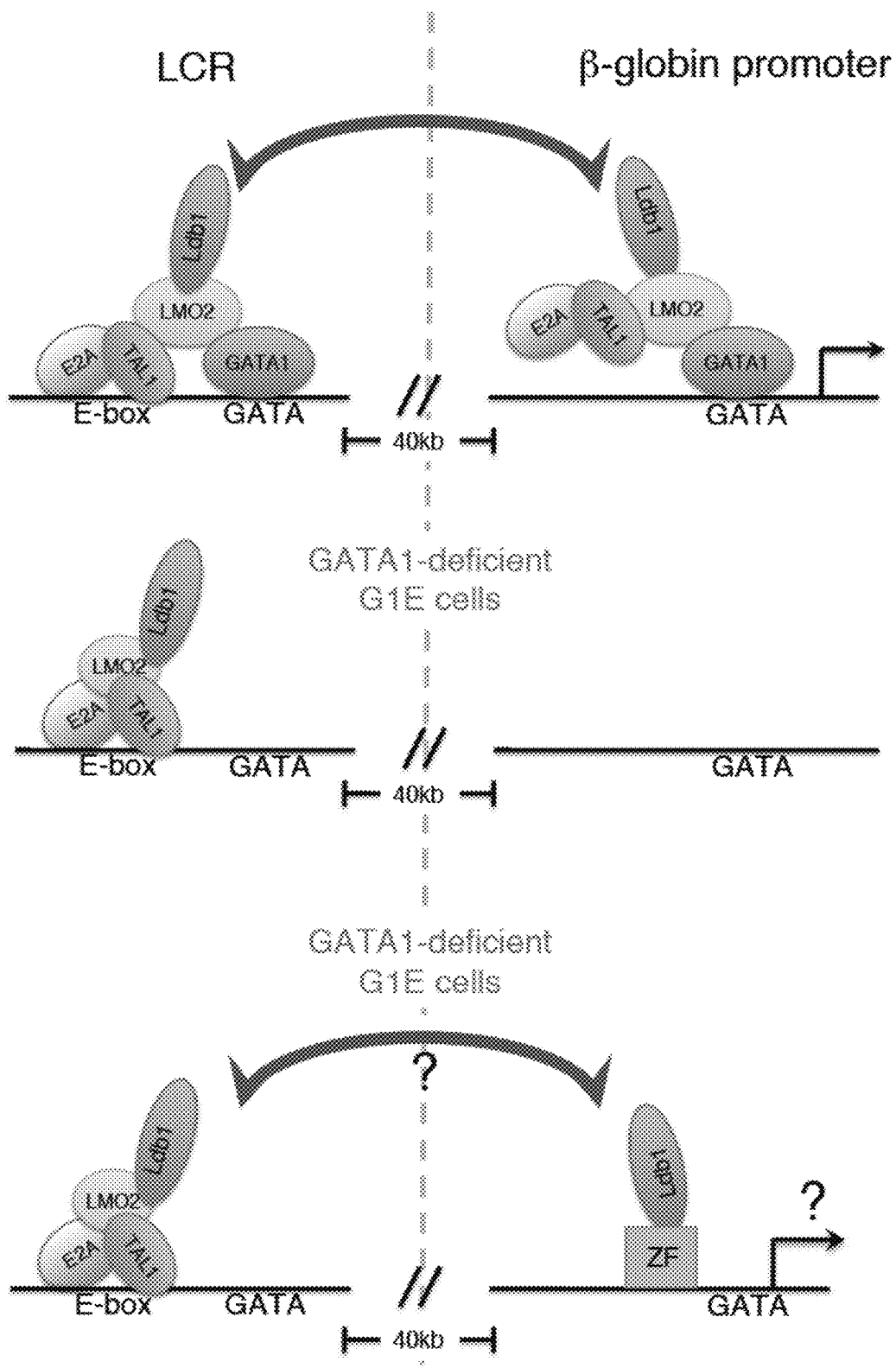
Figure 2B:
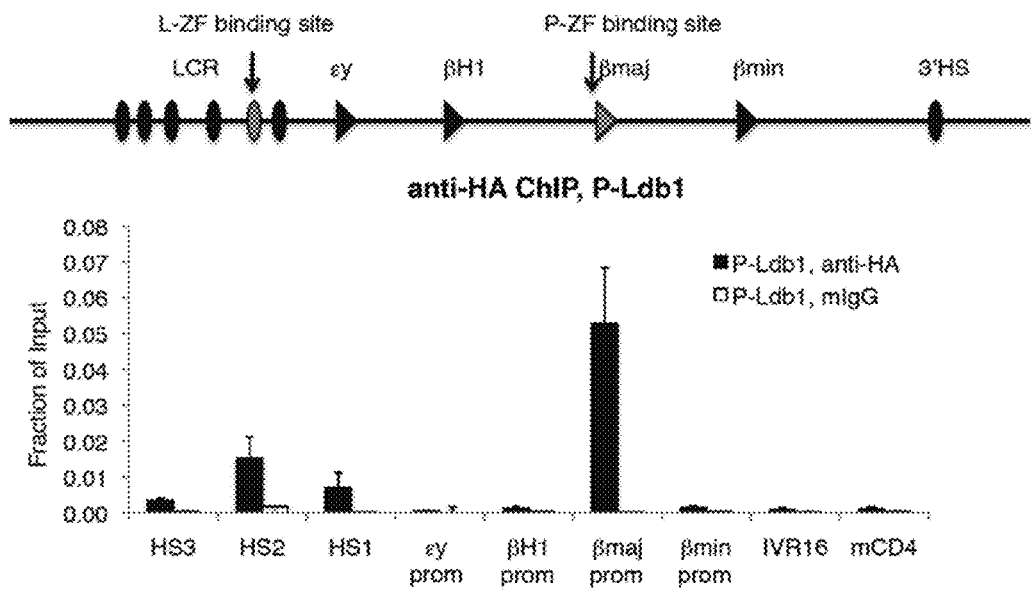
Figure 2C:
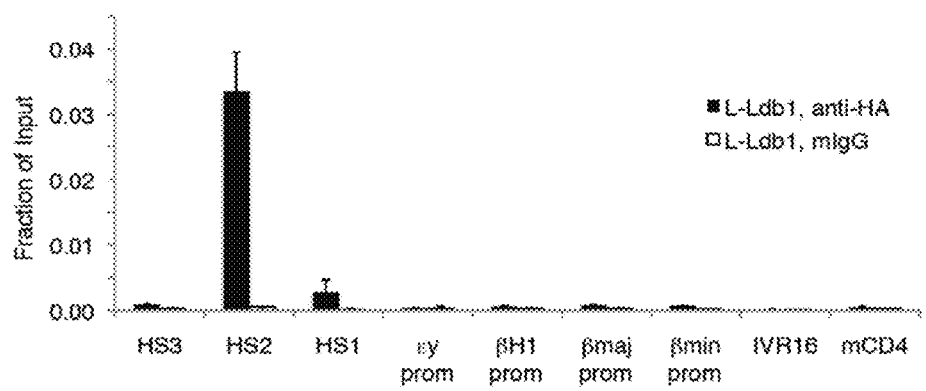
Figure 2D:
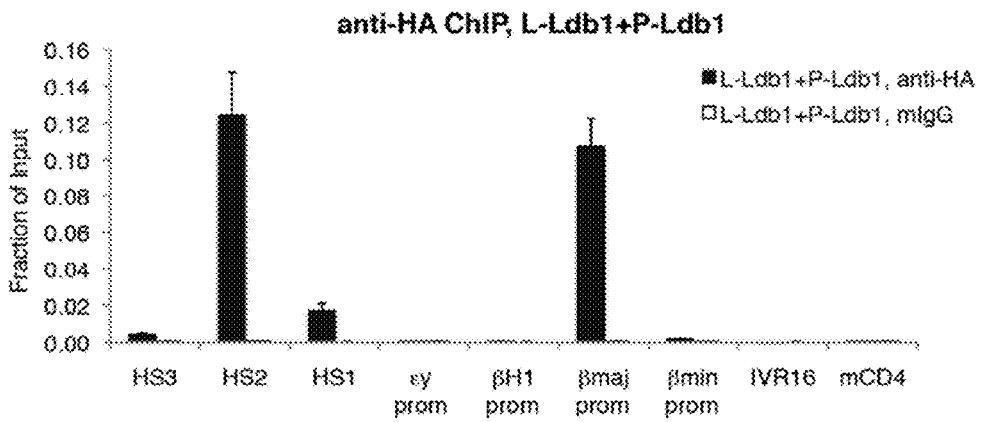

FIGS. 2A-2D show ZF-mediated targeting of Ldb1 to the β-globin locus. FIG. 2A (top) shows a schematic of the wild-type scenario in which GATA1 and the TAL1 complex recruit Ldb1 to promote chromatin looping. FIG. 2A (middle) shows that the lack of GATA1 leads to loss of Ldb1 at the promoter, impaired looping, and reduced transcriptional activation. FIG. 2A (bottom) shows ZF-mediated Ldb1 tethering to the β-globin promoter and its ability to restore looping and transcription activation. FIG. 2B shows P-ZF and L-ZF target the β-major promoter and HS2 of the LCR, respectively. FIGS. 2B-2D show anti-HA ChIP in cells expressing P-Ldb1 (FIG. 2B), L-Ldb1 (FIG. 2C), and L-Ldb1+P-Ldb1 (FIG. 2D). L-Ldb1 binds selectively to HS2 of the LCR. P-Ldb1 binds to the promoter but additionally associates with HS 1, 2, 3 of the LCR but not to other regions, including the εy, βH1, and βmin genes, an intervening region (IVR16) or an inactive gene (CD4). N≥3; error bars denote standard deviation.

Figure 3A:
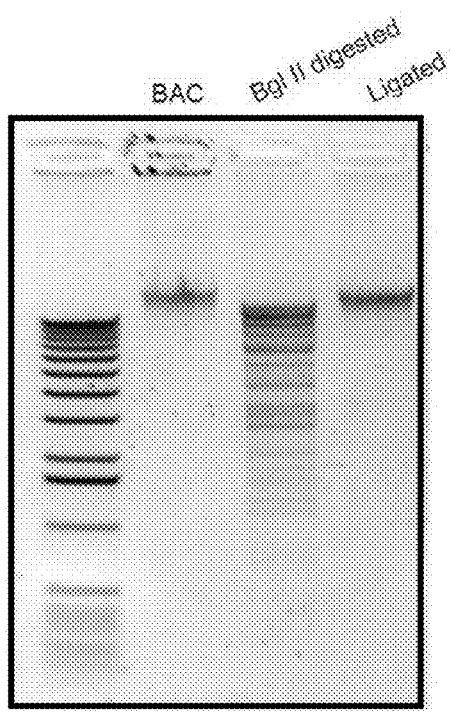
Figure 3B:
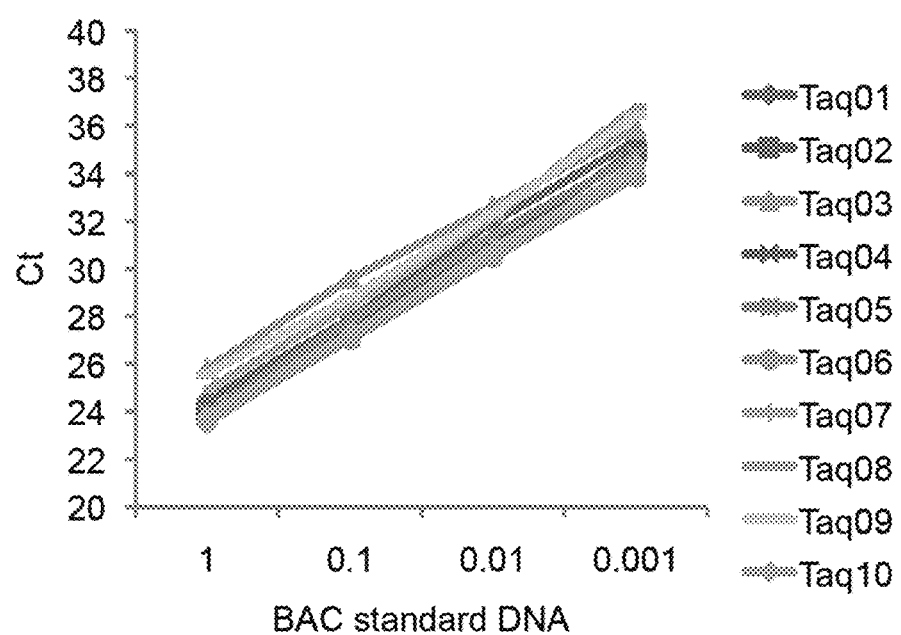
Figures 3C, 3D:
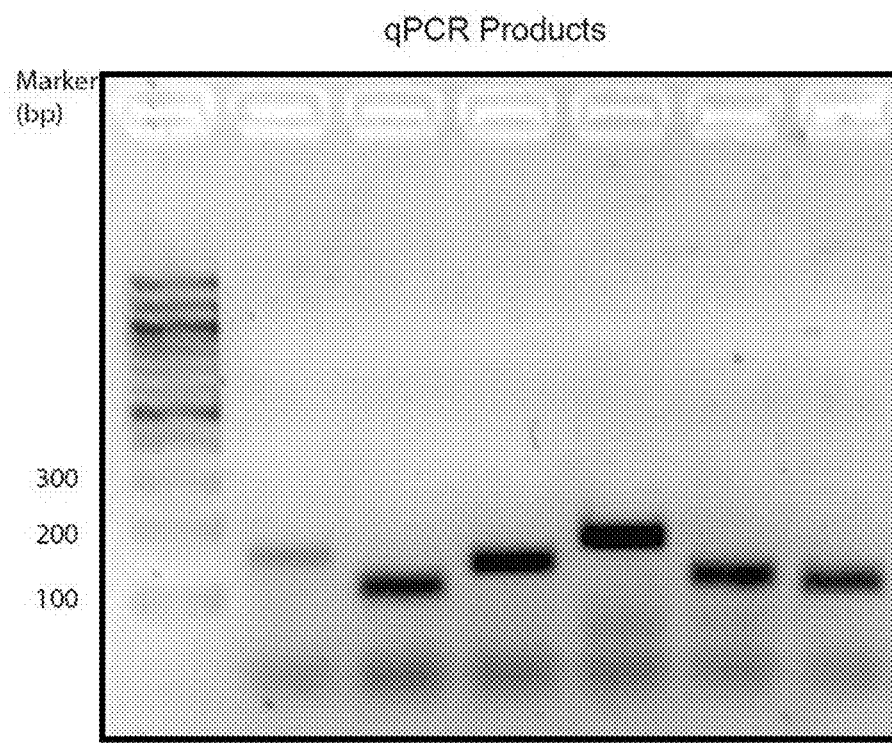

FIGS. 3A-3D show 3C quality controls. FIG. 3A provides a representative gel electrophoresis of BAC DNA. BAC DNA was purified (lane 2), digested with BglII (lane 3), and ligated with T4 ligase (lane 4) to generate random ligation products of BglII fragments that served as standard DNA for the 3C assay. FIG. 3B shows the linearity of representative 3C primers was tested using serially diluted BAC DNA as template. FIG. 3C shows the amplification products of representative 3C primers were analyzed by agarose gel electrophoresis to verify primer specificity. FIG. 3D provides the digestion efficiencies at HS2 site of a representative 3C experiment.

Figure 4A:
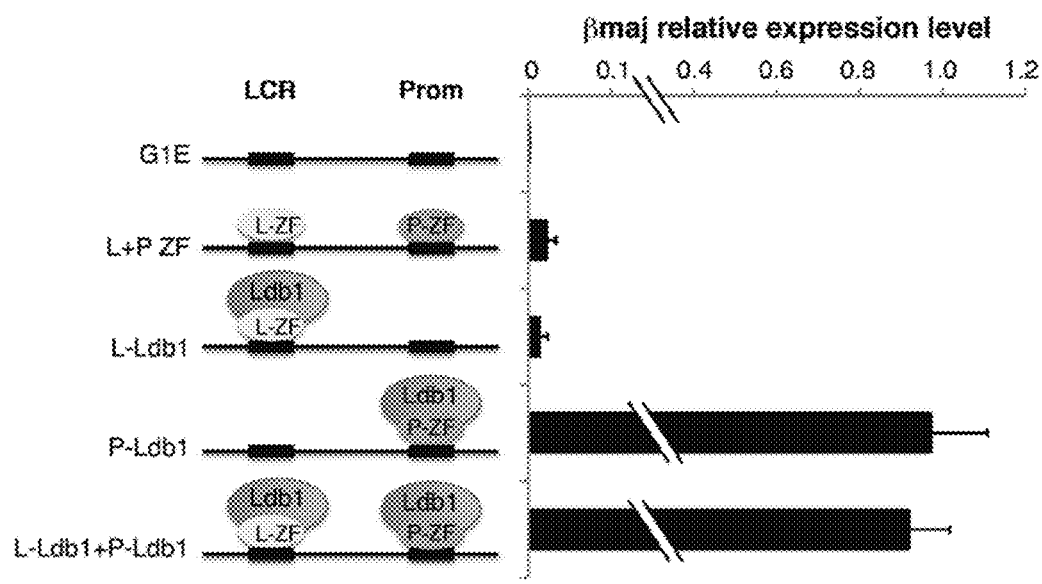
Figure 4B:
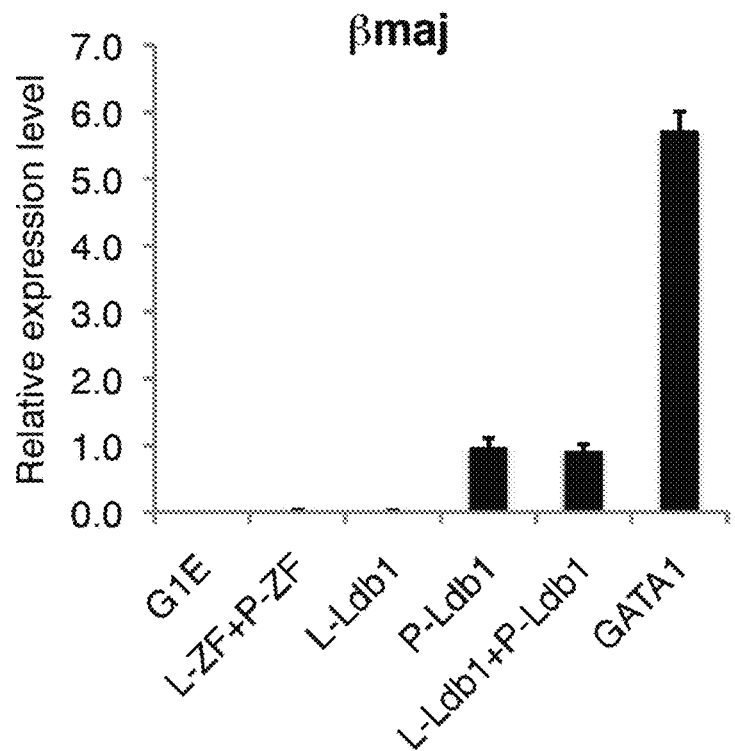
Figure 4C:
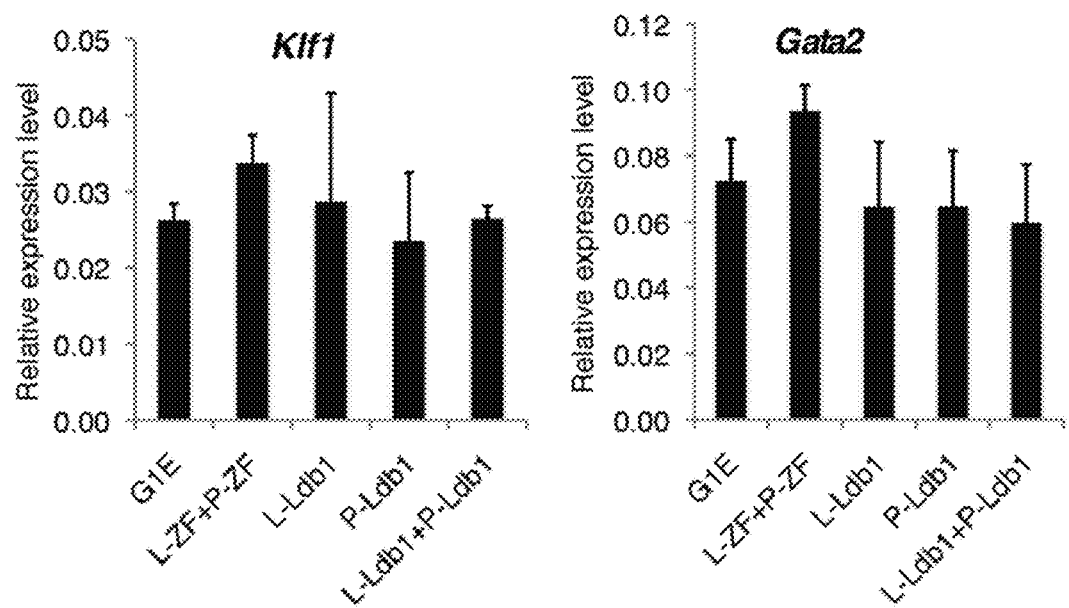
Figure 4D:
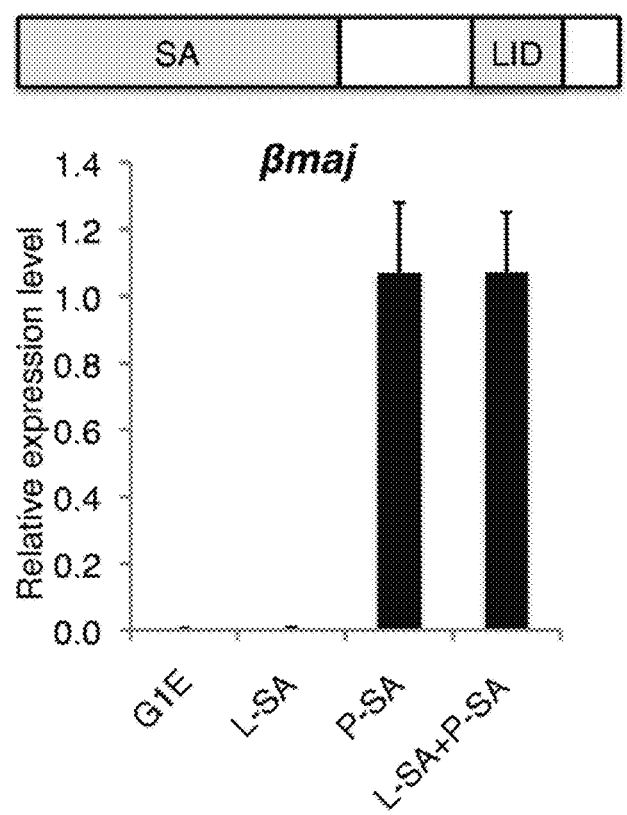

FIGS. 4A-4D show the activation of β-globin transcription in GATA1 null cells by tethered Ldb1 or its SA domain. FIG. 4A shows β-major mRNA levels as measured by RT-qPCR with primer pairs for exon 2 in G1E cells and derivatives expressing indicated ZF and ZF-Ldb1 constructs. FIG. 4B shows data in FIG. 4A re-plotted next to those obtained from induced G1E-ER4 cells (G1E+ GATA1). Note that β-major expression achieved by P-Ldb1 or L-Ldb1+PLdb1 amounts to approximately 20% of that induced by GATA1. FIG. 4C provides the relative expression of indicated erythroid genes as determined by RT-qPCR. FIG. 4D provides a schematic of Ldb1 (SA, self association domain, LID, LIM interaction domain) and β-major mRNA levels in G1E cells expressing indicated ZF fused to the SA domain of Ldb1. Transcript levels were normalized to β-actin. N≥3; error bars denote standard deviation.

Figure 5A:
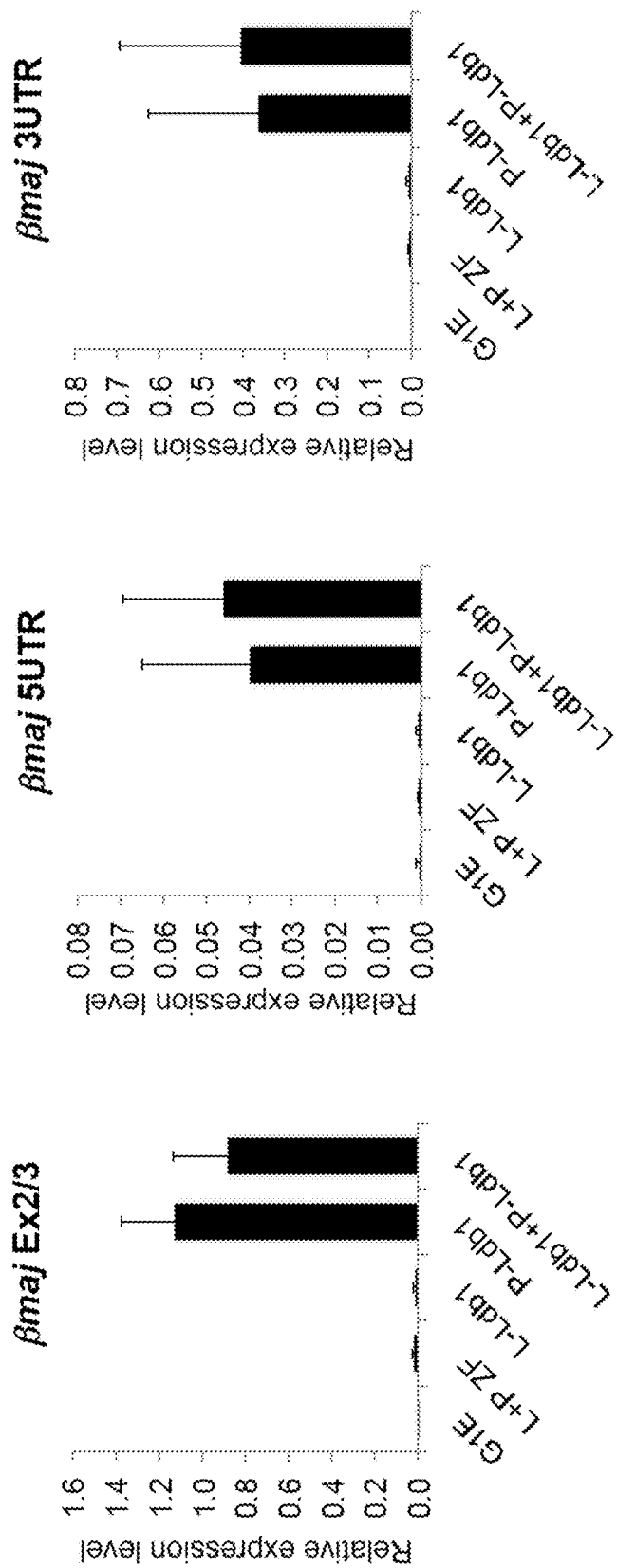
Figure 5B:
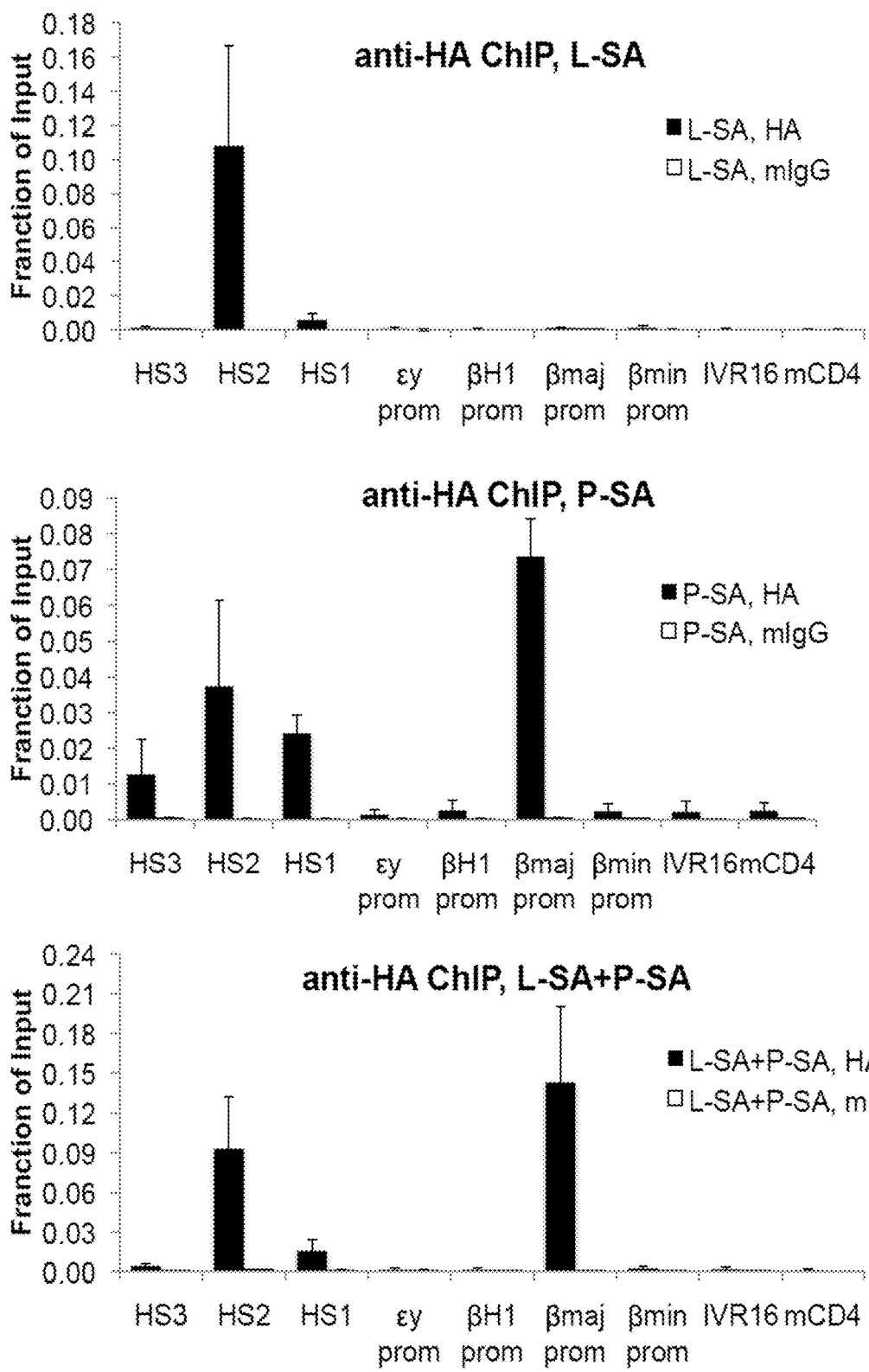
Figure 5C:
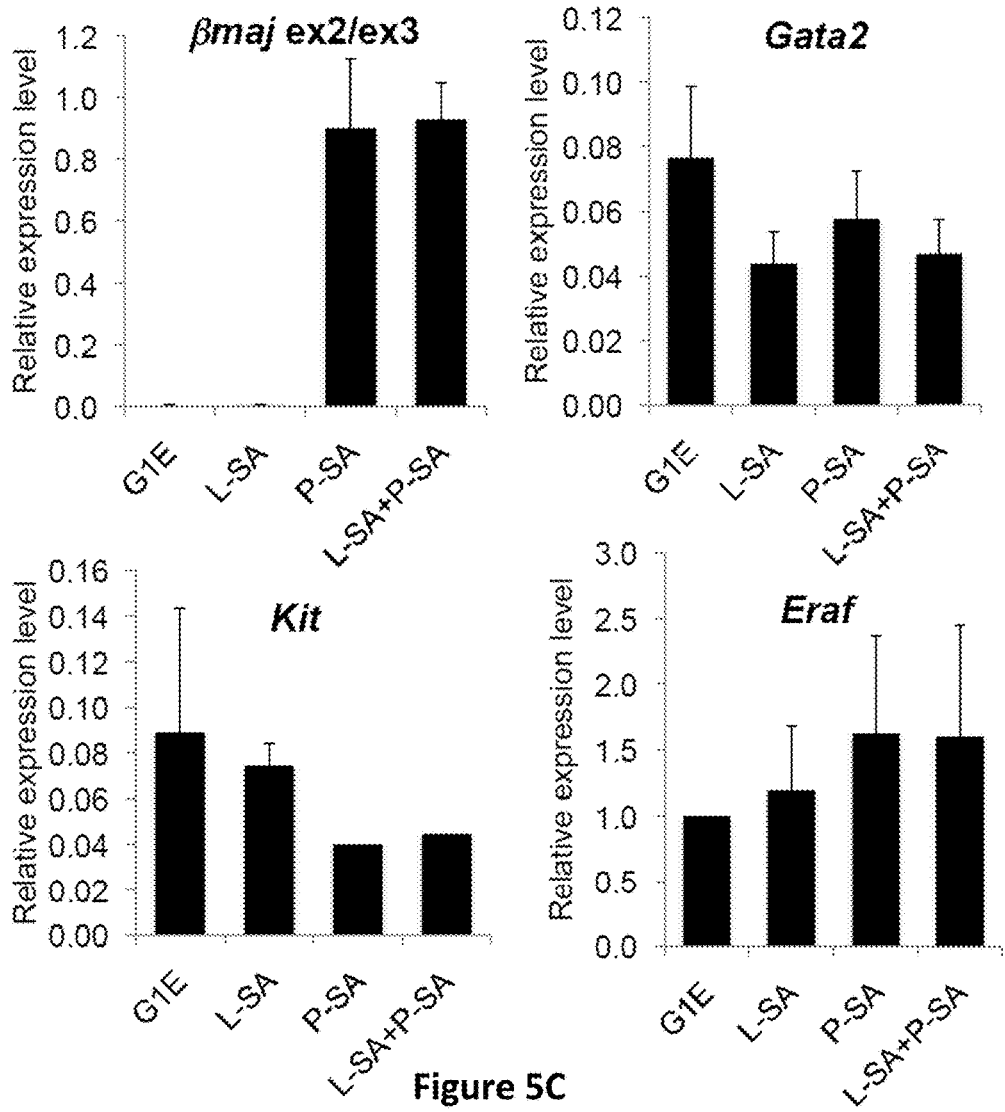
Figure 5D:
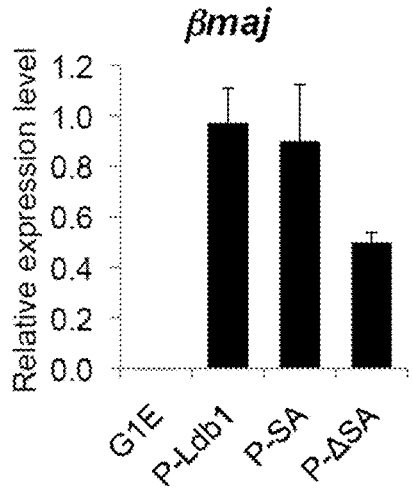

FIG. 5A shows β-major mRNA levels in ZF-Ldb1 expressing cells as measured by RT-qPCR with primer pairs for exon 2/3 junction, 5UTR and 3UTR. FIG. 5B shows anti-HA ChIP profiles in G1E cells expressing L-SA (top), P-SA (middle), and L-SA+PSA (bottom). L-SA binds selectively to HS2 of the LCR. P-SA binds to the promoter and additionally associates with HS 1, 2, 3 of the LCR but not to other regions, including the εy, βH1, and βmin genes, an intervening region (IVR16) or an inactive gene (mCD4). FIGS. 5C and 5D show mRNA levels of indicated genes as measured by RT-qPCR in G1E cells and derivatives expressing indicated ZF and ZF-SA constructs. While β-major is dramatically activated in P-SA or P-SA/L-SA cells, mRNA levels of GATA1 repressed (Gata2, Kit) and activated (Eraf) genes were largely unchanged by ZF-fusion protein expression. N=3; error bars denote standard deviation. mRNA levels were normalized to β-actin.

Figure 6A:
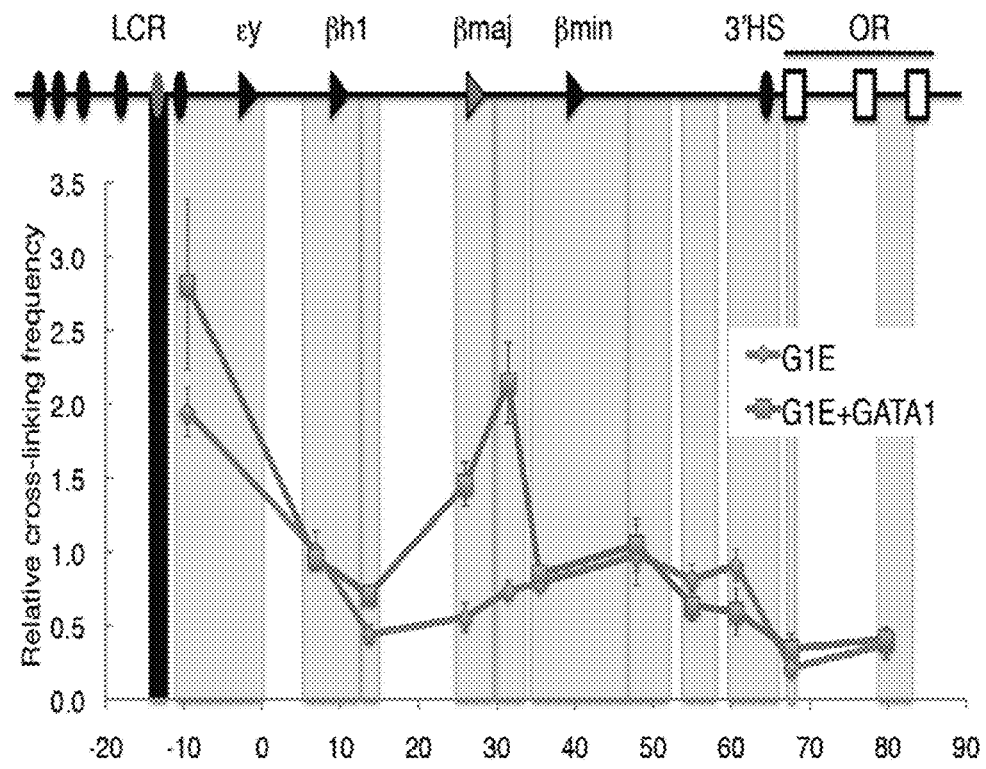
Figure 6B:
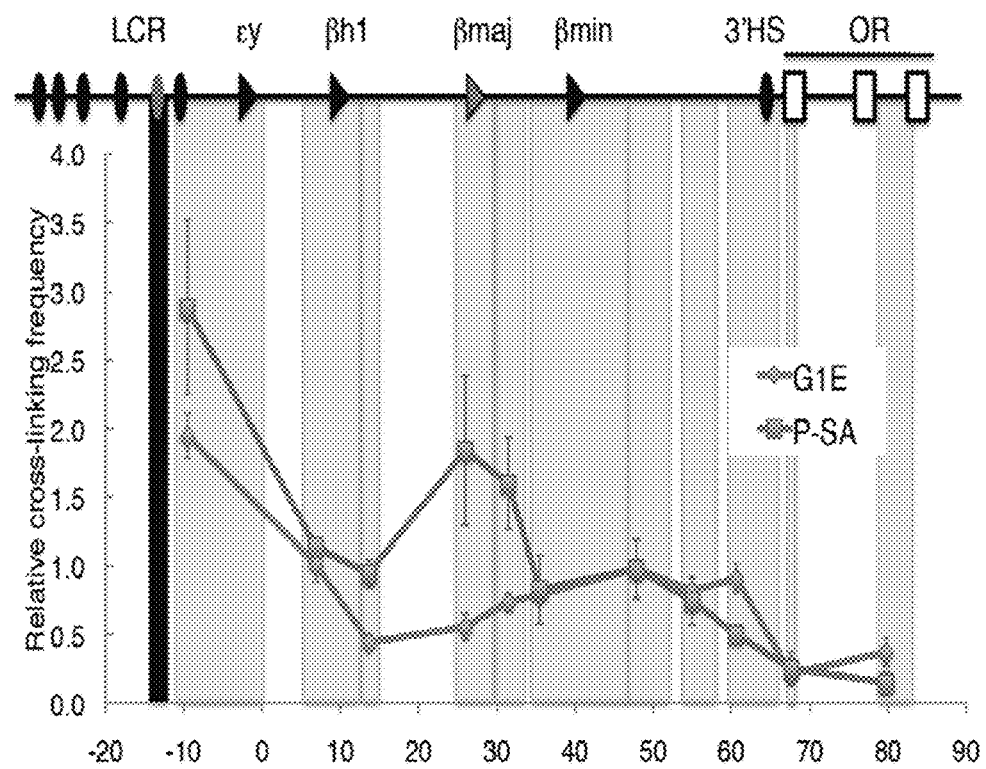
Figure 6C:
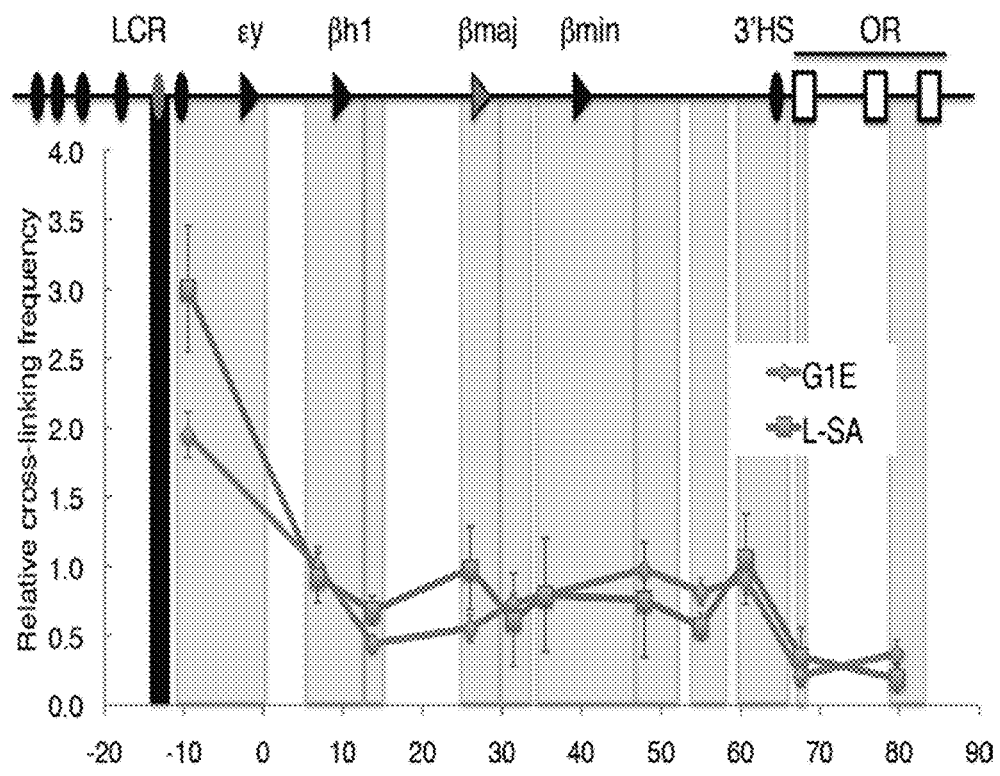

FIGS. 6A-6D show chromatin looping by the tethered Ldb1 self-association domain. FIGS. 6A-6D provide 3C assays measuring locus wide cross-linking frequencies in G1E cells or induced G1E-ER4 cells expressing GATA1, or G1E cells containing P-SA, L-SA, or L-SA+P-SA. The murine β-globin locus is depicted on top of each graph. The X-axis indicates distances (kb) from the εy gene, which represents zero. Black bar denotes the HS2-containing BglII fragment serving as anchor. Grey bars denote analyzed BglII fragments. N=3 (FIGS. 6A, 6B, 6D), and N=2 (FIG. 6C). Error bars indicate standard-error-of-mean.

Figure 7A:
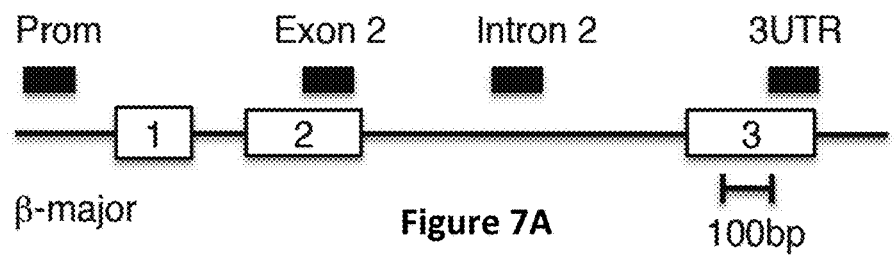
Figure 7B:
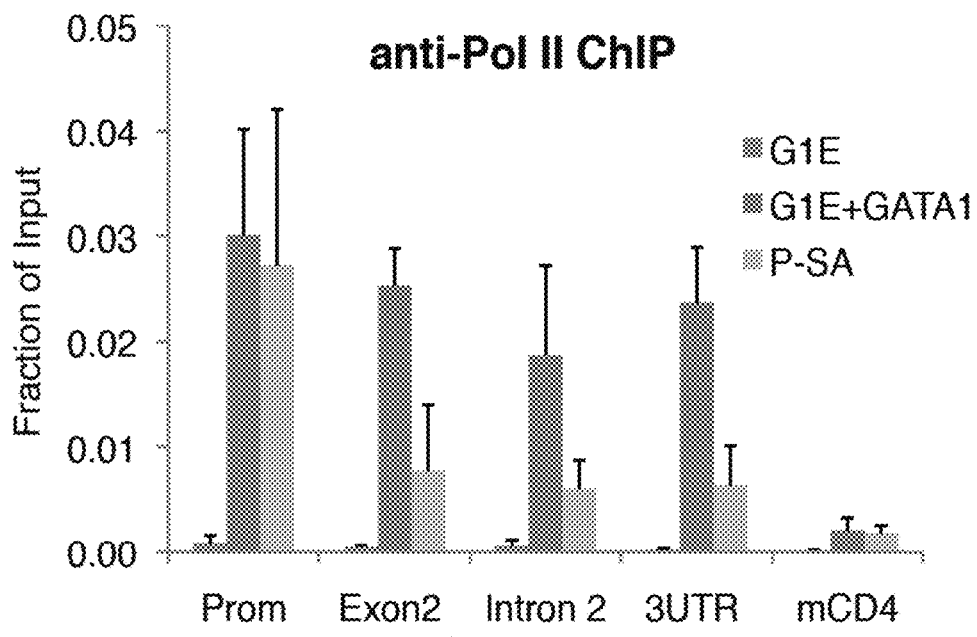
Figure 7C:
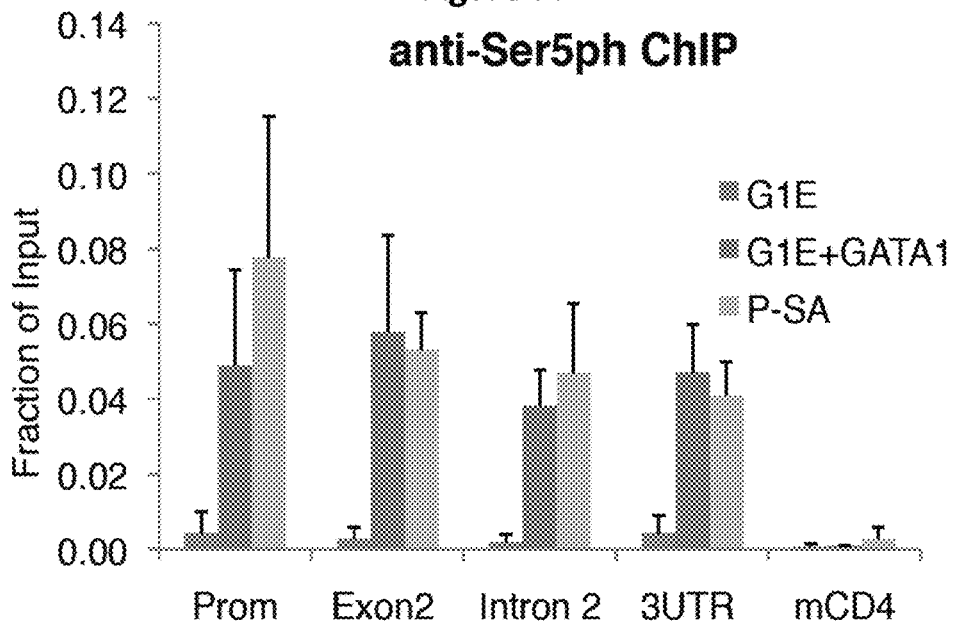

FIGS. 7A-7C show the restoration of Pol II recruitment and serine 5 phosphorylation by ZF-SA. FIG. 7A shows the location of amplicons (black bars). Prom, promoter; numbers indicate exons. FIGS. 7B and 7C provide ChIP assays with antibodies against total Pol II (FIG. 7B), ser5ph (FIG. 7C) using G1E cells or G1E cells expressing GATA1 or P-SA. While total Pol II binding at the promoter matched that induced by GATA1, Pol II levels in the body of the gene were only partially restored in P-SA cells, consistent with incomplete rescue of transcriptional elongation (compare with FIG. 4B). N=3; error bars denote standard deviation.

Figure 8A:
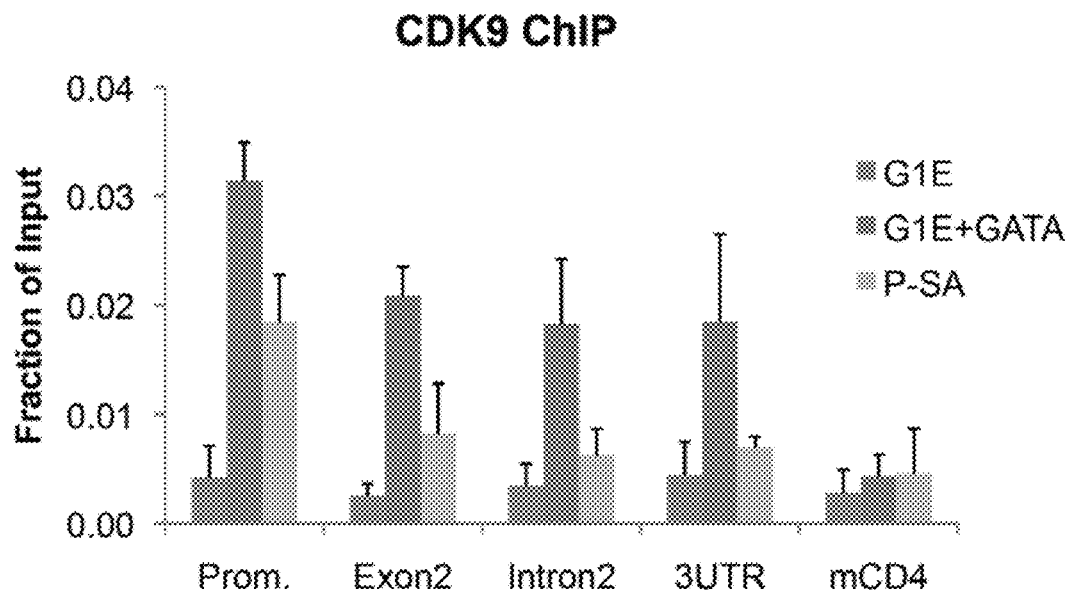
Figure 8B:
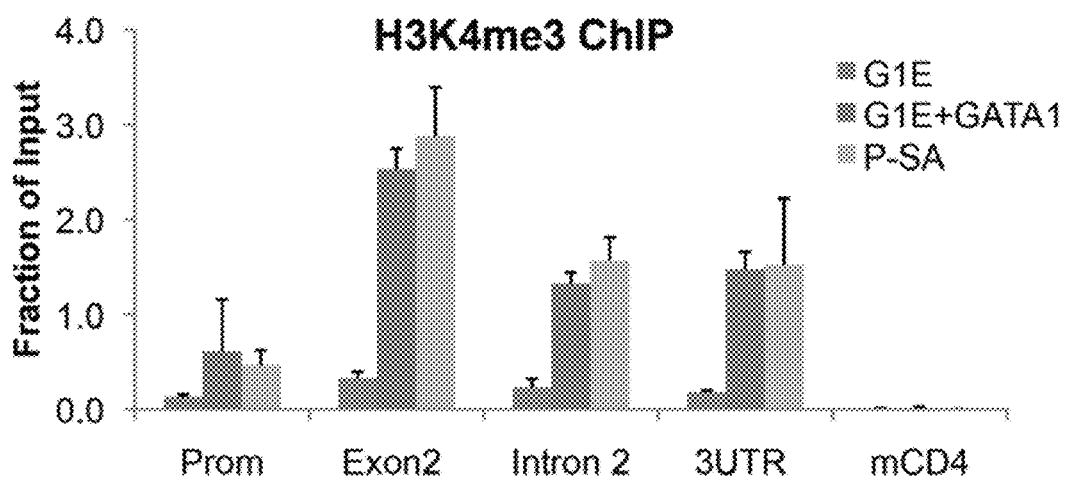

FIGS. 8A-8B show ChIP profiles with antibodies against CDK9 (FIG. 8A) and H3K4me3 (FIG. 8B) using G1E cells or derivatives expressing GATA1 or P-SA.

Figure 9A:
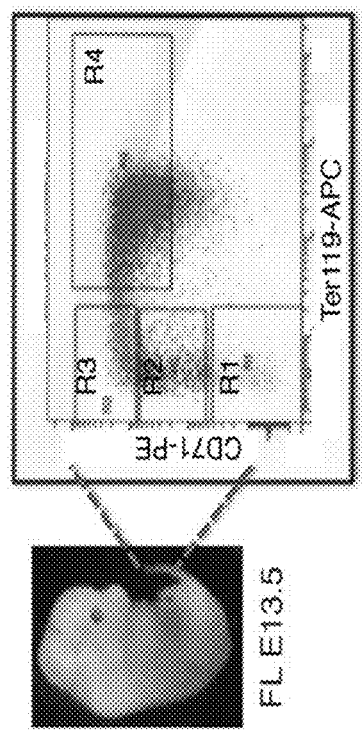
Figure 9B:
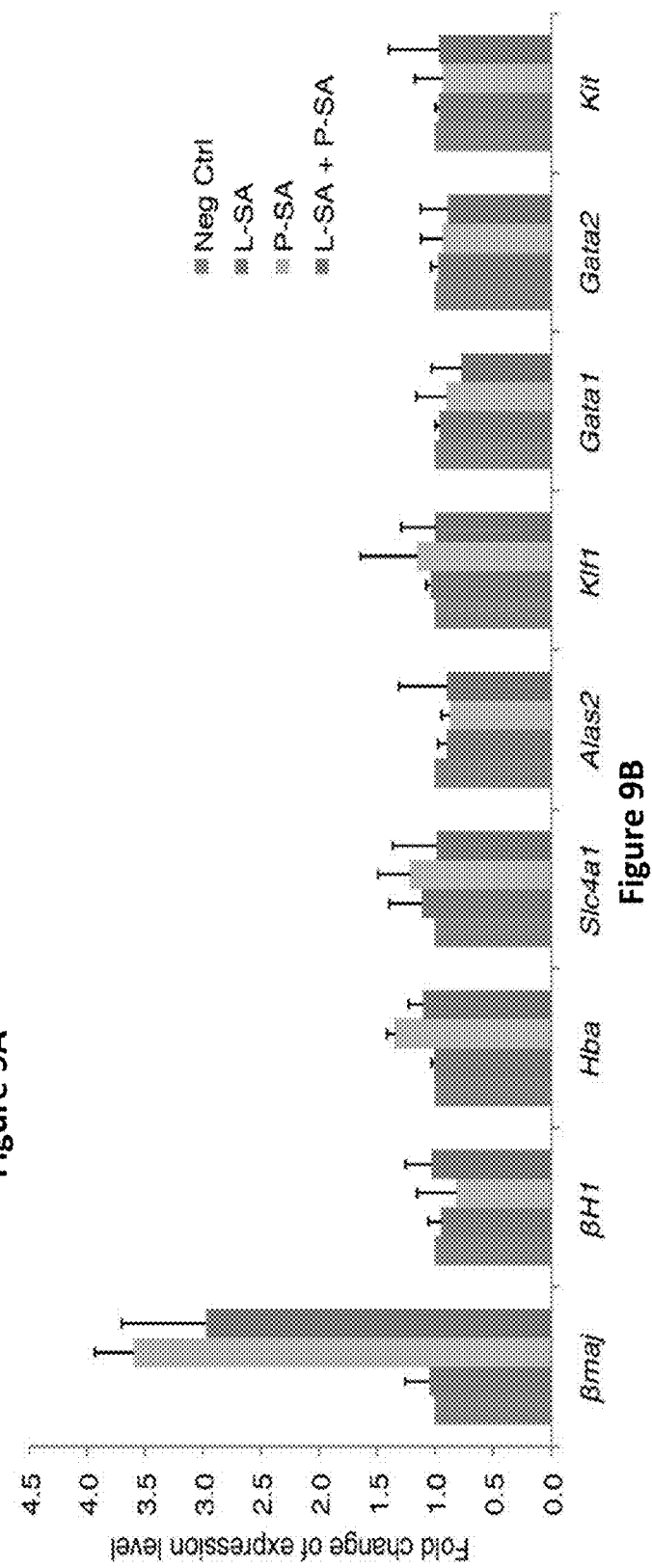

FIGS. 9A-9B show ZF-SA enhances β-globin expression in primary early progenitor cells. FIG. 9A shows the staging of E13.5 fetal liver erythroid cells by Ter119, CD71 profiling. FIG. 9B shows mRNAs from FACS purified R1 cells transduced with ZF constructs were examined by RT-qPCR with primers for the indicated genes. Negative controls (Neg Ctrl), cells expressing empty vector. Results were normalized to GAPDH. N=3; error bars denote standard deviation.

Figure 10A:
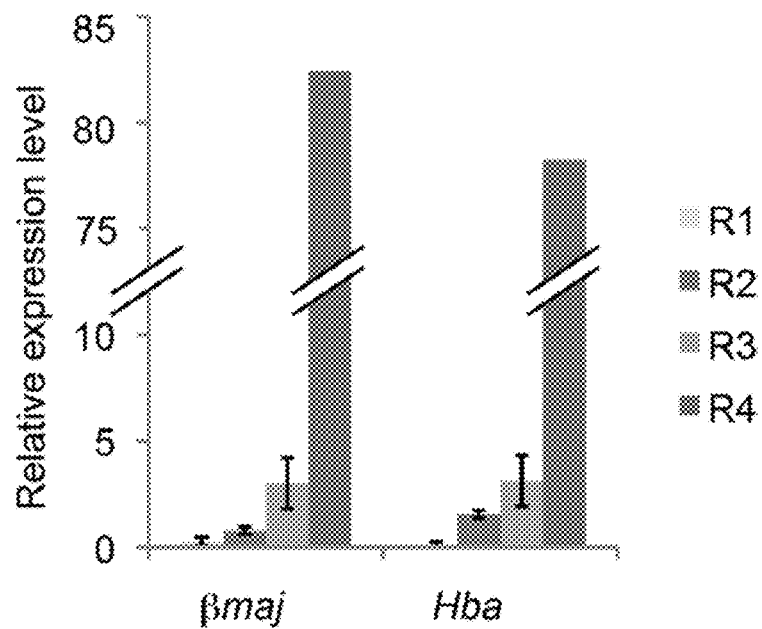
Figure 10B:
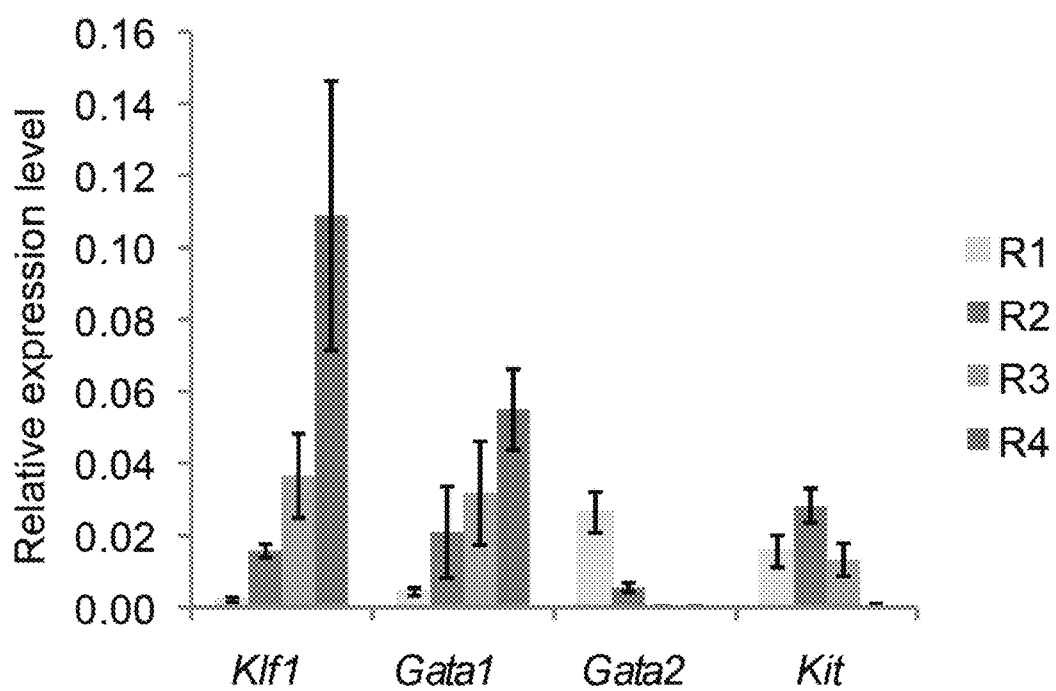
Figure 10C:
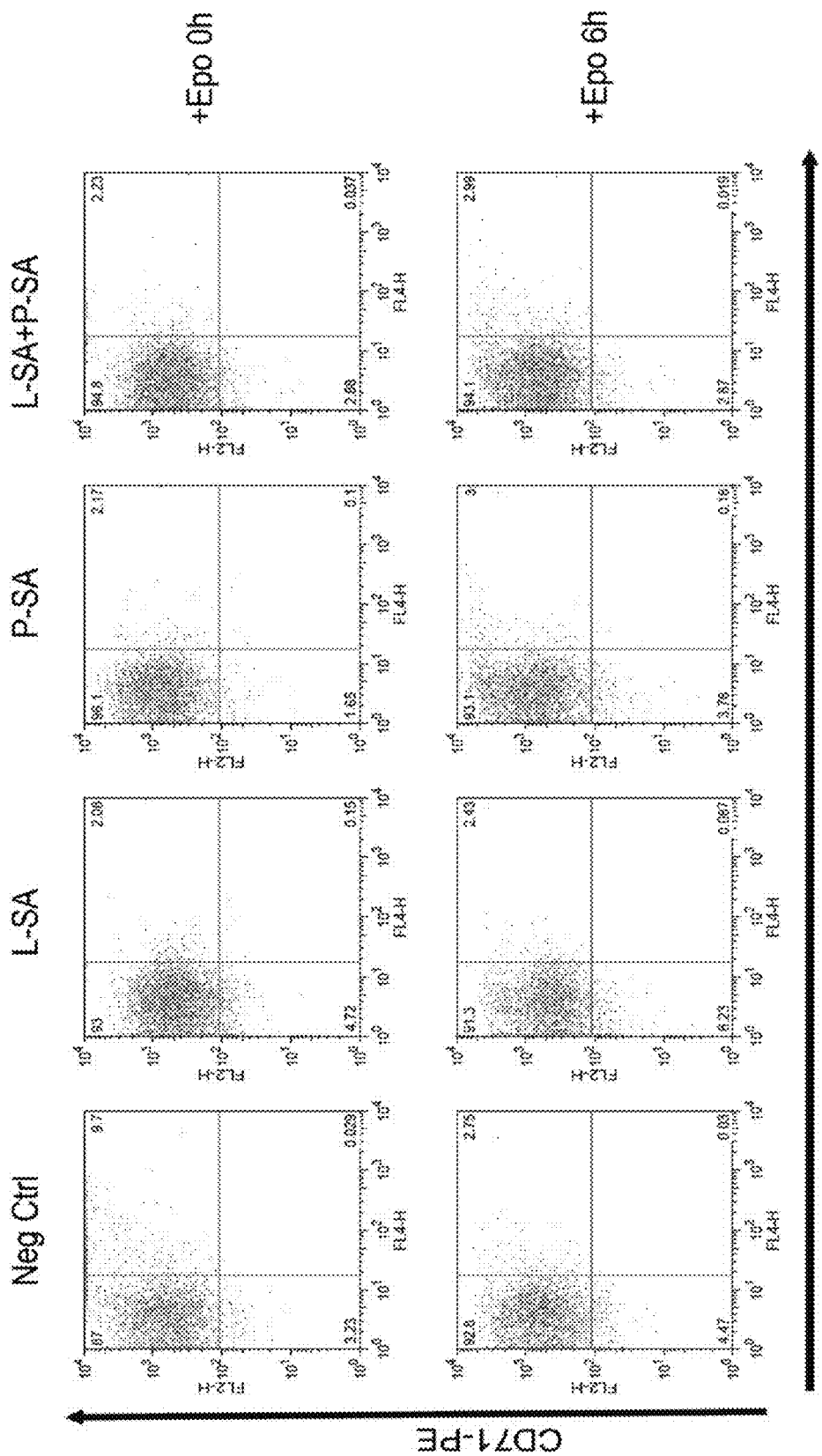

FIGS. 10A, 10B show mRNA levels of indicated genes in R1 to R4 populations of fetal liver cells as measured by qPCR. N=3; error bars denote standard deviation. FIG. 10C provides differentiation profiles of R1 cells expressing indicated constructs as measured by flow cytometry using Ter119 and CD71 surface markers.

Figure 11A:
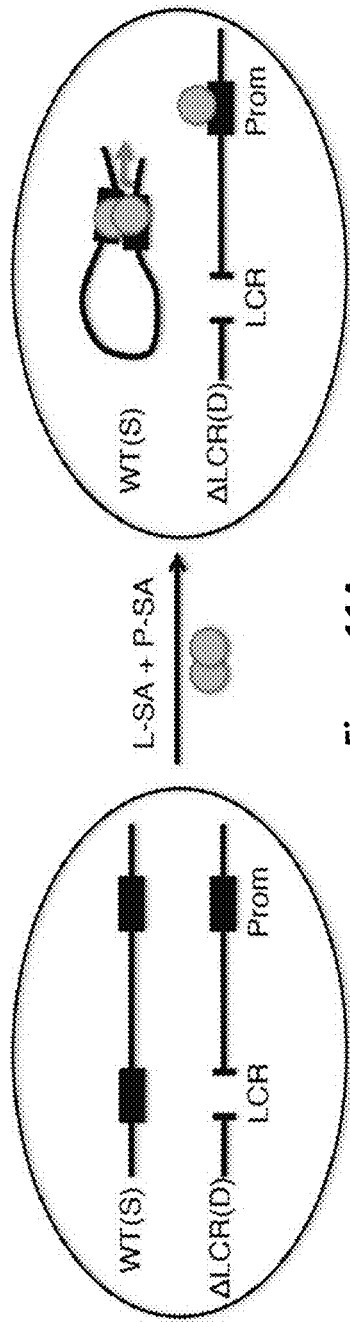
Figure 11B:
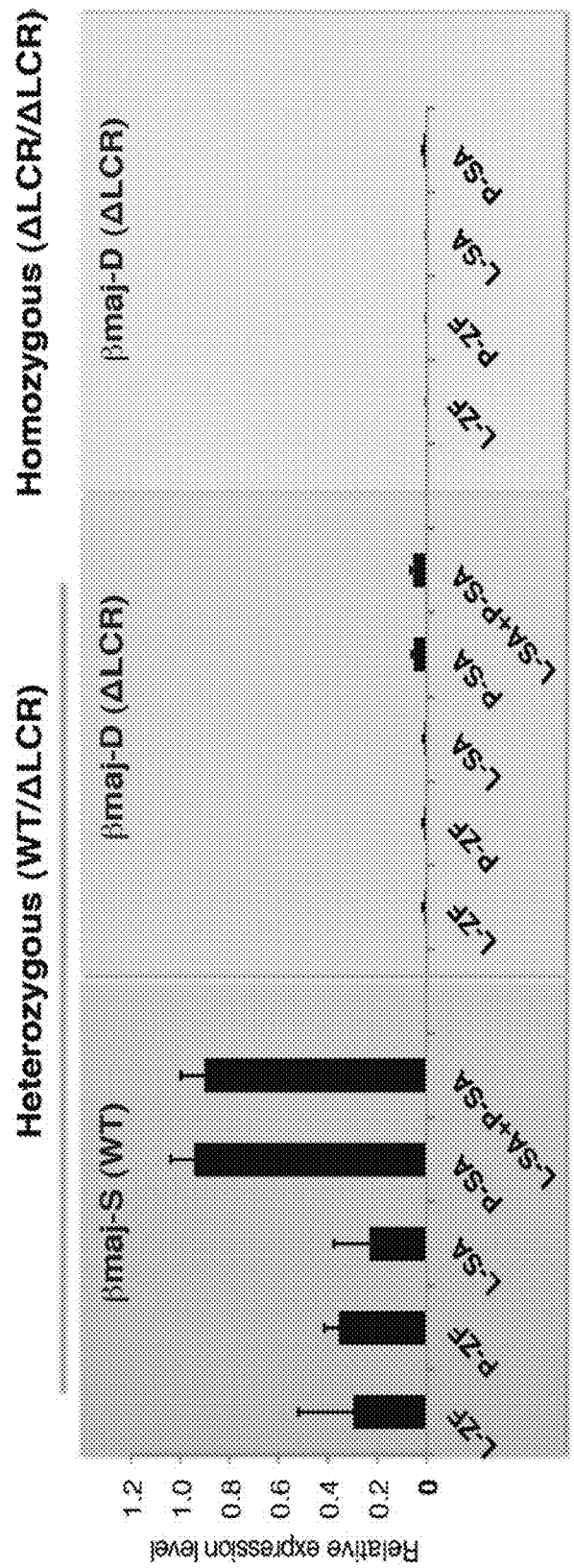

FIGS. 11A-11B show LCR-dependence of β-globin induction by ZF-SA proteins. FIG. 11A shows that the LCR deleted allele is on the background of the β-major D haplotype while the wild type allele is of the β-major S haplotype. FIG. 11B shows the β-major transcript levels as measured by allele-specific RT-qPCR in R1 cells from WT/ΔLCR or ΔLCR/ΔLCR fetal livers expressing indicated ZF-SA proteins. Transcript levels were normalized to GAPDH. N=3; error bars denote standard deviation.

Figure 12A:
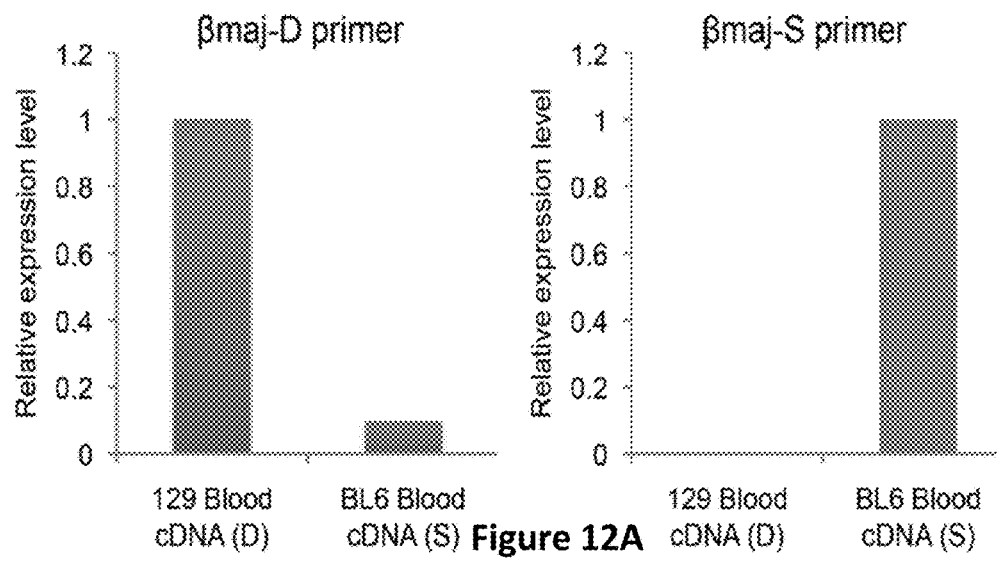
Figure 12B:
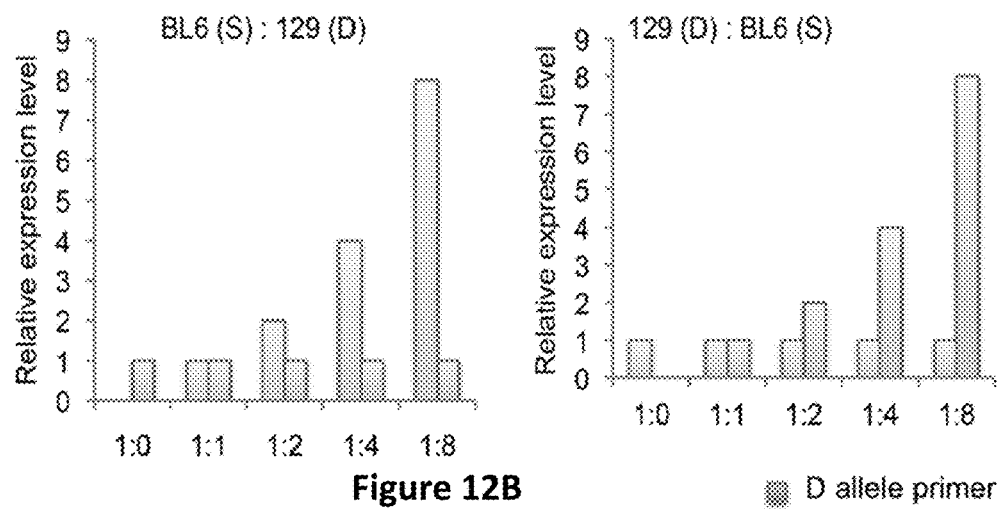
Figure 12C:
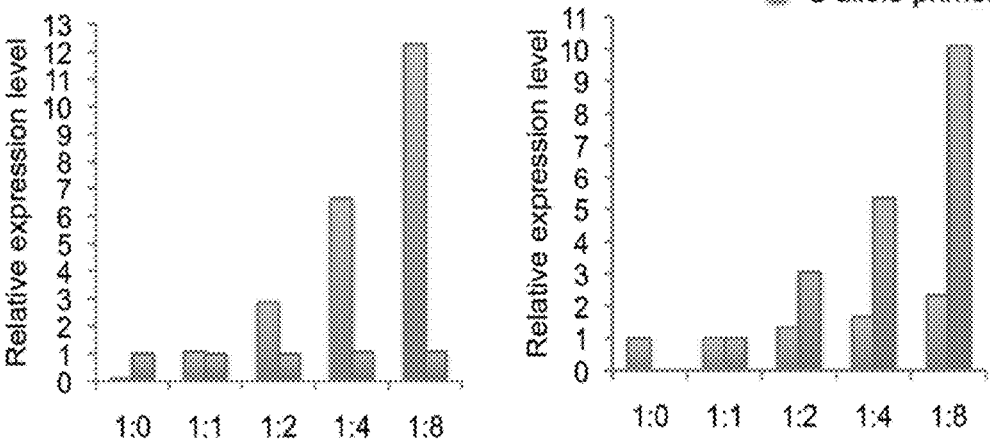

FIGS. 12A-12C show allele-specific qPCR. FIG. 12A shows β-major mRNA levels of D and S haplotypes as measured by qPCR using allele-specific primers βmaj-D and βmaj-S, respectively. cDNA from D haplotype or S haplotype was prepared from 129 or BL6 mouse strains, respectively. The βmaj-S primer specifically amplified BL6 cDNA but not 129 cDNA. In contrast, the βmaj-D primer cross-amplified BL6 cDNA with an efficiency ~10% of the βmaj-S primer. Allele specificity was further examined by mixing D-cDNA and S-cDNA templates. The observed qPCR signal (FIG. 12C) largely matched the expectation (FIG. 12B) for allele-specific qPCR. The βmaj-S signal remained unchanged with increasing amount of D cDNA verifying its amplification specificity. However, increasing the proportion of S cDNA led to an augmented signal with the D-specific primers indicative of cross-reactivity up to ~10%.

Figure 13A:
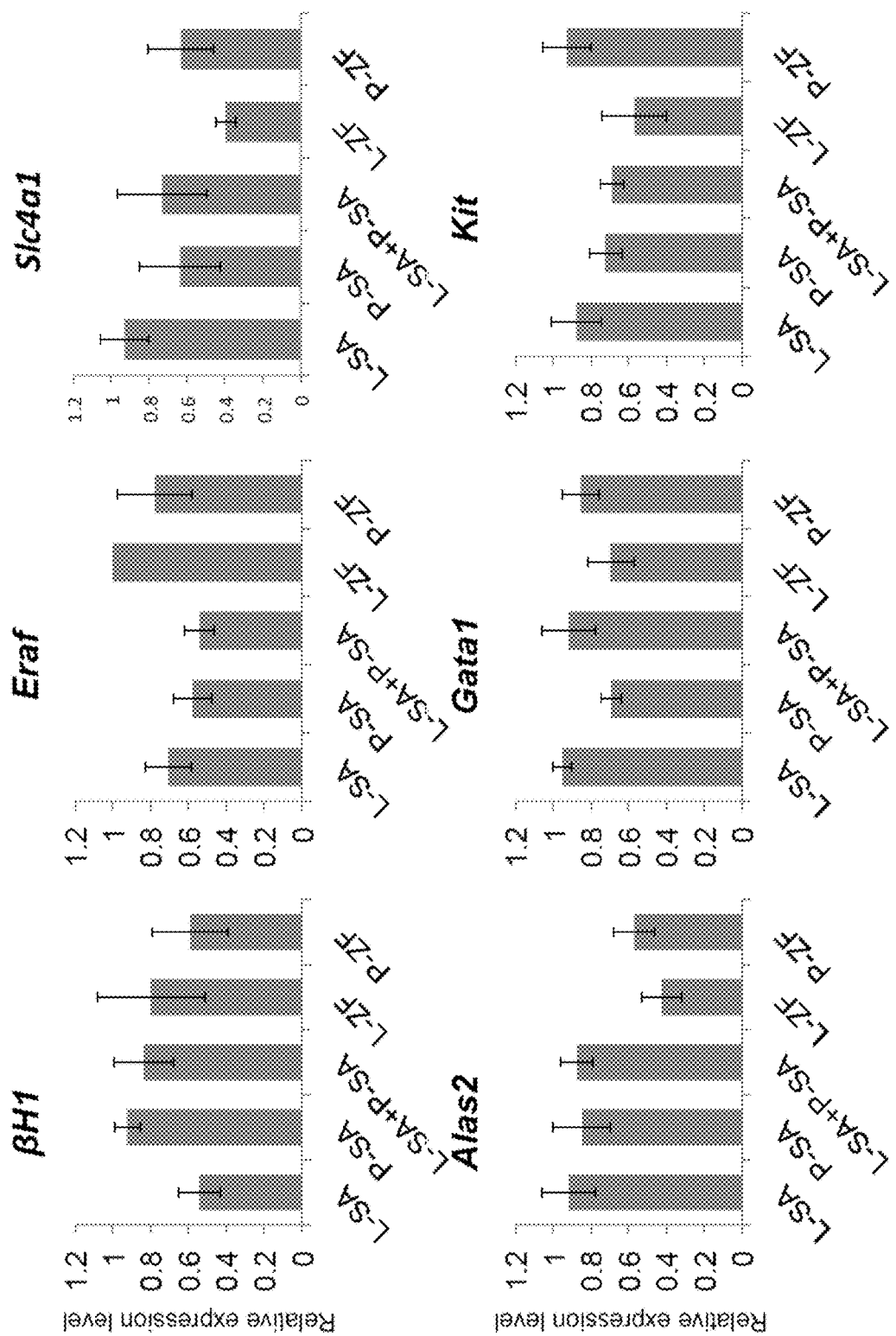
Figure 13B:
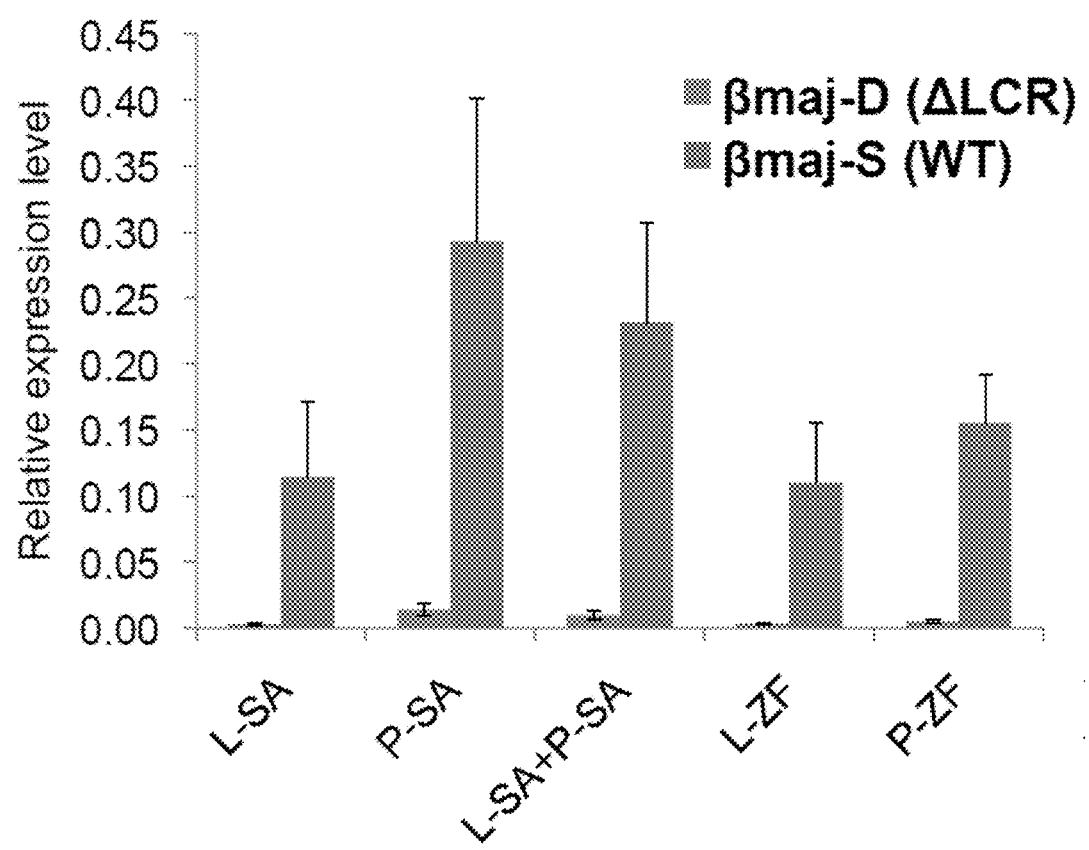
Figure 13C:
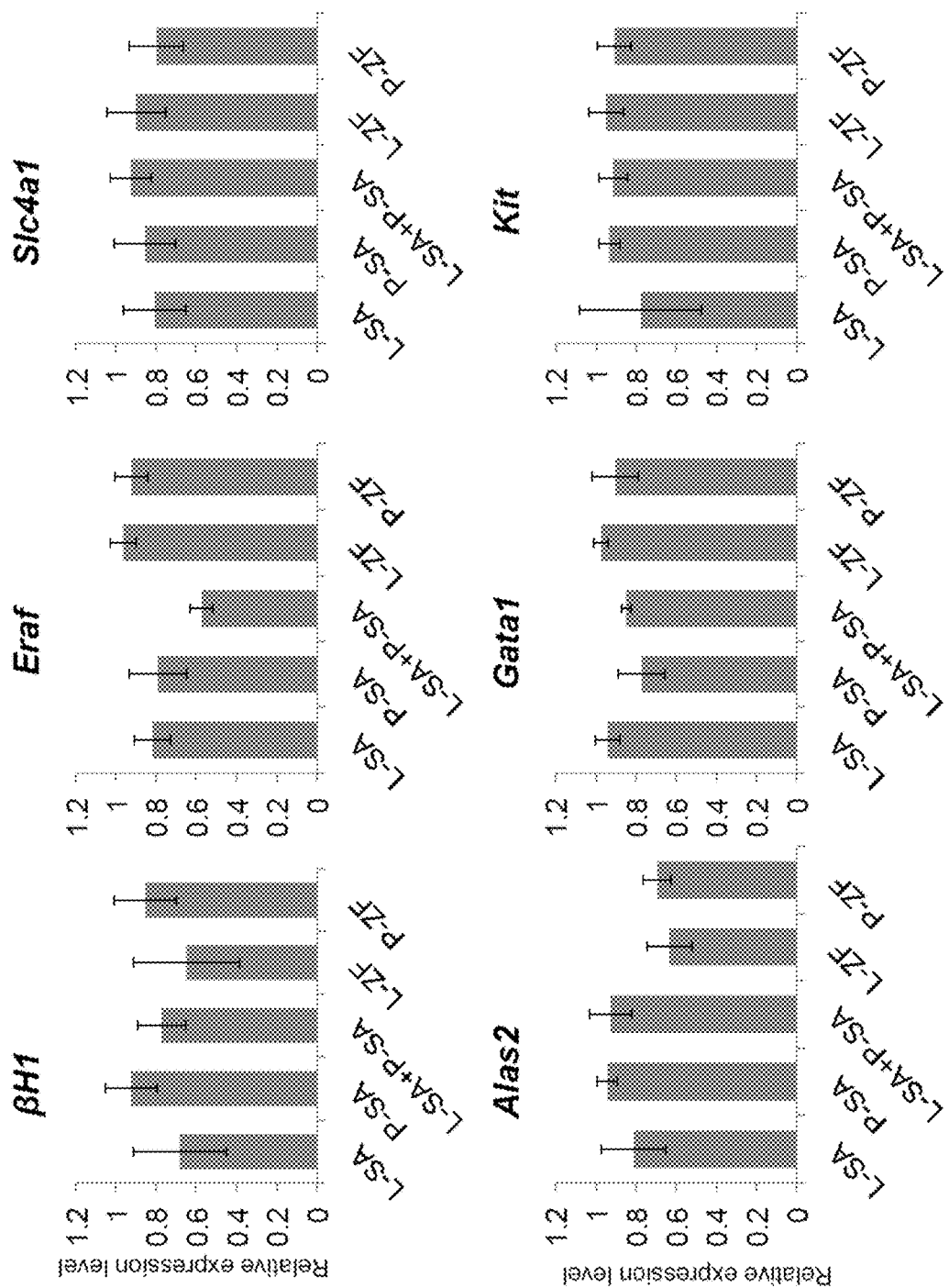

FIG. 13A shows mRNA levels of indicated genes in R1 cells from WT/ΔLCR fetal livers expressing indicated ZF-SA proteins. R1 cells were treated with erythropoietin (Epo) for 6 hours following transduction with ZF-SA expression constructs. N=3; error bars denote standard deviation. FIGS. 13B and 13C show RT-qPCR measuring mRNA levels of β-major globin (FIG. 13B) or indicated control genes (FIG. 13C) in R1 cells from WT/ΔLCR fetal livers expressing indicated ZF-SA proteins without Epo treatment. mRNA levels were normalized to GAPDH. N=3; error bars denote standard deviation.

Figure 14:
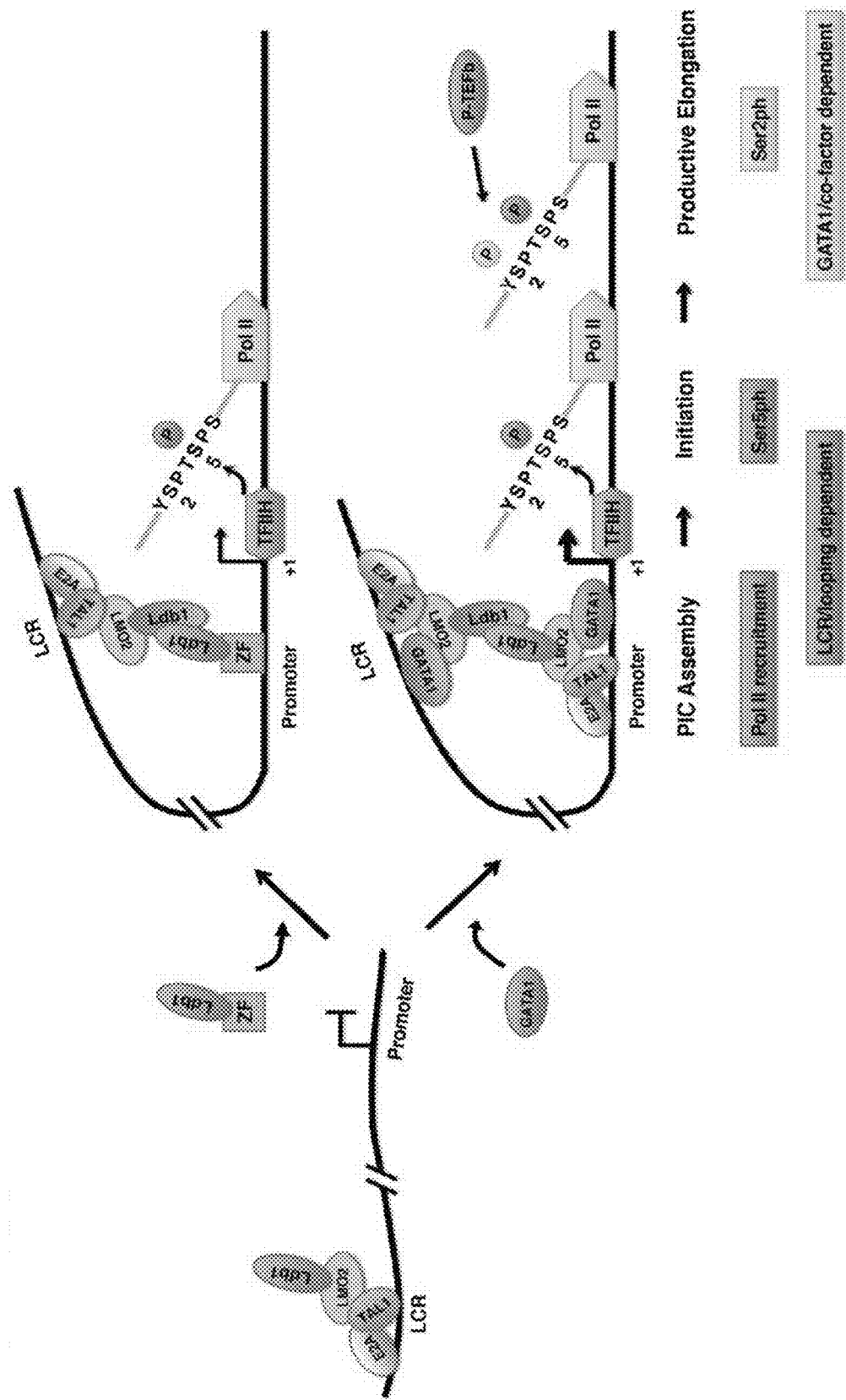

FIG. 14 provides schematic model functionally integrating chromatin looping and transcription activation. Recruitment of Ldb1 to the β-globin promoter either by ZF proteins or GATA1 promotes LCR-promoter looping. Forced chromatin looping by ZFLdb1 efficiently restores PIC assembly, Pol II recruitment, Pol II serine 5 phosphorylation (YSPTSPS—SEQ ID NO: 83), and transcription initiation. In the absence of GATA1, diminished recruitment of P-TEFb and likely additional GATA1 co-factors accounts for inefficient transcription elongation. Therefore, chromatin looping can trigger transcription initiation and can occur independently of full transcription elongation.

FIGS. 15A-15B provide the amino acid sequence of human Ldb protein. FIG. 15A provides SEQ ID NO: 1 and FIG. 15B provides SEQ ID NO: 2.

Figure 16A:
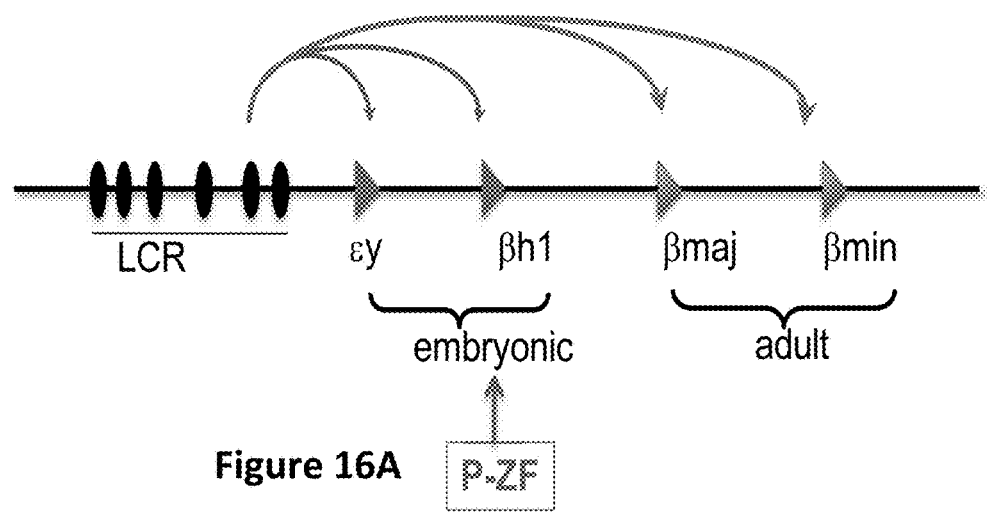
Figure 16B:
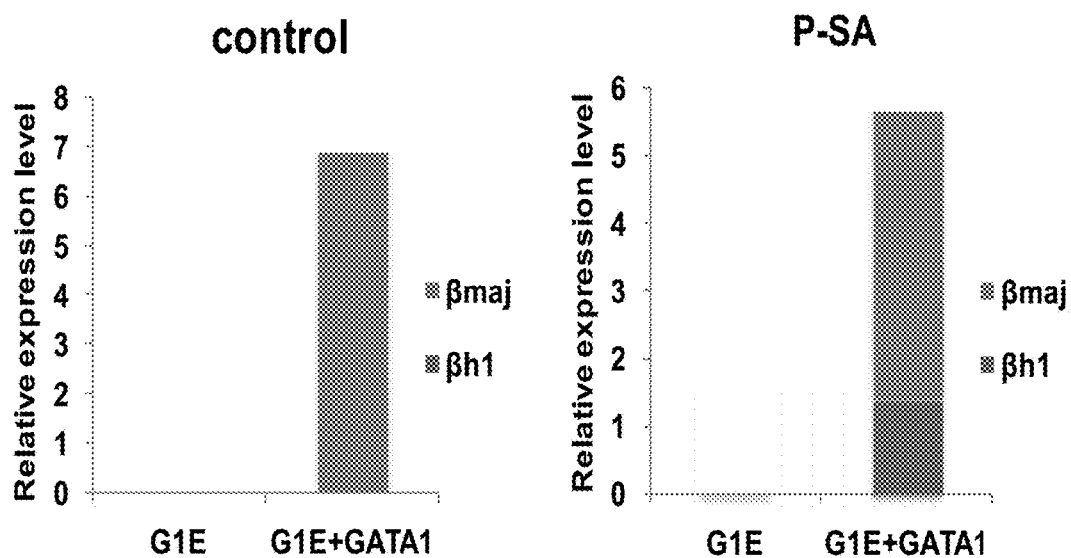

FIG. 16A shows a schematic of the experiment design for the reactivation of embryonic β-globin in adult cells. ZF proteins were designed to target the promoter of embryonic β-globin, βh1. Expression of ZF-SA fusion protein in GATA1 expressing G1E cells is expected to tether SA domain to the βh1 promoter, redirect the LCR to the silenced βh1 gene and hence activate βh1 transcription. FIG. 16B provides graphs of the mRNA levels measured by RT-qPCR in G1E cells or G1E+GATA1 cells that expressed empty vector or P-SA construct. Data were normalized to β-actin.

Figure 17:
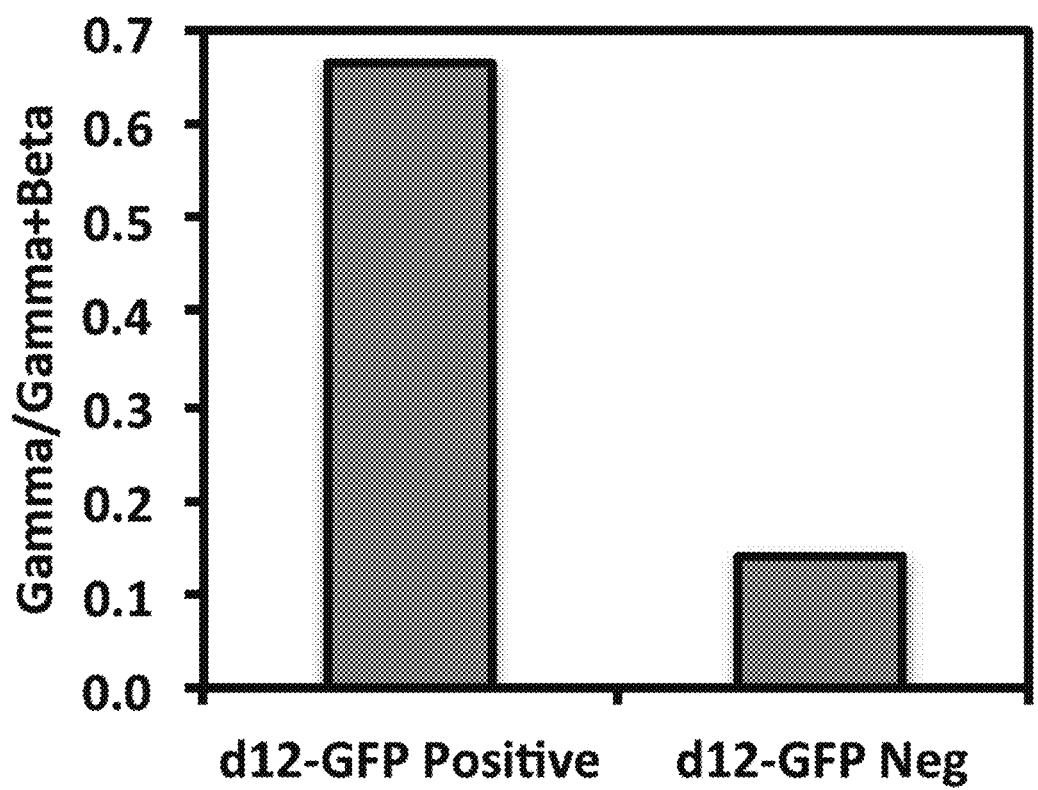

FIG. 17 provides a graph showing elevated gamma globin production in primary human erythroid cells expressing the ZF-Ld1 fusion protein (GFP+).

DETAILED DESCRIPTION OF THE INVENTION

Chromatin loops juxtapose distal enhancers with active promoters but their molecular architecture and relationship with transcription remain unclear. In erythroid cells, the locus control region (LCR) and β-globin promoter form a chromatin loop that requires transcription factor GATA1 and the associated molecule Ldb1. Artificial zinc fingers (ZF) were employed to tether Ldb1 to the β-globin promoter in GATA1 null erythroblasts in which the β-globin locus is relaxed and inactive. Remarkably, targeting Ldb1 or only its self-association domain to the β-globin promoter substantially activated β-globin transcription in the absence of GATA1. Promoter-tethered Ldb1 interacted with endogenous Ldb1 complexes at the LCR to form a chromatin loop, causing recruitment and phosphorylation of RNA polymerase II. ZF-Ldb1 proteins were inactive at alleles lacking the LCR, demonstrating that their activities depend on long-range interactions. The findings establish Ldb1 as critical effector of GATA1-mediated loop formation and indicate that chromatin looping causally underlies gene regulation.

Herein, a ZF targeting strategy was employed to address critical questions concerning the higher order organization of the chromatin fiber. Targeting the SA domain of Ldb1 to the endogenous β-globin locus compensated to a significant extent for the loss of GATA1, strongly suggesting that Ldb1 serves as an effector of GATA1 during chromatin loop formation. Forced chromatin looping by ZF-SA proteins at a native gene locus caused strong transcriptional activation, indicating that the juxtaposition of an enhancer with a promoter causally underlies gene induction.

Expression of P-SA by itself produced effects very similar to those of P-SA and L-SA coexpression. Several independent lines of investigation demonstrate that in P-SA expressing cells, forced loop formation accounts for β-globin activation. First, 3C experiments clearly showed that tethering the SA domain to the β-globin promoter fostered genomic contacts that strongly resembled those induced by GATA1 with regard to both their spatial configuration and efficiency. Second, SA domain recruitment completely restored several LCR-dependent functions at the β-globin promoter, including Pol II recruitment, serine 5 phosphorylation of Pol II, and H3K4 methylation. Third, targeted deletion of the LCR dramatically reduced β-globin transcription without diminishing the amounts of promoter-bound Ldb1 (Song et al. (2010) Blood 116:2356-64). Therefore, tethering Ldb1 or its SA domain to the promoter is not expected to produce such pronounced effects without an involvement of the LCR. Fourth, P-SA and P-SA/L-SA induction of β-globin expression was entirely dependent on the LCR, confirming an underlying looping mechanism. The ability of P-SA to potently induce loop formation is most likely explained by its ability to interact with endogenous Ldb1-containing complexes that reside at the LCR even in the absence of GATA1 (FIG. 1A; Tripic et al. (2009) Blood 113:2191-2201). In contradistinction, Ldb1 association with the β-globin promoter is entirely GATA1-dependent, and hence might represent a critical and rate limiting step during chromatin looping and high-level transcription.

The observation that the SA domain is sufficient to induce long-range chromatin interaction implies that self-association of Ldb1 is a major molecular force tying together anchored chromatin regions. Importantly, the SA domain can form multimers (Cross et al. (2010) J. Mol. Biol., 399:133-144) allowing for the formation of higher order complexes that might serve to stabilize interactions between distant chromatin fragments. However, the SA-deleted form of Ldb1 was also active, suggesting that the LID domain is also capable, albeit with lower efficiency, of recruiting the endogenous Ldb1 complex to promote long-range interactions.

Multiple contacts among DNA bound factors are likely required to provide the requisite specificities and affinities for inducing chromatin loops. Moreover, the folding of the chromatin fiber can occur in complex patterns involving simultaneous interactions between multiple segments to form what are called chromatin hubs. Simple protein dimers might be insufficient to accommodate such complex interaction patterns. In agreement, fusion of ZFs with diverse dimerizering domains (lexA, p65NFkB, the Argent™ dimerization system) or protein modules that can form multimers, such as the POZ domain of GAGA factor failed to efficiently activate β-globin expression. Thus, Ldb1 might have evolved to promote such interactions by forming homo-multimers and by engaging numerous gene-specific transcription factors, including the LMO2/TAL1/E2A complex and GATA1. Indeed, a widely used and evolutionarily conserved looping function for Ldb1 is suggested by studies in diverse organisms and cell lineages (Matthews et al. (2003) EMBO Rep., 4:1132-1137; Morcillo et al. (1997) Genes Dev., 11:2729-2740; Thaler et al. (2002) Cell 110: 237-249).

The cause-effect relationship between chromatin looping and gene regulation has been unclear. By manipulating the chromatin conformation at a native gene locus, it was found that juxtaposition of an enhancer with its target gene leads to transcription activation, indicating that looping is a prerequisite for transcription activation. In particular, forced association between the LCR and the β-globin gene sufficed to exert two functions ascribed to the LCR, the formation of a pre-initiation complex at the promoter and the generation of early elongating Pol II as reflected in serine 5 phosphorylation (Sawado et al. (2003) Genes Dev., 17:1009-1018; Song et al. (2010) Blood 116:2356-64). On the other hand, the instant observation that ZF-Ldb1 proteins completely rescued chromatin looping but only partially restored transcription elongation agrees with the notion that full transcription is not required for loop formation (Jing et al. (2008) Mol. Cell., 29:232-242; Mitchell et al. (2008) Genes Dev., 22:20-25; Palstra et al. (2008) PLoS ONE 3:e1661). Juxtaposition of the LCR with β-globin promoter likely increases the concentration of nuclear regulators at the promoter above a threshold critical for pre-initiation complex formation and early transcription elongation (FIG. 14).

Ldb1 recruitment in GATA1 null cells completely rescued chromatin looping and transcription initiation, but only partially restored transcription elongation, indicating that GATA1 contributes additional functions independently of Ldb1 and chromatin looping. Indeed, both the recruitment of P-TEFb complex and its distribution along the gene were impaired in the absence of GATA1, indicating GATA1 impacts on P-TEFb regulation at multiple levels, perhaps via direct interaction (Bottardi et al. (2011) Nucleic Acids Res., 39:3505-3519; Elagib et al. (2008) Blood 112:4884-4894) or indirectly via proteins of the BET family (Lamonica et al. (2011) Proc. Natl. Acad. Sci., 108:E159-168). In addition, GATA1 interacts with many other transcription factors and histone modifiers, the lack of which might account for inefficient transcription elongation.

In concert, these results indicate that Ldb1 functions downstream of GATA1 rather than in a parallel pathway and highlight the usefulness of this system to interrogate protein functions during distinct steps in the transcription cycle. In more general terms, this work illustrates a novel strategy to establish hierarchical orders of transcription factor function. On the background of a transcription factor deficiency, forced tethering of a potential cofactor to a chosen gene can be employed to measure its contribution to defined steps in the transcription cycle, such as loop formation, Pol II recruitment, Pol II phosphorylation, and productive transcription elongation. This approach is widely applicable for any nuclear factors that can be knocked down or knocked out.

One general finding of the instant study is that a single ZF-Ldb1 protein targeted to the β-globin promoter can induce a chromatin loop by interacting with endogenous LCR-bound factors. ZFs have previously been linked to activation domains to successfully activate gene expression (Klug, A. (2010) Annu. Rev. Biochem., 79:213-231). However, the use of ZFs to promote interactions with a potent enhancer or LCR is expected to produce more pronounced transcriptional effects. Indeed, there is no known single ZF proteins capable of activating gene transcription by a factor of more than a 1000-fold. Another advantage of a forced looping approach by a single ZF construct, especially in the context of therapeutic applications, is that efficient expression of a single molecule is easier than co-expression of two factors at matching levels.

Finally, specific chromatin loops can occur at repressed genes (Jing et al. (2008) Mol. Cell., 29:232-242), and placing an enhancer and promoter on separate loops can isolate the enhancer to render it inactive (Ameres et al. (2005) EMBO J., 24:358-367; Hou et al. (2008) Proc. Natl. Acad. Sci., 105:20398-20403). Thus, in addition to activating transcription, forced chromatin looping could be used to silence gene expression for scientific or therapeutic purposes.

The instant invention comprises compositions and methods for modulating the expression of a gene of interest (and encoded protein). In a particular embodiment, the instant invention provides fusion polypeptides which modulate the expression of a gene of interest. In a particular embodiment, the fusion polypeptide comprises a DNA binding domain and a looping factor. The DNA binding factor may be N-terminal to the looping factor. The DNA binding domain and the looping factor may be linked directly to each other or linked via a linker. Generally, the linker is a chemical moiety comprising a covalent bond or a chain of atoms that covalently attaches two domains or polypeptides. In a particular embodiment, the linker may is a polypeptide (e.g., from about 1 to about 50 amino acids, about 1 to about 20 amino acids, about 1 to about 10 amino acids, or about 1 to about 5 amino acids). The fusion polypeptide may comprise at least one affinity tag and/or at least one nuclear localization sequence (e.g., SV40 large T-antigen NLS or nucleoplasmin NLS). In a particular embodiment, the affinity tag and/or NLS are located at the N-terminus of the fusion polypeptide.

The DNA binding domains may specifically bind a unique or rare predetermined target genomic sequence. The DNA binding domain may be any synthetic or pre-existing natural DNA binding domain. Examples of DNA binding domains include, without limitation, peptide nucleic acids (PNA), zinc finger proteins (ZFP), and transcription activator-like effector (TALE) proteins. In a particular embodiment, the DNA binding domain is a zinc finger protein.

The zinc finger protein may be engineered to recognize and bind to any nucleic acid sequence of choice (see, e.g., Bartsevich et al. (2003) Stem Cells 21:632-637; Klug, A. (2010) Annu. Rev. Biochem., 79:213-231; Beerli et al. (2002) Nat. Biotechnol., 20:135-141; Pabo et al. (2001) Ann. Rev. Biochem., 70:313-340; Isalan et al. (2001) Nat. Biotechnol., 19:656-660; Segal et al. (2001) Curr. Opin. Biotechnol., 12:632-637; Sera et al. (2002) Biochemistry 41:7074-7081; Choo et al. (2000) Curr. Opin. Struct. Biol., 10:411-416; Zhang et al. (2000) J. Biol. Chem., 275(43): 33850-33860; Doyon et al. (2008) Nat. Biotechnol., 26:702-708; Santiago et al. (2008) Proc. Natl. Acad. Sci., 105:5809-5814; U.S. Pat. Nos. 6,453,242; 6,607,882; and 6,534,261; www.zincfingertools.org; bindr.gdcb.iastate.edu/ZiFiT/; Mandell et al. (2006) Nuc. Acid Res., 34:W516-W523; Sander et al. (2007) Nuc. Acid Res., 35:W599-W605). The zinc finger binding domain may comprise at least one, two, three, four, or more zinc finger recognition regions (i.e., zinc fingers). Zinc finger recognition regions and/or multi-fingered zinc finger proteins may be linked together using suitable linker sequences (e.g., linkers may comprise one or more amino acids, particularly about five or more amino acids in length).

As with the zinc finger proteins, the TALE protein contains a plurality of DNA binding regions that, in combination, bind to the desired target sequence (Gu et al. (2005) Nature 435:1122; Yang et al. (2006) Proc. Natl. Acad. Sci., 103:10503; Kay et al. (2007) Science 318:648; Sugio et al. (2007) Proc. Natl. Acad. Sci., 104:10720; Romer et al. (2007) Science 318:645; Schornack et al. (2006) J. Plant Physiol. 163:256). TALE proteins may be engineered to bind a desired sequence by known methods (see, e.g., U.S. Patent Application Publication No. 2011/0145940 and WO 2010/079430).

In a particular embodiment, the DNA binding domain specifically recognizes and binds a target sequence in a promoter of the gene of interest. The target sequence may be about 10 to about 30 nucleotides in length, particularly about 15 to about 21 nucleotides in length. In a particular embodiment, the promoter is a globin promoter such as the β-major promoter or the fetal (gamma) gene promoter. The sequence of mouse β-major globin gene (Hbb-b1) is provided in Gene ID: 15129 (GenBank Accession No. NM_008220.4), human β-major globin gene (HBB) is provided in Gene ID: 3043 (GenBank Accession No. NM_000518.4), human fetal gamma globin genes (HBG1 and HBG2) are provided in Gene ID: 3047 and 3048 (GenBank Accession Nos. NM_000559.2 and NM_000184.2). Targeted sequences may be within the promoter region including, but not limited to the sequence provided in FIG. 1B or the corresponding sequence in other species. In a particular embodiment, the target sequence specifically bound by the DNA binding domain is not a known transcription binding site and does not interfere with the binding of transcription factors to known transcription binding sites.

The looping factor of the fusion polypeptide of the instant invention may be a cofactor in the formation of chromatin loops and may form dimers or multimers. In a particular embodiment, the looping factor is a LIM domain binding protein (Ldb or NLI or CLIM; for human Ldb1 protein: Gene ID: 8861; GenBank Accession No. NP_001106878 (FIG. 15B; SEQ ID NO: 2), NP_003884.1 (FIG. 15A; SEQ ID NO: 1)) or a fragment thereof. The Ldb may be from any species. In a particular embodiment, the Ldb protein is human Ldb1 or Ldb2, particularly Ldb1. In a particular embodiment, the looping factor is an N-terminal fragment (i.e., less than the full-length) of Ldb1 that comprises the self-association domain (amino acids 1-200 of GenBank Accession No. NP_003884.1 which equals to amino acids 37-237 of GenBank Accession No. NP_001106878). The N-terminal fragment of Ldb1 may comprise amino acids 1 to about 150, 1 to about 175, 1 to about 200, 1 to about 225, 1 to about 250, 1 to about 275, 1 to about 300, 1 to about 325, or 1 to about 350 of Ldb1 (e.g., of GenBank Accession No. NP_003884.1). In another embodiment, the looping factor is a C-terminal fragment (i.e., less than the full-length) of Ldb1 that lacks the self-association domain. The C-terminal fragment of Ldb1 may lack amino acids 1 to about 150, 1 to about 175, 1 to about 200, 1 to about 225, 1 to about 250, 1 to about 275, 1 to about 300, 1 to about 325, or 1 to about 350 of Ldb1 (e.g., of GenBank Accession No. NP_003884.1). The amino acid sequence of the Ldb1 in the fusion polypeptide of the instant invention may have at least 70%, 75%, 80%, 85%, 90%, 85%, 97%, 99%, or 100% homology with the above identified sequences.

Nucleic acid molecules encoding the fusion polypeptides are also encompassed by the instant invention. The nucleic acid sequences encoding the DNA binding domain and looping factor are preferably operably linked (e.g., directly or through a linker) and in-frame. Nucleic acid molecules encoding the fusion polypeptides of the invention may be prepared by any method known in the art. The nucleic acid molecules may be maintained in any convenient vector, particularly an expression vector. Different promoters may be utilized to drive expression of the nucleic acid sequences based on the cell in which it is to be expressed. Antibiotic resistance markers are also included in these vectors to enable selection of transformed cells. Fusion polypeptide encoding nucleic acid molecules of the invention include cDNA, DNA, RNA, and fragments thereof which may be single- or double-stranded.

The compositions and methods of the instant invention may further comprise a second fusion polypeptide comprising a looping factor and a DNA binding domain. In a particular embodiment, the looping factor of the second fusion polypeptide is the same as the looping factor of the first fusion polypeptide. The DNA binding domain of the second fusion polypeptide may specifically bind a target sequence within an LCR. The target sequence may be about 10 to about 30 nucleotides in length, particularly about 15 to about 21 nucleotides in length. In a particular embodiment, the DNA binding domain of the second fusion polypeptide binds the hypersensitive site 2 (HS2) of the LCR. Gene ID: 15128 provides a sequence of the Hbb-ar hemoglobin, activating region (*Mus musculus*) and Gene ID: 387281 provides a sequence of the LCRB locus control region, beta (*Homo sapiens*). Targeted sequences may be within the LCR region including, but not limited to, the HS2 sequence provided in FIG. 1B or the corresponding sequence in other species. The first and second fusion polypeptides (or nucleic acids encoding the same) may be administered simultaneously and/or sequentially. In a particular embodiment, the first and second fusion polypeptides are encoded by separate nucleic acid molecules in the same vector. Alternatively, the first and second fusion polypeptides are encoded by separate nucleic acid molecules in separate vectors. Compositions comprising a single nucleic acid molecule encoding the first and second fusion polypeptides or separate nucleic acid molecule encoding the first and second fusion polypeptides and at least one pharmaceutically acceptable carrier are encompassed by the instant invention.

While increasing the expression of a protein of interest is described throughout the instant application, the fusion polypeptides of the instant invention may also be used to repress the expression of a protein of interest. For example, the gene locus of the Kit cytokine is distinctly configured upon its repression during cell maturation. Accordingly, fusion polypeptides comprising a DNA binding domain specific for the Kit cytokine gene locus can recreate the looped chromatin organization to repress expression. For example, the target sequence of the DNA binding domain may be in at least one of the three characterized regulatory elements (Jing et al. (2008) Molecular Cell 29:232-42). The fusion polypeptides of the instant invention may also be used to force chromatin loops to misdirect functional regulatory elements of genes to modulate their expression. The fusion polypeptides may also be used to modulate other processes involving DNA in which multiple regulatory sequences are functionally or physically interacting with each other (e.g., DNA replication, DNA repair, and recombination).

Notably, some complex regulatory elements such as locus control regions provide a high degree of tissue- and/or developmental stage specificity. Accordingly, the generation of chromatin loops in this context can be used to achieve temporally accurate and tissue-specific gene regulation, thereby providing superior gene regulation over conventional gene therapies which lack desired levels and/or specificity.

In accordance with the instant invention, compositions and methods for inhibiting (e.g., reducing or slowing), treating, and/or preventing a disease or disorder in a subject are provided. In a particular embodiment, the methods comprise administering to a subject in need thereof at least one nucleic acid molecule encoding the fusion polypeptide(s) of the instant invention. The disease may be any disease in which the gene regulatory mechanisms are perturbed (e.g., increased or decreased). The fusion polypeptide may then be directed to the promoter of the gene of interest in order to modulate expression. The disease or disorder may be a congenital disorder. In a particular embodiment, the disease is beta-thalassemia, sickle cell anemia and other hemolytic anemias. In a particular embodiment, the DNA binding domain specifically binds a globin promoter such as the fetal (gamma) gene or embryonic β-globin promoter. In another embodiment, the disease is cancer and the fusion polypeptides of the instant invention repress the expression of an oncogene through the formation of chromatin loops.

In a particular embodiment of the instant invention, vectors encoding the fusion polypeptide are delivered to the subject. In a particular embodiment, the nucleic acid molecules are delivered to a subject via a viral vector. Viral vectors include, without limitation, adenoviral vectors, adeno-associated virus-(AAV) vectors, and retroviral vectors (e.g., lentiviral vectors; murine leukemia virus (MLV), human immunodeficiency virus (HIV), feline immunodeficiency virus (FIV), and equine infectious anemia virus (EIAV). The nucleic acid molecules encoding the fusion polypeptides may be under the control of any promoter. In a particular embodiment, the promoter is cell-type specific (e.g., hematopoietic stem/progenitor cells).

Compositions comprising at least one fusion polypeptide or at least one nucleic acid molecule encoding the fusion polypeptide and at least one pharmaceutically acceptable carrier are encompassed by the instant invention. As explain hereinabove, such compositions may be administered, in a therapeutically effective amount, to a patient in need thereof for the treatment of a disease or disorder.

The agents and compositions of the present invention can be administered by any suitable route, for example, by injection (e.g., for local (direct) or systemic administration), oral, pulmonary, topical, nasal or other modes of administration. The composition may be administered by any suitable means, including parenteral, intramuscular, intravenous, intraarterial, intraperitoneal, subcutaneous, topical, inhalatory, transdermal, intrapulmonary, intraareterial, intrarectal, intramuscular, and intranasal administration. In a particular embodiment, the composition is administered intravenously. In general, the pharmaceutically acceptable carrier of the composition is selected from the group of diluents, preservatives, solubilizers, emulsifiers, adjuvants and/or carriers. The compositions can include diluents of various buffer content (e.g., Tris HCl, acetate, phosphate), pH and ionic strength; and additives such as detergents and solubilizing agents (e.g., Tween 80, Polysorbate 80), anti oxidants (e.g., ascorbic acid, sodium metabisulfite), preservatives (e.g., Thimersol, benzyl alcohol) and bulking substances (e.g., lactose, mannitol). The compositions can also be incorporated into particulate preparations of polymeric compounds such as polyesters, polyamino acids, hydrogels, polylactide/glycolide copolymers, ethylenevinylacetate copolymers, polylactic acid, polyglycolic acid, etc., or into liposomes. Such compositions may influence the physical state, stability, rate of in vivo release, and rate of in vivo clearance of components of a pharmaceutical composition of the present invention. See, e.g., Remington: The Science and Practice of Pharmacy, 21st edition, Philadelphia, Pa. Lippincott Williams & Wilkins. The pharmaceutical composition of the present invention can be prepared, for example, in liquid form, or can be in dried powder form (e.g., lyophilized for later reconstitution).

As used herein, "pharmaceutically acceptable carrier" includes any and all solvents, dispersion media and the like which may be appropriate for the desired route of administration of the pharmaceutical preparation, as exemplified in the preceding paragraph. The use of such media for pharmaceutically active substances is known in the art. Except insofar as any conventional media or agent is incompatible with the molecules to be administered, its use in the pharmaceutical preparation is contemplated.

Selection of a suitable pharmaceutical preparation depends upon the method of administration chosen. For example, the molecules of the invention may be administered by intravenous injection. In this instance, a pharmaceutical preparation comprises the molecules dispersed in a medium that is compatible with blood. Pharmaceutical preparations for intravenous injection are known in the art. Steps should be taken to ensure that sufficient amounts of the molecules reach their target cells to exert a biological effect.

Pharmaceutical compositions containing the molecules of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous. Injectable suspensions may be prepared, in which case appropriate liquid carriers, suspending agents and the like may be employed.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. Dosage units may be proportionately increased or decreased based on the weight of the patient. Appropriate concentrations for alleviation of a particular pathological condition may be determined by dosage concentration curve calculations, as known in the art. The appropriate dosage unit for the administration of the molecules of the instant invention may be determined by evaluating the toxicity of the molecules in animal models. Various concentrations of pharmaceutical preparations may be administered to mice with transplanted human tumors, and the minimal and maximal dosages may be determined based on the results of significant reduction of tumor size and side effects as a result of the treatment. Appropriate dosage unit may also be determined by assessing the efficacy of the treatment in combination with other standard therapies.

The pharmaceutical preparation comprising the molecules of the instant invention may be administered at appropriate intervals, for example, at least twice a day or more until the pathological symptoms are reduced or alleviated, after which the dosage may be reduced to a maintenance level. The appropriate interval in a particular case would normally depend on the condition of the patient.

Definitions

The singular forms "a," "an," and "the" include plural referents unless the context clearly dictates otherwise.

As used herein, the term "promoter" refers to a polynucleotide sequence that is located upstream or 5' to the transcription start site and that is involved in the recognition and binding of RNA polymerase II and trans-acting transcription factors to initiate transcription. Typically, a promoter is a 5' regulatory element for modulating transcription and expression of a particular gene or genes operably associated or linked thereto.

A "locus control region" is a long-range cis-acting regulatory element that confers high level of expression of linked genes. A locus control region is a segment of DNA that controls, in part, the chromatin structure and thus the transcription of a gene cluster.

The term "specifically binds" refers to the binding of a polypeptide or compound of interest to a target (e.g., a polypeptide, polynucleotide, or compound) while not substantially recognizing and binding other molecules in a sample containing a mixed population of biological molecules. For example, a DNA binding domain of the instant invention may specifically bind to a particular nucleotide sequence to the general exclusion of other nucleotide sequences in the genome.

The phrase "affinity tag" may refer to tags that can be used to effect the detection and/or purification of a protein of interest. Affinity tags (inclusive of purification tags and epitope tags) are well known in the art (see Sambrook et al., Molecular Cloning, Cold Spring Harbor Laboratory) and include, but are not limited to: polyhistidine tags (e.g. 6×His), polyarginine tags, glutathione-S-transferase (GST), maltose binding protein (MBP), S-tag, influenza virus HA tag, thioredoxin, staphylococcal protein A tag, the FLAG™ epitope, AviTag™ epitope (for subsequent biotinylation), dihydrofolate reductase (DHFR), an antibody epitope (e.g., a sequence of amino acids recognized and bound by an antibody), the c-myc epitope, and heme binding peptides.

As used herein, the term "nuclear localization sequence" refers to an amino sequence allowing the attached polypeptide to be localized or transported to the cell nucleus.

A "vector" is a nucleic acid molecule such as a plasmid, cosmid, bacmid, phage, or virus, to which another genetic sequence or element (either DNA or RNA) may be attached/inserted so as to bring about the replication and/or expression of the sequence or element.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. An isolated nucleic acid (either DNA or RNA) may further represent a molecule produced directly by biological or synthetic means and separated from other components present during its production.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween 80, Polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in Remington: The Science and Practice of Pharmacy, (Lippincott, Williams and Wilkins); Liberman, et al., Eds., Pharmaceutical Dosage Forms, Marcel Decker, New York, N.Y.; and Rowe, et al., Eds., Handbook of Pharmaceutical Excipients, Pharmaceutical Pr.

As used herein, the term "prevent" refers to the prophylactic treatment of a subject who is at risk of developing a condition resulting in a decrease in the probability that the subject will develop the condition.

The term "treat" as used herein refers to any type of treatment that imparts a benefit to a patient afflicted with a disease, including improvement in the condition of the patient (e.g., in one or more symptoms), delay in the progression of the condition, etc.

As used herein, the terms "host," "subject," and "patient" refer to any animal, including humans.

The following examples are provided to illustrate various embodiments of the present invention. They are not intended to limit the invention in any way.

Example 1

The molecular mechanisms that establish and maintain chromatin loops remain incompletely understood. Fundamental insights into these issues arose from studies of the mammalian β-globin locus, which is among the first gene clusters at which long-range chromosomal interactions between a powerful distal enhancer, the locus control region (LCR), and the target β-globin promoters were described (Carter et al. (2002) Nat. Genet., 32:623-626; Tolhuis et al. (2002) Mol. Cell., 10:1453-1465). Mechanistic studies defined gene-specific transcription factors that establish LCR-β-globin interactions, including the hematopoietic-restricted factors GATA1 and its cofactor FOG1 (Vakoc et al. (2005) Mol. Cell., 17:453-462), KLF1 (also known as EKLF) (Drissen et al. (2004) Genes Dev., 18:2485-2490), and the more broadly expressed protein Ldb1 (Song et al. (2007) Mol. Cell., 28:810-822). Functional disruption of any of these factors was associated with reduced LCR-β-globin interactions and diminished β-globin transcription. However, physical interactions among all of these proteins have been reported (Cantor et al. (2002) Oncogene 21:3368-3376), making it difficult to distinguish whether they function in linear or parallel pathways. Moreover, whether loss of looping underlies the loss of transcription or vice versa remains an open question in these studies.

GATA1 is a zinc finger DNA binding protein essential for normal erythroid differentiation and β-globin gene expression (Evans et al. (1989) Cell 58:877-885; Pevny et al. (1991) Nature 349:257-260; Tsai et al. (1989) Nature 339: 446-451). GATA elements are present at the β-globin promoter and LCR, suggesting that GATA1 and its co-factors are involved in the juxtaposition of these sites. The understanding of the mechanisms of GATA1 function has been greatly aided by the use of the GATA1 null proerythroblast cell line G1E. Introduction of an estradiol-inducible version of GATA1 (GATA1-ER) into these cells (G1E-ER4) leads to an estradiol-dependent activation of β-globin gene transcription with concomitant LCR-β-globin looping (Vakoc et al. (2005) Mol. Cell., 17:453-462). The transcription cofactor Ldb1 (also called NLI) does not bind DNA directly but is recruited to E-box elements or GATA elements via a multicomponent complex that includes the TAL1, LMO2, E2A and GATA1. GATA1 and Ldb1 display a highly overlapping genomic occupancy pattern but notably, Ldb1 association strongly favors sites at which GATA1 functions as a transcriptional activator, such as the β-globin locus (Cheng et al. (2009) Genome Res., 19:2172-2184; Kassouf et al. (2010) Genome Res., 20:1064-1083; Soler et al. (2010) Genes Dev., 24:277-289; Tripic et al. (2009) Blood 113:2191-2201; Wu et al. (2011) Genome Res., 21:1659-1671). Several observations suggest that Ldb1 might be a critical effector of GATA1's looping function. First, knockdown of Ldb1 impairs LCR-β-globin looping (Song et al. (2007) Mol. Cell., 28:810-822). Second, the Drosophila homolog of Ldb1, Chip, is required for long-range enhancer action (Morcillo et al. (1997) Genes Dev., 11:2729-2740). Third, like GATA1, Ldb1 co-occupies the β-globin promoter and LCR and might therefore function by physically linking the two (Song et al. (2007) Mol. Cell., 28:810-822; Tripic et al. (2009) Blood 113:2191-2201). Fourth, Ldb1 can form homodimers and even higher order oligomers (Cross et al. (2010) J. Mol. Biol., 399:133-144; Jurata et al. (1997) Mol. Cell. Biol., 17:5688-5698), which might underlie its role in loop formation.

Prior studies in prokaryotes as well as in eukaryotic cells using plasmid constructs have succeeded in influencing gene expression through forced looping among regulatory elements (Marenduzzo et al. (2007) Trends Genet., 23:126-133; Ameres et al. (2005) EMBO J., 24:358-367; Mahmoudi et al. (2002) EMBO J., 21:1775-1781; Nolis et al. (2009) Proc. Natl. Acad. Sci., 106:20222-20227; Petrascheck et al. (2005) Nucleic Acids Res., 33:3743-3750). However, the use of plasmids with altered chromatin configuration and the relatively short genomic distances might limit inferences with regard to long-range chromatin interactions at native gene loci. Herein, a strategy to modulate chromatin looping at an endogenous locus in its native environment was developed. This allowed for the determination whether forced chromatin looping can activate transcription, the examination of the hierarchy of transcriptional regulators in chromatin looping, and defining the ensuing molecular and functional consequences. For the instant studies, G1E erythroid cells were used since they lack transcription factor GATA1 and thus fail to establish an LCR-β-globin loop and transcribe β-globin. Ldb1 recruitment to the β-globin promoter is entirely GATA1 dependent, whereas substantial amounts of the Tal1/Ldb1 complex remain associated with LCR in the absence of GATA1 (FIG. 1; Tripic et al. (2009) Blood 113:2191-2201). Therefore, Ldb1 recruitment by GATA1 to the promoter might represent a critical rate-limiting step in juxtaposing the LCR with the promoter to form a loop required for transcription initiation (FIG. 2A). This hypothesis was tested by using a zinc finger (ZF) targeting approach to tether Ldb1 to the β-globin promoter in G1E cells (FIG. 2A). Notably, promoter bound ZF-Ldb1 was capable of inducing a chromatin loop in G1E cells to an extent similar to that achieved by GATA1 restoration. ZF-Ldb1 constructs completely restored RNA polymerase II (Pol II) recruitment and Pol II serine 5 phosphorylation (Ser5ph), and partially rescued β-globin transcription. Genetic experiments in erythroid cells heterozygous for a deletion of the LCR confirmed that the ZF-Ldb1 proteins functioned via a long-range looping mechanism. These results reveal that forced juxtaposition of regulatory regions can activate transcription and establish Ldb1 as a critical rate-limiting effector of GATA1 during chromatin looping.

Experimental Procedures
Artificial Zinc Finger Design

ZFs each containing six Cys2-His2 zinc finger domains and targeting 18-19 bp sites within either the β-major promoter or DNase1 hypersensitive site 2 of the mouse LCR were designed and assembled from two-finger units as previously described (Bartsevich et al. (2003) Stem Cells 21:632-637).

Cell Culture

G1E and G1E-ER4 cells were cultured as described (Weiss et al. (1997) Mol. Cell. Biol., 17:1642-1651). Where indicated, G1E-ER4 cells were treated with 100 nM estradiol (E2) for 21 hours (3C assays) or 24 hours (RT-qPCR and ChIP assays) to activate GATA1-ER (indicated as G1E+ GATA1 in figures).

Isolation of Primary Erythroblasts

Wild type fetal liver erythroid cells were obtained from CD1 mice (Charles River Laboratories). ΔLCR/ΔLCR mice (129 strain) were described (Bender et al. (2000) Mol. Cell 5:387-393). To generate ΔLCR/wt mice, ΔLCR/ΔLCR male animals were bred with wild type female mice (BL6 strain). E13.5 fetal liver cells were harvested, stained with PE-conjugated anti-CD71 and APC-conjugated anti-Ter119 antibodies and sorted by FACS. The R1 (Ter119–, CD71–/low) populations were isolated, infected with desired retrovirus and cultured for 24 hours in proliferation medium containing Iscove's DMDM supplemented with 15% fetal bovine serum, 1% penicillin-streptomycin, 1% glutamine, 10 ng/mL mIL3, 20 ng/mL m/h IL6, 50 ng/mL mSCF, and 10 ng/mL m/h FLT3L from Peprotech. Where indicated, cells were induced to differentiate by cultured in Iscove's DMDM supplemented with 15% fetal bovine serum, 1% penicillin-streptomycin, 1% glutamine, 50 ug/mL ascorbic acid, 200 ug/mL holotransferrin (Sigma), and 2 U/mL Erythropoietin ALFA (Epogen).

3C Assay

The 3C assay was performed as described (Jing et al. (2008) Mol. Cell., 29:232-242; Vakoc et al. (2005) Mol. Cell., 17:453-462) with the following modifications. $1 \times 10^7$ cells were crosslinked with 1.5% formaldehyde at room temperature for 10 minutes, followed by glycine quenching, cell lysis, Bgl II digestion and T4 ligation. 3C ligation products were quantified in triplicates by quantitative TaqMan® real-time PCR. Probes and primers were designed using Primer Express® 2.0 software (Applied Biosystems) and tested by serial dilution and gel electrophoresis to ensure specific and linear amplification (FIGS. 3B, 3C). Digestion efficiencies were monitored by Sybr® Green qPCR with primer pairs that amplify genomic regions containing or devoid of BglII digestion sites (FIG. 3D). A BAC clone containing the entire murine β-globin locus of 129 origin (SourceBioscience, Clone # BMQ433110) was digested with BglII and re-ligated to generate random ligation products of BglII fragments (FIG. 3A). The DNA was serially diluted and used to generate a standard curve to which all 3C products were normalized. The 3C signals at the β-globin locus were further normalized to those from four intervening regions or, alternatively that of a control locus ERCC3, both producing similar results.

Chromatin Immunoprecipitation

ChIP was performed as described (Tripic et al. (2009) Blood 113:2191-2201). The following antibodies were used: pan-Pol II (sc-899, Santa Cruz), CDK9 (sc-484, Santa Cruz), Ser5ph (MS-134R, Covance), H3K4me3 (07-473, Millipore), anti-HA monoclonal antibody was clone 12CA5. ChIP qPCR primer sequences are listed in the supplement.

RT-qPCR

RNA was extracted with Trizol (Invitrogen) from 10⁵-10⁶ cells. RNase-free glycogen (Invitrogen) was added to aid RNA precipitation. Reverse transcription reactions were performed with random hexamers using Superscript® II (Invitrogen). cDNA samples were quantified by Sybr® Green qPCR. Allele-specific qPCR was carried out at annealing temperature 62° C. (60° C. for conventional qPCR as default setting). Data were normalized to β-actin or GAPDH, both producing similar results.

Retroviral Infections

Retroviral infections of G1E cells were carried out as described (Tripic et al. (2009) Blood 113:2191-2201). For isolated primary fetal liver cells, spin-infection condition was modified to 2,000 rpm at room temperature for 1 hour, and cells were switched to fresh medium immediately after infection.

Plasmids

Individual zinc finger protein coding sequences were cloned into MigR1 retroviral vector with three HA tags and a nuclear localization signal (NLS) at their N-termini. Full length Ldb1 or the SA domain containing amino acids 1-200 of Ldb1 was cloned in frame C-terminal to the ZF. P-ΔSA was generated by deleting the first 256 amino acids of Ldb1.

```
ChIP qPCR primers
HS3
Forward
                                          (SEQ ID NO: 3)
5'-CTAGGGACTGAGAGAGGCTGCTT-3'

Reverse
                                          (SEQ ID NO: 4)
5'-ATGGGACCTCTGATAGACACATCTT-3'

HS2
Forward
                                          (SEQ ID NO: 5)
5'-GGGTGTGTGGCCAGATGTTT-3'

Reverse
                                          (SEQ ID NO: 6)
5'-CACCTTCCCTGTGGACTTCCT-3'

HS1
Forward
                                          (SEQ ID NO: 7)
5'-CAGATCCTCAAACACTCTCCCATAA-3'

Reverse
                                          (SEQ ID NO: 8)
5'-TGCCTTCTTTGTCCCATCATT-3'

εy promoter
Forward
                                          (SEQ ID NO: 9)
5'-ATGACCTGGCTCCACCCAT-3'

Reverse
                                          (SEQ ID NO: 10)
5'-TCTTTGAAGCCATTGGTCAGC-3'

βh1 promoter
Forward
                                          (SEQ ID NO: 11)
5'-AGGTCCAGGGTGAAGAATAAAAGG-3'

Reverse
                                          (SEQ ID NO: 12)
5'-ATCTCAAGTGTGCAAAAGCCAGA-3'

βmaj promoter
Forward
                                          (SEQ ID NO: 13)
5'-CAGGGAGAAATATGCTTGTCATCA-3'

Reverse
                                          (SEQ ID NO: 14)
5'-GTGAGCAGATTGGCCCTTACC-3'

βmaj exon 2
Forward
                                          (SEQ ID NO: 15)
5'-AACGATGGCCTGAATCACTTG-3'

Reverse
                                          (SEQ ID NO: 16)
5'-AGCCTGAAGTTCTCAGGATCC-3'

βmaj intron 2
Forward
                                          (SEQ ID NO: 17)
5'-CTTCTCTCTCTCCTCTCTCTTTCTCTAATC-3'

Reverse
                                          (SEQ ID NO: 18)
5'-AATGAACTGAGGGAAAGGAAAGG-3'

βmaj 3UTR
Forward
                                          (SEQ ID NO: 19)
5'-GCCCTGGCTCACAAGTACCA-3'

Reverse
                                          (SEQ ID NO: 20)
5'-TTCACAGGCAAGAGCAGGAA-3'

βmaj-1kb
Forward
                                          (SEQ ID NO: 21)
5'-GTATGCTCAATTCAAATGTACCTTATT-3'

Reverse
                                          (SEQ ID NO: 22)
5'-TTACCTCTTTATTTCACTTTTACACAT-3'

βmin promoter
Forward
                                          (SEQ ID NO: 23)
5'-GAGCCAGCATTGGGTATATAAAGC-3'

Reverse
                                          (SEQ ID NO: 24)
5'-ACAGACTCAGAAGCAAACGTAAGAAG-3'

IVR16
Forward
                                          (SEQ ID NO: 25)
5'-TGGCCATTTTTACTATGTTAATTTTGC-3'

Reverse
                                          (SEQ ID NO: 26)
5'-TAGACTTGTCATGGTTATGGATTGG-3' mCD4
Forward
                                          (SEQ ID NO: 27)
5'-CCAGAACATTCCGGCACATT-3'

Reverse
                                          (SEQ ID NO: 28)
5'-GGTAAGAGGGACGTGTTCAACTTT-3'

Transcript qPCR primers
βmaj 5 UTR
Forward
                                          (SEQ ID NO: 29)
5'-CAACCCCAGAAACAGACATC-3'

Reverse
                                          (SEQ ID NO: 30)
5'-CAACTTCATCGGCGTTCA-3'

βmaj exon 2
Forward
                                          (SEQ ID NO: 15)
5'-AACGATGGCCTGAATCACTTG-3'
```

Reverse
(SEQ ID NO: 16)
5'-AGCCTGAAGTTCTCAGGATCC-3'

βmaj-D
Forward
(SEQ ID NO: 31)
5'-GCCTGTGGGGAAAGGTGAACT-3'

Reverse
(SEQ ID NO: 32)
5'-CCATCGTTAAAGGCAGTTATCACC-3'

βmaj-S
Forward
(SEQ ID NO: 33)
5'-GCCTGTGGGGAAAGGTGAACG-3'

Reverse
(SEQ ID NO: 34)
5'-GCCATCGTTAAAGGCAGTTATCACT-3'

βmaj intron 2
Forward
(SEQ ID NO: 17)
5'-CTTCTCTCTCTCCTCTCTCTTTCTCTAATC-3'

Reverse
(SEQ ID NO: 18)
5'-AATGAACTGAGGGAAAGGAAAGG-3'

βmaj exon 2/3
Forward
(SEQ ID NO: 35)
5'-AGCTCCACTGTGACAAGCTG-3'

Reverse
(SEQ ID NO: 36)
5'-CCAGCACAATCACGATCATA-3'

βmaj 3UTR
Forward
(SEQ ID NO: 19)
5'-GCCCTGGCTCACAAGTACCA-3'

Reverse
(SEQ ID NO: 20)
5'-TTCACAGGCAAGAGCAGGAA-3'

βh1
Forward
(SEQ ID NO: 37)
5'-AGGCAGCTATCACAAGCATCTG-3'

Reverse
(SEQ ID NO: 38)
5'-AACTTGTCAAAGAATCTCTGAGTCCA-3'

Hba
Forward
(SEQ ID NO: 39)
5'-GTGGATCCCGTCAACTTCAAG-3'

Reverse
(SEQ ID NO: 40)
5'-CAAGGTCACCAGCAGGCAGT-3'

Slc4a1
Forward
(SEQ ID NO: 41)
5'-TGGAGGCCTGATCCGTGATA-3'

Reverse
(SEQ ID NO: 42)
5'-AGCGCATCGGTGATGTCA-3'

Alas2
Forward
(SEQ ID NO: 43)
5'-CCATCTTAAGGCAACCAAGGC-3'

Reverse
(SEQ ID NO: 44)
5'-ACAGCATGAAAGGACAATGGC-3'

Klf1
Forward
(SEQ ID NO: 45)
5'-TTCCGGAGAGGACGATGAGA-3'

Reverse
(SEQ ID NO: 46)
5'-AACCTGGAAAGTTTGTAAGGAAAAGA-3'

Gata1
Forward
(SEQ ID NO: 47)
5'-GCCCAAGAAGCGAATGATTG-3'

Reverse
(SEQ ID NO: 48)
5'-GTGGTCGTTTGACAGTTAGTGCAT-3'

Gata2
Forward
(SEQ ID NO: 49)
5'-CACCCCTAAGCAGAGAAGCAA-3'

Reverse
(SEQ ID NO: 50)
5'-TGGCACCACAGTTGACACACT-3'

Kit
Forward
(SEQ ID NO: 51)
5'-AGCAGATCTCGGACAGCACC-3'

Reverse
(SEQ ID NO: 52)
5'-TGCAGTTTGCCAAGTTGGAG-3'

Gapdh
Forward
(SEQ ID NO: 53)
5'-GATGCCCCCATGTTTGTGAT-3'

Reverse
(SEQ ID NO: 54)
5'-GGTCATGAGCCCTTCCACAAT-3'

β-actin
Forward
(SEQ ID NO: 55)
5'-ACACCCGCCACCAGTTC-3'

Reverse
(SEQ ID NO: 56)
5'-TACAGCCCGGGGAGCAT-3'

3C probes and primers
β-globin locus (from top to bottom are SED ID NOs: 57-69)
LCR-H52 probe
5'-FAM/TCT GCC TGT CCC TGC CTC GTG A/3'-TAMSp Anchor (rHS2)
5'-CAGCGTTTTAGTTGGATATAGAGTGAA-3'

I (rHS1)
5'-GAACTTGTCAGGGAATTACCTAGTACAG-3'

II (rβh1εy)
5'-GATCCCTATTGTCTACTTTTGCCAG-3'

III (βh1)
5'-CCCATGTTACACCCCATTACAAG-3'

IV (βmaj)
5'-GGCTGGAACATCACTGGAATAAAT-3'

V (βmaj-frag2)
5'-CAGTCGAGGAATGCAACTGTGA-3'

-continued

VI (rIVR3)
5'-AAGACTAAAAATCCCAGATTGATTCC-3'

VII (rβmin)
5'-GCCAAATCAGGACCCTAACATT-3'

VIII (rIVR2)
5'-CCAAGTCTCTCAAGAAAGAAATCGA-3'

X (rIVR1)
5'-CAAACATAAGACCATAAGCAACAGAAA-3'

XI (r3HS1)
5'-ACTACCTAACTCTCAAAAATCTGTGTGA-3'

XII (r3OR)
5'-GAAAAAATGTGTACGCATCATTAGTTATG-3'

ERCC3 locus (from top to bottom are SED ID NOs: 70-72)
ERCC3 probe
5'-FAM/TCTAGAGCCAAACTCTCCAGCCACCACTTC/3'-TAMSp rERCC3_3
5'-GCAGTGAAAACACAACACAGTTAATATG-3' rERCC3_5
5'-GCAGCCACCGACTTGGAT-3'

Primers for 3C digestion efficiency
HS2 BglII cut #1
Forward
(SEQ ID NO: 73)
5'-TGTAGATCAGGATTGACTGGTAC-3'

Reverse
(SEQ ID NO: 74)
5'-CAGCGTTTTAGTTGGATATAGAGTGAA-3'

HS2 BglII uncut #1
Forward
(SEQ ID NO: 75)
5'-GGGTGTGTGGCCAGATGTTT-3'

Reverse
(SEQ ID NO: 76)
5'-CACCTTCCCTGTGGACTTCCT-3'

HS2 BglII cut #2
Forward
(SEQ ID NO: 77)
5'-GCGTTTTAGTTGGATATAGAGTGAAGG-3'

Reverse
(SEQ ID NO: 78)
5'-TGCTATCATGGAACATACTATGTAGATCA-3'

HS2 BglII uncut #2
Forward
(SEQ ID NO: 79)
5'-AGGAACAGGCAAGGCAGCTT-3'

Reverse
(SEQ ID NO: 80)
5'-TCACTGGTACCCTGTTTCCTTATCT-3'

Results
Zinc Finger-Mediated Targeting of Ldb1 to the Endogenous β-Globin Locus

Figure 1C:
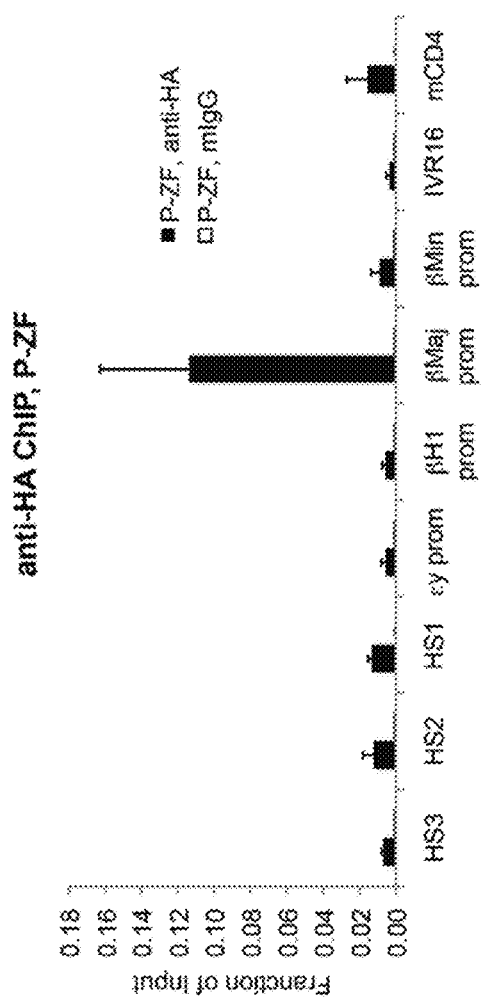
Figure 1D:
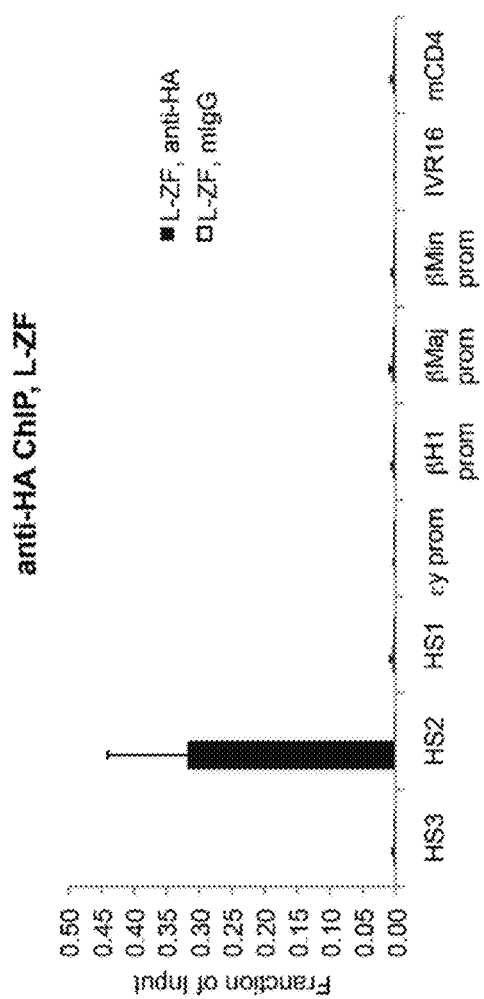

As a strategy to tether potential looping factors to the endogenous β-globin locus, artificial zinc finger proteins (ZF) were chosen since they have been used successfully to target preselected genomic sites in vivo (Klug, A. (2010) Annu. Rev. Biochem., 79:213-231). ZFs were synthesized to target the β-major promoter (P-ZF) and DNase1 hypersensitive site 2 (HS2) of the LCR (L-ZF) (FIG. 2B) as these sites were previously found to be in close physical proximity (Carter et al. (2002) Nat. Genet., 32:623-626; Tolhuis et al. (2002) Mol. Cell., 10:1453-1465). Six zinc fingers were linked in tandem to target 18 base pairs of genomic sequence (Klug, A. (2010) Annu. Rev. Biochem., 79:213-231). Target sequences were chosen within the DNase I hypersensitive regions to facilitate access to the ZFs but avoid interference with known transcription factor binding sites (FIG. 1B). Binding of the ZFs to their designated DNA sequences was characterized using a previously described ELISA-based assay (Bartsevich et al. (2003) Stem Cells 21:632-637). ZFs were fused to an HA tag and a nuclear localization sequence (NLS), and their chromatin binding profiles were examined by chromatin immunoprecipitation (ChIP) following introduction into G1E cells (FIGS. 1C, 1D). ZFs with suitable binding properties were fused to Ldb1, and introduced into a retroviral vector containing an IRES-GFP or IRESYFP cassette. Upon infection of G1E cells, populations of GFP/YFP positive cells were purified by fluorescence activated cell sorting (FACS) and subjected to anti-HA ChIP. A P-ZF was identified that strongly bound the β-globin promoter in G1E cells (FIG. 1C). Fusion of Ldb1 with P-ZF (P-Ldb1) retained strong binding to the β-globin promoter but was also detectable at low levels at multiple HSs of the LCR (FIG. 2B). In the absence of the Ldb1 moiety, this ZF bound to these LCR sites with lower efficiency (FIG. 1C), indicating that the association of P-Ldb1 with the LCR is in large part due to its interaction with endogenous Ldb1 complexes at the LCR (Tripic et al. (2009) Blood 113:2191-2201). In addition, L-Ldb1 (L-ZF fused to Ldb1) was found to bind to HS2 but not the β-globin promoter (FIG. 2C), consistent with the lack of endogenous Ldb1 complexes in the absence of GATA1 (FIG. 1A). Finally, cells co-expressing L-Ldb1 and P-Ldb1 produced comparable ChIP signals at the LCR and β-major promoter (FIG. 2D). It is noteworthy that ChIP results comparing several ZF proteins in erythroblasts and fibroblasts revealed that the binding properties of ZFs to naked DNA sequences in vitro do not fully predict their binding efficiency in vivo. Nevertheless, a ZF pair capable of targeting Ldb1 to the β-globin locus was identified.

Tethering Ldb1 to the β-Globin Locus Activates Transcription in the Absence of GATA1

LCR-promoter looping is required for high-level globin gene expression throughout erythroid development. Therefore, it was examined whether promoter- and/or LCR-tethered Ldb1 induces β-globin transcription in G1E cells. Since G1E cells lack GATA1, the β-globin promoter is devoid of Ldb1 whereas the LCR retains significant amounts of Ldb1 mediated by the TAL1 complex bound to E-box elements (FIGS. 1A, 2A). Remarkably, expression of P-Ldb1 activated β-globin transcription over a thousand-fold (FIG. 4A) amounting to approximately 20% of that achieved upon restoration of GATA1 (G1E-ER4 cells) (FIG. 4B). L-Ldb1 alone or ZFs without the Ldb1 moiety displayed little activity (FIG. 4A). Co-expression of P-Ldb1 and L-Ldb1 failed to further activate β-globin expression compared to P-Ldb1 by itself (FIG. 4A). Because high level β-globin expression requires the LCR (Bender et al. (2000) Mol. Cell., 5:387-393), these results indicate that promoter-bound Ldb1 is sufficient to promote long-range contacts with at the LCR, presumably via endogenous Ldb1, to activate transcription. Measurements of β-globin expression were confirmed with multiple primer pairs directed against the β-globin transcript (FIG. 5A). Moreover, the effects of ZF-Ldb1 expression were gene-specific and not simply a consequence of a general differentiation induction since the expression of several additional GATA1 activated (Klf1, Eraf, βH1) and repressed (Gata2, Kit) genes was unchanged (FIG. 4C). The potent activation by ZF-Ldb1 fusion proteins of β-globin transcription is particularly remarkable since it occurred in the absence of GATA1, which is essential for β-globin transcription.

The substantial β-globin transcriptional activation by ZF-Ldb1 strongly implicates an LCR looping mechanism since β-globin transcription is reduced to ~1% of normal when the LCR is deleted (Bender et al. (2000) Mol. Cell., 5:387-393). Moreover, Ldb1 occupancy at the β-globin promoter is normal in the absence of the LCR (Song et al. (2010) Blood 116:2356-64), indicating that promoter-bound Ldb1 alone is insufficient for β-globin transcription without the LCR. Although β-globin activation by ZF-Ldb1 fusion proteins was substantial, their effects did not match those of GATA1, consistent with GATA1 exerting functions in addition to chromatin looping.

Tethering of the Ldb1 Self-Association Domain is Sufficient for β-Globin Activation Ldb1 contains an N-terminal self-association (SA) domain that mediates the assembly of higher order molecular complexes and might account for its looping function (Xu et al. (2003) Mol. Cell. Biol., 23:7585-7599; Cross et al. (2010) J. Mol. Biol., 399:133-144), and a C-terminal LIM interaction domain (LID) that confers binding to LMO2 and its associated GATA1/TAL1/E2A multi-protein complex. To examine whether the SA domain is sufficient for transcription activation, it was fused with L-ZF and P-ZF and introduced into G1E cells. P-SA and L-SA showed very similar genomic binding profiles as the full-length Ldb1 fusion constructs such that L-SA occupied HS2 whereas P-SA bound the β-globin promoter and additionally the LCR (FIG. 5B). Remarkably, expression of P-SA alone or co-expression of L-SA and P-SA activated β-globin gene transcription to virtually the same level as did the full-length Ldb1 fusion proteins (FIGS. 4D, 5C). Again, the effects of ZF-SA were gene-specific and did not globally alter erythroid gene expression (FIG. 5C). These results indicate that the Ldb1 self-association domain is sufficient to induce β-globin transcription, further supporting the idea that forced juxtaposition between the LCR and β-globin promoter underlies transcriptional activation.

The possibility that the remaining portions of Ldb1 might participate in chromatin looping by nucleating higher order protein complexes was also considered. To this end, a ZF-Ldb1 fusion protein lacking the SA domain (P-ΔSA) but leaving the nuclear localization sequence and LID domain intact was generated. P-ΔSA was capable of inducing β-globin transcription albeit to a significantly lower degree than P-SA (FIG. 5D). Activation never exceeded 50% of that observed with P-SA even under the most optimal conditions and expression levels (FIG. 5D). This demonstrates that the SA domain is most efficient in nucleating higher order complexes required for looping. Nevertheless, these results are also consistent with the possibility that Ldb1 can engage its partner proteins via distinct domains to produce chromatin loops.

Tethering of the Ldb1 Self-Association Domain Induces LCR Promoter Looping

Figure 6D:
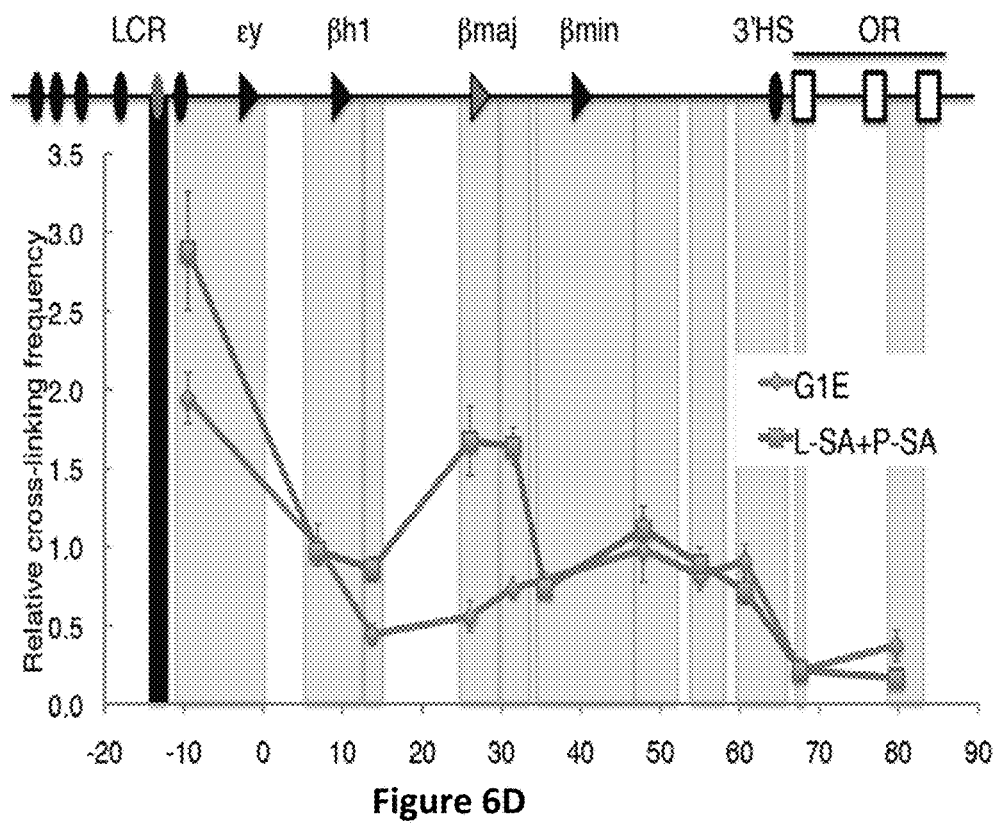

The strong induction of β-globin transcription by ZF-Ldb1 or ZF-SA implicates an involvement of the LCR and hence chromatin looping, since in the absence of the LCR β-globin transcription is very low (Bender et al. (2000) Mol. Cell., 5:387-393). Therefore, it was examined by 3C assay whether expression of ZF-SA constructs juxtaposed the LCR with the β-globin gene to form a chromatin loop (FIG. 3). Using HS2 as the anchor region, it was found that in parental G1E cells the 3C signals generally declined with increasing distance (FIG. 6A; Vakoc et al. (2005) Mol. Cell., 17:453-462). In particular, there is no interaction between HS2 and β-globin. Upon GATA1 restoration, the relative proximity of HS2 with two adjacent fragments comprising the β-major globin gene significantly increased (FIG. 6A). HS2 interactions with intervening or downstream segments remained low, indicative of a GATA1-dependent HS2-β-globin chromatin loop (Vakoc et al. (2005) Mol. Cell., 17:453-462). The chromatin conformation of the β-globin locus in G1E cells expressing ZF-SA proteins was then determined. Strikingly, expression of P-SA alone but not L-SA produced a strong HS2-β-globin chromatin loop, recapitulating the chromatin conformation induced by GATA1 (FIGS. 6B, 6C). Thus, recruitment of the SA domain to the β-globin promoter is sufficient for juxtaposition with the LCR, likely via interaction with endogenous LCR-bound Ldb1 (FIGS. 1A, 2A, 5B). Co-expression of P-SA and L-SA triggered juxtaposition of HS2 with the β-globin gene with a similar efficiency as the P-SA alone (FIG. 6D). Given the lower levels of occupancy of P-SA at HS2 in comparison to L-SA, it was surprising to find that P-SA was as active as the combination of L-SA plus P-SA or GATA1. It is possible that the ChIP signal for P-SA at the LCR under-represents the amounts of P-SA since proteins indirectly associated with DNA are not cross-linked as efficiently. Moreover, P-SA association with multiple regions in the LCR via endogenous Ldb1 likely adds to its ability to promote loop formation. Nevertheless, forced LCR-β-globin chromatin looping correlated well with activation of β-globin transcription. In concert, these results show that tethering the SA domain of Ldb1 to the β-globin promoter is sufficient to produce an LCR-β-globin chromatin loop that is similar if not identical to that generated by GATA1. This indicates that Ldb1 is an essential rate-limiting effector of GATA1 during chromatin looping. More generally, juxtaposition of an LCR with a promoter causes strong gene activation.

ZF-SA Expression Produces LCR-Dependent Functions

Two of the key functions of the β-globin LCR functions are the recruitment of Pol II to the β-globin promoter and stimulation of Pol II phosphorylation at serine 5 of its C-terminal domain, a modification associated with early transcription elongation (Sawado et al. (2003) Genes Dev., 17:1009-1018). Hence, if ZF-SA proteins activate β-globin transcription by promoting LCR-β-globin contacts, they are expected to stimulate Pol II recruitment and serine 5 phosphorylation (Ser5ph). To examine the extent to which ZF-SA fusion protein restored LCR-dependent function, ChIP with antibodies against Ser5ph Pol II was performed, or antibodies that react with Pol II regardless of its phosphorylation state. Notably, expression of P-SA triggered Pol II recruitment to the β-globin promoter with an efficiency similar to that achieved by GATA1 expression (FIGS. 7A, 7B). In contrast, Pol II levels in the body of the gene amounted to approximately 25% to 30% of those found in GATA1 expressing cells corresponding well with the levels of β-globin mRNA production (FIG. 4B). This is consistent with reduced recruitment of the elongation complex P-TEFb to the β-globin promoter and the body of the gene when compared to GATA1 expressing cells (as measured by anti-CDK9 ChIP, FIG. 8A). The amounts of Ser5ph Pol II found at the β-globin gene in P-SA expressing cells were indistinguishable from those observed in GATA1-expressing cells (FIG. 7C). As an additional measure of transcription initiation, the level of histone H3 lysine 4 trimethylation (H3K4me3) was determined and it was found that P-SA restored this mark to levels equal to that produced by GATA1 (FIG. 8B). Similar results were obtained in cells co-expressing P-SA and LSA. These results demonstrate that two functions of the LCR, i.e. Pol II recruitment to the β-globin promoter and Pol II serine 5 phosphorylation were completely restored by expression of P-SA, lending additional support to the idea that juxtaposition of the LCR with the β-globin promoter underlies the activity of P-SA. The failure to fully restore transcription elongation can be explained by the lack of GATA1 and its co-factors which exert additional, looping-independent functions, possibly including the recruitment and activation of P-TEFb complex (Bottardi et al. (2011) Nucleic Acids Res., 39:3505-3519; Elagib et al. (2008) Blood 112:4884-4894).

Precocious Induction of β-Globin Transcription by ZF-SA Fusion Proteins in Primary Erythroblasts It was examined whether ZF fusion proteins function in primary erythroid progenitor cells to activate β-globin expression. The maturation stage of primary erythroid precursor cells from E13.5 wild type fetal livers was monitored by flow cytometry measuring the expression of the cell surface markers Ter119 and CD71 (Zhang et al. (2003) Blood 102:3938-3946). Cells progress through the R1, R2, R3, and R4 stages of maturation (FIG. 9A), and ultimately produce abundant amounts of β-globin (FIG. 10A). For the expression of ZF-SA proteins, Ter119$^-$, CD71$^{-/low}$ cells (R1 population in FIG. 9A) were purified, representing early precursor cells. At this stage, the β-globin genes are not yet highly active but cells express low levels of essential regulatory factors, including GATA1 and KLF1 (FIG. 10B). Following infection with retrovirus expressing ZF-SA fusion proteins, cells were cultured in defined medium containing cytokines IL-3, IL6 and SCF to preserve the cells in the precursor state. Remarkably, expression of P-SA only or P-SA/L-SA, but not L-SA alone precociously activated β-globin transcription (FIG. 9B). Note that the fold-activation over control was not as pronounced as that observed in the G1E system, since in contrast to the latter, primary erythroblasts are replete with transcription factors and produce higher levels of β-globin even prior to full maturation. Nonetheless, these results in essence mirrored those from G1E cells in that the same combinations of ZF fusion proteins were capable of activating β-globin expression. The effects were specific to the β-globin locus as no other erythroid genes examined were altered in their activities (FIG. 9B). Moreover, ZF-SA expression did not non-specifically promote erythroid maturation as determined by flow cytometry using CD71 and Ter119 surface markers (FIG. 10C). Together, these results show that ZF-SA fusion constructs can activate β-globin transcription in primary erythroid cells.

ZF-SA Fusion Protein Induction of β-Globin Transcription is LCR-Dependent

Targeting of the SA domain to the β-globin locus restores juxtaposition of HS2 with the β-globin gene, Pol II recruitment, and Pol II serine 5 phosphorylation, strongly suggesting that transcriptional activation is due to LCR-β-globin looping. The prediction from these observations is that alleles lacking the LCR would not respond to ZF-SA fusion proteins (FIG. 11A). Alternatively, if β-globin transcription simply resulted from SA-induced transcription factor assembly at the β-globin promoter, ZF-SA should activate transcription independently of the LCR. This distinction is especially important in light of the positive effects on β-globin transcription exerted by the expression of P-SA alone. To definitively distinguish between these possibilities, ZF-SA's functions were examined in E13.5 fetal liver erythroblasts derived from mice that are heterozygous for a deletion of the LCR (ΔLCR/+) (Bender et al. (2000) Mol. Cell., 5:387-393). The β-major gene on the ΔLCR allele is of the D haplotype whereas that on the wild type allele is of the S haplotype. An allele-specific qPCR assay was developed that distinguishes single nucleotide polymorphisms between the transcripts of these alleles (FIG. 12), providing an ideal internally controlled experimental setup. Next ΔLCR/+R1 cells were transduced with viral vectors expressing ZF-SA proteins and exposed them to erythropoietin for 6 hours to promote erythroid maturation. Allele-specific RT-qPCR demonstrated that the wild type allele (βmaj-S) was activated in cells expressing L-SA together with P-SA, or P-SA alone (FIG. 11B, left panel). L-SA had little or no activity similar to ZFs lacking SA that served as negative controls. In striking contrast, the β-major gene on ΔLCR allele (βmaj-D) was expressed at low levels and showed very little response to the P-SA/L-SA or P-SA proteins (FIG. 11B, middle panel). The effects of ZF fusion protein expression were the essentially the same in the presence or absence of erythropoietin and specific to the β-globin locus as none of the other examined erythroid genes were altered in their activities (FIG. 13). The residual signal produced by the D-allele-specific primers was not due to transcription from the D-allele but the result of cross-hybridization with S-allele cDNA. This was demonstrated by template mixing experiments showing that approximately 10% of the signal produced by the D-allele-specific primers derived from cross-reactivity with the S-allele cDNA (FIG. 12). Indeed, when homozygous (ΔLCR/ΔLCR) R1 cells were transduced with PSA, β-globin activation was close to background, establishing that the low signal obtained with D-specific primers in ΔLCR/wt cells was in fact due to cross-hybridization (FIG. 12B, right panel). In concert, the results clearly demonstrate that the activity of ZF-SA proteins is entirely dependent on the presence of LCR and hence on long-range chromatin looping.

Example 2

Data is shown here that the methods of the instant invention are suitable for the developmental reprogramming of the β-globin locus. Specifically, targeting of a "looping" factor to the embryonic globin (bH1) gene in adult mouse erythroid cells led to substantial activation of embryonic globin gene expression. Indeed, FIG. 16 shows that forcing a LCR-βh1 chromatin loop reactivated the silenced βh1 gene in adult cells. Levels achieved are ~24% of total globin synthesis. This level of expression is therapeutically relevant, thereby indicating that such methods would be useful in the treatment of β-thalassemia and sickle cell disease.

FIG. 17 also shows the results of an experiment in which an artificial zinc finger fused to the looping factor (Ldb1) was targeted to the human fetal (gamma) globin promoter. Primary human erythroid cells expressing the ZF-Ld1 fusion protein (GFP+) display elevated gamma globin production reaching up to ~65% of total globin synthesis.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method of inhibiting a disease or disorder in a subject comprising administering to said subject a composition comprising i) a nucleic acid molecule encoding a polypeptide comprising a DNA binding domain and a looping factor, wherein said looping factor is a fragment of LIM domain binding 1 (Ldb1), and ii) at least one pharmaceutically acceptable carrier,
wherein said fragment of Ldb1 comprises an amino acid sequence having at least 90% identity with amino acids 1 to 200 of SEQ ID NO: 1.

2. The method of claim 1, wherein said disease or disorder is sickle cell anemia or beta-thalassemia and wherein said DNA binding domain specifically binds a target sequence in a globin promoter.

3. The method of claim 2, wherein said DNA binding domain specifically binds a target sequence in the fetal (gamma) gene promoter.

4. The method of claim 1, wherein said DNA binding domain and said looping factor are linked through a covalent bond or an amino acid linker.

5. The method of claim 1, wherein said Ldb1 is human.

6. The method of claim 1, wherein said fragment of Ldb1 comprises amino acids 1 to about 200 of SEQ ID NO: 1.

7. The method of claim 1, wherein said DNA binding domain comprises a zinc finger protein or a transcription activator-like effector protein.

8. The method of claim 1, wherein said DNA binding domain specifically binds a target sequence in the promoter of a gene aberrantly expressed in said disease or disorder.

9. The method of claim 8, wherein said promoter is a globin promoter.

10. The method of claim 1, wherein said looping factor consists of amino acids 1 to 200 of SEQ ID NO: 1.

11. The method of claim 1, wherein said looping factor is an N-terminal fragment of Ldb1, wherein said N-terminal fragment of Ldb1 comprises amino acids 1 to 200 of SEQ ID NO: 1.

12. The method of claim 1, wherein said method comprises administering a first and second nucleic acid molecule,
wherein said first nucleic acid molecule encodes a first polypeptide comprising a first DNA binding domain and a first looping factor, wherein said first looping factor is LIM domain binding 1 (Ldb1) or a fragment thereof, and wherein said first DNA binding domain specifically binds to a target sequence in the promoter of a gene of interest, and
wherein said second nucleic acid molecule encodes a second polypeptide comprising a second DNA binding domain and a second looping factor, wherein said second looping factor is LIM domain binding 1 (Ldb1) or a fragment thereof, and wherein said second DNA binding domain specifically binds to a target sequence in the locus control region of said gene of interest.

\* \* \* \* \*

SEQUENCE LISTING

<160> NUMBER OF SEQ ID NOS: 83

<210> SEQ ID NO 1
<211> LENGTH: 375
<212> TYPE: PRT
<213> ORGANISM: Homo sapiens

<400> SEQUENCE: 1

| | | | | | | | | | | | | | | |
|---|---|---|---|---|---|---|---|---|---|---|---|---|---|---|
| Met | Leu | Asp | Arg | Asp | Val | Gly | Pro | Thr | Pro | Met | Tyr | Pro | Pro | Thr | Tyr |
| 1 | | | | 5 | | | | | 10 | | | | | 15 | |
| Leu | Glu | Pro | Gly | Ile | Gly | Arg | His | Thr | Pro | Tyr | Gly | Asn | Gln | Thr | Asp |
| | | | 20 | | | | | 25 | | | | | 30 | | |
| Tyr | Arg | Ile | Phe | Glu | Leu | Asn | Lys | Arg | Leu | Gln | Asn | Trp | Thr | Glu | Glu |
| | | 35 | | | | | 40 | | | | | 45 | | | |
| Cys | Asp | Asn | Leu | Trp | Trp | Asp | Ala | Phe | Thr | Thr | Glu | Phe | Phe | Glu | Asp |
| 50 | | | | | 55 | | | | | 60 | | | | | |
| Asp | Ala | Met | Leu | Thr | Ile | Thr | Phe | Cys | Leu | Glu | Asp | Gly | Pro | Lys | Arg |
| 65 | | | | | 70 | | | | 75 | | | | | | 80 |
| Tyr | Thr | Ile | Gly | Arg | Thr | Leu | Ile | Pro | Arg | Tyr | Phe | Arg | Ser | Ile | Phe |
| | | | | 85 | | | | | 90 | | | | | 95 | |
| Glu | Gly | Gly | Ala | Thr | Glu | Leu | Tyr | Tyr | Val | Leu | Lys | His | Pro | Lys | Glu |
| | | | 100 | | | | | 105 | | | | | 110 | | |
| Ala | Phe | His | Ser | Asn | Phe | Val | Ser | Leu | Asp | Cys | Asp | Gln | Gly | Ser | Met |
| | | 115 | | | | | 120 | | | | | 125 | | | |
| Val | Thr | Gln | His | Gly | Lys | Pro | Met | Phe | Thr | Gln | Val | Cys | Val | Glu | Gly |
| | 130 | | | | | 135 | | | | | 140 | | | | |
| Arg | Leu | Tyr | Leu | Glu | Phe | Met | Phe | Asp | Asp | Met | Met | Arg | Ile | Lys | Thr |
| 145 | | | | | 150 | | | | | 155 | | | | | 160 |
| Trp | His | Phe | Ser | Ile | Arg | Gln | His | Arg | Glu | Leu | Ile | Pro | Arg | Ser | Ile |
| | | | | 165 | | | | | 170 | | | | | 175 | |
| Leu | Ala | Met | His | Ala | Gln | Asp | Pro | Gln | Met | Leu | Asp | Gln | Leu | Ser | Lys |
| | | | 180 | | | | | 185 | | | | | 190 | | |
| Asn | Ile | Thr | Arg | Cys | Gly | Leu | Ser | Asn | Ser | Thr | Leu | Asn | Tyr | Leu | Arg |
| | | 195 | | | | | 200 | | | | | 205 | | | |
| Leu | Cys | Val | Ile | Leu | Glu | Pro | Met | Gln | Glu | Leu | Met | Ser | Arg | His | Lys |
| | 210 | | | | | 215 | | | | | 220 | | | | |
| Thr | Tyr | Ser | Leu | Ser | Pro | Arg | Asp | Cys | Leu | Lys | Thr | Cys | Leu | Phe | Gln |
| 225 | | | | | 230 | | | | | 235 | | | | | 240 |
| Lys | Trp | Gln | Arg | Met | Val | Ala | Pro | Pro | Ala | Glu | Pro | Thr | Arg | Gln | Gln |
| | | | | 245 | | | | | 250 | | | | | 255 | |
| Pro | Ser | Lys | Arg | Arg | Lys | Arg | Lys | Met | Ser | Gly | Gly | Ser | Thr | Met | Ser |
| | | | 260 | | | | | 265 | | | | | 270 | | |
| Ser | Gly | Gly | Gly | Asn | Thr | Asn | Asn | Ser | Asn | Ser | Lys | Lys | Lys | Ser | Pro |
| | | 275 | | | | | 280 | | | | | 285 | | | |
| Ala | Ser | Thr | Phe | Ala | Leu | Ser | Ser | Gln | Val | Pro | Asp | Val | Met | Val | Val |
| | 290 | | | | | 295 | | | | | 300 | | | | |
| Gly | Glu | Pro | Thr | Leu | Met | Gly | Gly | Glu | Phe | Gly | Asp | Glu | Asp | Glu | Arg |
| 305 | | | | | 310 | | | | | 315 | | | | | 320 |
| Leu | Ile | Thr | Arg | Leu | Glu | Asn | Thr | Gln | Phe | Asp | Ala | Ala | Asn | Gly | Ile |
| | | | | 325 | | | | | 330 | | | | | 335 | |
| Asp | Asp | Glu | Asp | Ser | Phe | Asn | Asn | Ser | Pro | Ala | Leu | Gly | Ala | Asn | Ser |
| | | | 340 | | | | | 345 | | | | | 350 | | |
| Pro | Trp | Asn | Ser | Lys | Pro | Pro | Ser | Ser | Gln | Glu | Ser | Lys | Ser | Glu | Asn |
| | | 355 | | | | | 360 | | | | | 365 | | | |

Pro Thr Ser Gln Ala Ser Gln
    370                 375

<210> SEQ ID NO 2
<211> LENGTH: 411
<212> TYPE: PRT
<213> ORGANISM: Homo sapiens

<400> SEQUENCE: 2

Met Ser Val Gly Cys Ala Cys Pro Gly Cys Ser Ser Lys Ser Phe Lys
1               5                   10                  15

Leu Tyr Ser Pro Lys Glu Pro Pro Asn Gly Asn Ala Phe Pro Pro Phe
            20                  25                  30

His Pro Gly Thr Met Leu Asp Arg Asp Val Gly Pro Thr Pro Met Tyr
        35                  40                  45

Pro Pro Thr Tyr Leu Glu Pro Gly Ile Gly Arg His Thr Pro Tyr Gly
    50                  55                  60

Asn Gln Thr Asp Tyr Arg Ile Phe Glu Leu Asn Lys Arg Leu Gln Asn
65                  70                  75                  80

Trp Thr Glu Glu Cys Asp Asn Leu Trp Trp Asp Ala Phe Thr Thr Glu
                85                  90                  95

Phe Phe Glu Asp Asp Ala Met Leu Thr Ile Thr Phe Cys Leu Glu Asp
            100                 105                 110

Gly Pro Lys Arg Tyr Thr Ile Gly Arg Thr Leu Ile Pro Arg Tyr Phe
        115                 120                 125

Arg Ser Ile Phe Glu Gly Gly Ala Thr Glu Leu Tyr Tyr Val Leu Lys
    130                 135                 140

His Pro Lys Glu Ala Phe His Ser Asn Phe Val Ser Leu Asp Cys Asp
145                 150                 155                 160

Gln Gly Ser Met Val Thr Gln His Gly Lys Pro Met Phe Thr Gln Val
                165                 170                 175

Cys Val Glu Gly Arg Leu Tyr Leu Glu Phe Met Phe Asp Asp Met Met
            180                 185                 190

Arg Ile Lys Thr Trp His Phe Ser Ile Arg Gln His Arg Glu Leu Ile
        195                 200                 205

Pro Arg Ser Ile Leu Ala Met His Ala Gln Asp Pro Gln Met Leu Asp
    210                 215                 220

Gln Leu Ser Lys Asn Ile Thr Arg Cys Gly Leu Ser Asn Ser Thr Leu
225                 230                 235                 240

Asn Tyr Leu Arg Leu Cys Val Ile Leu Glu Pro Met Gln Glu Leu Met
                245                 250                 255

Ser Arg His Lys Thr Tyr Ser Leu Ser Pro Arg Asp Cys Leu Lys Thr
            260                 265                 270

Cys Leu Phe Gln Lys Trp Gln Arg Met Val Ala Pro Pro Ala Glu Pro
        275                 280                 285

Thr Arg Gln Gln Pro Ser Lys Arg Arg Lys Arg Lys Met Ser Gly Gly
    290                 295                 300

Ser Thr Met Ser Ser Gly Gly Gly Asn Thr Asn Asn Ser Asn Ser Lys
305                 310                 315                 320

Lys Lys Ser Pro Ala Ser Thr Phe Ala Leu Ser Ser Gln Val Pro Asp
                325                 330                 335

Val Met Val Val Gly Glu Pro Thr Leu Met Gly Gly Glu Phe Gly Asp
            340                 345                 350

Glu Asp Glu Arg Leu Ile Thr Arg Leu Glu Asn Thr Gln Phe Asp Ala
        355                 360                 365

```
Ala Asn Gly Ile Asp Asp Glu Asp Ser Phe Asn Asn Ser Pro Ala Leu
        370                 375                 380

Gly Ala Asn Ser Pro Trp Asn Ser Lys Pro Pro Ser Ser Gln Glu Ser
385                 390                 395                 400

Lys Ser Glu Asn Pro Thr Ser Gln Ala Ser Gln
                405                 410
```

<210> SEQ ID NO 3
<211> LENGTH: 23
<212> TYPE: DNA
<213> ORGANISM: Artificial Sequence
<220> FEATURE:
<223> OTHER INFORMATION: Primer

<400> SEQUENCE: 3
ctagggactg agagaggctg ctt                                           23

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
atgggacctc tgatagacac atctt                                         25

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
gggtgtgtgg ccagatgttt                                               20

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
caccttccct gtggacttcc t                                             21

<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7
cagatcctca aacactctcc cataa                                         25

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
tgccttcttt gtcccatcat t                                            21

<210> SEQ ID NO 9
<211> LENGTH: 19
<212> TYPE: DNA
<213> ORGANISM: Artificial Sequence
<220> FEATURE:
<223> OTHER INFORMATION: Primer

<400> SEQUENCE: 9
atgacctggc tccacccat                                               19

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
tctttgaagc cattggtcag c                                            21

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
aggtccaggg tgaagaataa aagg                                         24

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
atctcaagtg tgcaaaagcc aga                                          23

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
cagggagaaa tatgcttgtc atca                                         24

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
gtgagcagat tggcccttac c                                            21

<210> SEQ ID NO 15
<211> LENGTH: 21
<212> TYPE: DNA

```
<213> ORGANISM: Artificial Sequence
<220> FEATURE:
<223> OTHER INFORMATION: Primer

<400> SEQUENCE: 15
aacgatggcc tgaatcactt g                                              21

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
agcctgaagt tctcaggatc c                                              21

<210> SEQ ID NO 17
<211> LENGTH: 30
<212> TYPE: DNA
<213> ORGANISM: Artificial Sequence
<220> FEATURE:
<223> OTHER INFORMATION: Primer

<400> SEQUENCE: 17
cttctctctc tcctctctct ttctctaatc                                     30

<210> SEQ ID NO 18
<211> LENGTH: 23
<212> TYPE: DNA
<213> ORGANISM: Artificial Sequence
<220> FEATURE:
<223> OTHER INFORMATION: Primer

<400> SEQUENCE: 18
aatgaactga gggaaaggaa agg                                            23

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
gccctggctc acaagtacca                                                20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
ttcacaggca agagcaggaa                                                20

<210> SEQ ID NO 21
<211> LENGTH: 27
<212> TYPE: DNA
<213> ORGANISM: Artificial Sequence
<220> FEATURE:
<223> OTHER INFORMATION: Primer

<400> SEQUENCE: 21
gtatgctcaa ttcaaatgta ccttatt                                        27
```

<210> SEQ ID NO 22
<211> LENGTH: 27
<212> TYPE: DNA
<213> ORGANISM: Artificial Sequence
<220> FEATURE:
<223> OTHER INFORMATION: Primer

<400> SEQUENCE: 22
ttacctcttt atttcacttt tacacat                                27

<210> SEQ ID NO 23
<211> LENGTH: 24
<212> TYPE: DNA
<213> ORGANISM: Artificial Sequence
<220> FEATURE:
<223> OTHER INFORMATION: Primer

<400> SEQUENCE: 23
gagccagcat tgggtatata aagc                                   24

<210> SEQ ID NO 24
<211> LENGTH: 26
<212> TYPE: DNA
<213> ORGANISM: Artificial Sequence
<220> FEATURE:
<223> OTHER INFORMATION: Primer

<400> SEQUENCE: 24
acagactcag aagcaaacgt aagaag                                 26

<210> SEQ ID NO 25
<211> LENGTH: 27
<212> TYPE: DNA
<213> ORGANISM: Artificial Sequence
<220> FEATURE:
<223> OTHER INFORMATION: Primer

<400> SEQUENCE: 25
tggccatttt tactatgtta attttgc                                27

<210> SEQ ID NO 26
<211> LENGTH: 25
<212> TYPE: DNA
<213> ORGANISM: Artificial Sequence
<220> FEATURE:
<223> OTHER INFORMATION: Primer

<400> SEQUENCE: 26
tagacttgtc atggttatgg attgg                                  25

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
ccagaacatt ccggcacatt                                        20

<210> SEQ ID NO 28
<211> LENGTH: 24
<212> TYPE: DNA
<213> ORGANISM: Artificial Sequence
<220> FEATURE:

<223> OTHER INFORMATION: Primer

<400> SEQUENCE: 28
ggtaagaggg acgtgttcaa cttt                                24

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29 caacccaga aacagacatc                                      20

<210> SEQ ID NO 30
<211> LENGTH: 18
<212> TYPE: DNA
<213> ORGANISM: Artificial Sequence
<220> FEATURE:
<223> OTHER INFORMATION: Primer

<400> SEQUENCE: 30
caacttcatc ggcgttca                                       18

<210> SEQ ID NO 31
<211> LENGTH: 21
<212> TYPE: DNA
<213> ORGANISM: Artificial Sequence
<220> FEATURE:
<223> OTHER INFORMATION: Primer

<400> SEQUENCE: 31
gcctgtgggg aaaggtgaac t                                   21

<210> SEQ ID NO 32
<211> LENGTH: 24
<212> TYPE: DNA
<213> ORGANISM: Artificial Sequence
<220> FEATURE:
<223> OTHER INFORMATION: Primer

<400> SEQUENCE: 32
ccatcgttaa aggcagttat cacc                                24

<210> SEQ ID NO 33
<211> LENGTH: 21
<212> TYPE: DNA
<213> ORGANISM: Artificial Sequence
<220> FEATURE:
<223> OTHER INFORMATION: Primer

<400> SEQUENCE: 33
gcctgtgggg aaaggtgaac g                                   21

<210> SEQ ID NO 34
<211> LENGTH: 25
<212> TYPE: DNA
<213> ORGANISM: Artificial Sequence
<220> FEATURE:
<223> OTHER INFORMATION: Primer

<400> SEQUENCE: 34
gccatcgtta aggcagtta tcact                                25

```
<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
agctccactg tgacaagctg                                              20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
ccagcacaat cacgatcata                                              20

<210> SEQ ID NO 37
<211> LENGTH: 22
<212> TYPE: DNA
<213> ORGANISM: Artificial Sequence
<220> FEATURE:
<223> OTHER INFORMATION: Primer

<400> SEQUENCE: 37
aggcagctat cacaagcatc tg                                           22

<210> SEQ ID NO 38
<211> LENGTH: 26
<212> TYPE: DNA
<213> ORGANISM: Artificial Sequence
<220> FEATURE:
<223> OTHER INFORMATION: Primer

<400> SEQUENCE: 38
aacttgtcaa agaatctctg agtcca                                       26

<210> SEQ ID NO 39
<211> LENGTH: 21
<212> TYPE: DNA
<213> ORGANISM: Artificial Sequence
<220> FEATURE:
<223> OTHER INFORMATION: Primer

<400> SEQUENCE: 39
gtggatcccg tcaacttcaa g                                            21

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
caaggtcacc agcaggcagt                                              20

<210> SEQ ID NO 41
<211> LENGTH: 20
<212> TYPE: DNA
<213> ORGANISM: Artificial Sequence
<220> FEATURE:
<223> OTHER INFORMATION: Primer
```

<400> SEQUENCE: 41
tggaggcctg atccgtgata                                              20

<210> SEQ ID NO 42
<211> LENGTH: 18
<212> TYPE: DNA
<213> ORGANISM: Artificial Sequence
<220> FEATURE:
<223> OTHER INFORMATION: Primer

<400> SEQUENCE: 42
agcgcatcgg tgatgtca                                                18

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
ccatcttaag gcaaccaagg c                                            21

<210> SEQ ID NO 44
<211> LENGTH: 21
<212> TYPE: DNA
<213> ORGANISM: Artificial Sequence
<220> FEATURE:
<223> OTHER INFORMATION: Primer

<400> SEQUENCE: 44
acagcatgaa aggacaatgg c                                            21

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
ttccggagag gacgatgaga                                              20

<210> SEQ ID NO 46
<211> LENGTH: 26
<212> TYPE: DNA
<213> ORGANISM: Artificial Sequence
<220> FEATURE:
<223> OTHER INFORMATION: Primer

<400> SEQUENCE: 46
aacctggaaa gtttgtaagg aaaaga                                       26

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
gcccaagaag cgaatgattg                                              20

<210> SEQ ID NO 48
<211> LENGTH: 24

```
<212> TYPE: DNA
<213> ORGANISM: Artificial Sequence
<220> FEATURE:
<223> OTHER INFORMATION: Primer

<400> SEQUENCE: 48
gtggtcgttt gacagttagt gcat                                         24

<210> SEQ ID NO 49
<211> LENGTH: 21
<212> TYPE: DNA
<213> ORGANISM: Artificial Sequence
<220> FEATURE:
<223> OTHER INFORMATION: Primer

<400> SEQUENCE: 49
cacccctaag cagagaagca a                                            21

<210> SEQ ID NO 50
<211> LENGTH: 21
<212> TYPE: DNA
<213> ORGANISM: Artificial Sequence
<220> FEATURE:
<223> OTHER INFORMATION: Primer

<400> SEQUENCE: 50
tggcaccaca gttgacacac t                                            21

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
agcagatctc ggacagcacc                                              20

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
tgcagtttgc caagttggag                                              20

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
gatgccccca tgtttgtgat                                              20

<210> SEQ ID NO 54
<211> LENGTH: 21
<212> TYPE: DNA
<213> ORGANISM: Artificial Sequence
<220> FEATURE:
<223> OTHER INFORMATION: Primer

<400> SEQUENCE: 54
```

-continued ggtcatgagc ccttccacaa t                                                    21

<210> SEQ ID NO 55
<211> LENGTH: 17
<212> TYPE: DNA
<213> ORGANISM: Artificial Sequence
<220> FEATURE:
<223> OTHER INFORMATION: Primer

<400> SEQUENCE: 55
acacccgcca ccagttc                                                         17

<210> SEQ ID NO 56
<211> LENGTH: 17
<212> TYPE: DNA
<213> ORGANISM: Artificial Sequence
<220> FEATURE:
<223> OTHER INFORMATION: Primer

<400> SEQUENCE: 56
tacagcccgg ggagcat                                                         17

<210> SEQ ID NO 57
<211> LENGTH: 22
<212> TYPE: DNA
<213> ORGANISM: Artificial Sequence
<220> FEATURE:
<223> OTHER INFORMATION: Probe

<400> SEQUENCE: 57
tctgcctgtc cctgcctcgt ga                                                   22

<210> SEQ ID NO 58
<211> LENGTH: 27
<212> TYPE: DNA
<213> ORGANISM: Artificial Sequence
<220> FEATURE:
<223> OTHER INFORMATION: Primer

<400> SEQUENCE: 58
cagcgtttta gttggatata gagtgaa                                              27

<210> SEQ ID NO 59
<211> LENGTH: 28
<212> TYPE: DNA
<213> ORGANISM: Artificial Sequence
<220> FEATURE:
<223> OTHER INFORMATION: Primer

<400> SEQUENCE: 59
gaacttgtca gggaattacc tagtacag                                             28

<210> SEQ ID NO 60
<211> LENGTH: 25
<212> TYPE: DNA
<213> ORGANISM: Artificial Sequence
<220> FEATURE:
<223> OTHER INFORMATION: Primer

<400> SEQUENCE: 60
gatccctatt gtctactttt gccag                                                25

<210> SEQ ID NO 61
<211> LENGTH: 23
<212> TYPE: DNA
<213> ORGANISM: Artificial Sequence

```
<220> FEATURE:
<223> OTHER INFORMATION: Primer

<400> SEQUENCE: 61
cccatgttac accccattac aag                                         23

<210> SEQ ID NO 62
<211> LENGTH: 24
<212> TYPE: DNA
<213> ORGANISM: Artificial Sequence
<220> FEATURE:
<223> OTHER INFORMATION: Primer

<400> SEQUENCE: 62
ggctggaaca tcactggaat aaat                                        24

<210> SEQ ID NO 63
<211> LENGTH: 22
<212> TYPE: DNA
<213> ORGANISM: Artificial Sequence
<220> FEATURE:
<223> OTHER INFORMATION: Primer

<400> SEQUENCE: 63
cagtcgagga atgcaactgt ga                                          22

<210> SEQ ID NO 64
<211> LENGTH: 26
<212> TYPE: DNA
<213> ORGANISM: Artificial Sequence
<220> FEATURE:
<223> OTHER INFORMATION: Primer

<400> SEQUENCE: 64
aagactaaaa atcccagatt gattcc                                      26

<210> SEQ ID NO 65
<211> LENGTH: 22
<212> TYPE: DNA
<213> ORGANISM: Artificial Sequence
<220> FEATURE:
<223> OTHER INFORMATION: Primer

<400> SEQUENCE: 65
gccaaatcag gaccctaaca tt                                          22

<210> SEQ ID NO 66
<211> LENGTH: 25
<212> TYPE: DNA
<213> ORGANISM: Artificial Sequence
<220> FEATURE:
<223> OTHER INFORMATION: Primer

<400> SEQUENCE: 66
ccaagtctct caagaaagaa atcga                                       25

<210> SEQ ID NO 67
<211> LENGTH: 27
<212> TYPE: DNA
<213> ORGANISM: Artificial Sequence
<220> FEATURE:
<223> OTHER INFORMATION: Primer

<400> SEQUENCE: 67
caaacataag accataagca acagaaa                                     27
```

<210> SEQ ID NO 68
<211> LENGTH: 28
<212> TYPE: DNA
<213> ORGANISM: Artificial Sequence
<220> FEATURE:
<223> OTHER INFORMATION: Primer

<400> SEQUENCE: 68
actacctaac tctcaaaaat ctgtgtga                                    28

<210> SEQ ID NO 69
<211> LENGTH: 29
<212> TYPE: DNA
<213> ORGANISM: Artificial Sequence
<220> FEATURE:
<223> OTHER INFORMATION: Primer

<400> SEQUENCE: 69
gaaaaaatgt gtacgcatca ttagttatg                                   29

<210> SEQ ID NO 70
<211> LENGTH: 30
<212> TYPE: DNA
<213> ORGANISM: Artificial Sequence
<220> FEATURE:
<223> OTHER INFORMATION: Probe

<400> SEQUENCE: 70
tctagagcca aactctccag ccaccacttc                                  30

<210> SEQ ID NO 71
<211> LENGTH: 28
<212> TYPE: DNA
<213> ORGANISM: Artificial Sequence
<220> FEATURE:
<223> OTHER INFORMATION: Primer

<400> SEQUENCE: 71
gcagtgaaaa cacaacacag ttaatatg                                    28

<210> SEQ ID NO 72
<211> LENGTH: 18
<212> TYPE: DNA
<213> ORGANISM: Artificial Sequence
<220> FEATURE:
<223> OTHER INFORMATION: Primer

<400> SEQUENCE: 72
gcagccaccg acttggat                                               18

<210> SEQ ID NO 73
<211> LENGTH: 23
<212> TYPE: DNA
<213> ORGANISM: Artificial Sequence
<220> FEATURE:
<223> OTHER INFORMATION: Primer

<400> SEQUENCE: 73
tgtagatcag gattgactgg tac                                         23

<210> SEQ ID NO 74
<211> LENGTH: 27
<212> TYPE: DNA
<213> ORGANISM: Artificial Sequence
<220> FEATURE:
<223> OTHER INFORMATION: Primer

<400> SEQUENCE: 74
cagcgtttta gttggatata gagtgaa                                          27

<210> SEQ ID NO 75
<211> LENGTH: 20
<212> TYPE: DNA
<213> ORGANISM: Artificial Sequence
<220> FEATURE:
<223> OTHER INFORMATION: Primer

<400> SEQUENCE: 75
gggtgtgtgg ccagatgttt                                                 20

<210> SEQ ID NO 76
<211> LENGTH: 21
<212> TYPE: DNA
<213> ORGANISM: Artificial Sequence
<220> FEATURE:
<223> OTHER INFORMATION: Primer

<400> SEQUENCE: 76
caccttccct gtggacttcc t                                               21

<210> SEQ ID NO 77
<211> LENGTH: 27
<212> TYPE: DNA
<213> ORGANISM: Artificial Sequence
<220> FEATURE:
<223> OTHER INFORMATION: Primer

<400> SEQUENCE: 77
gcgttttagt tggatataga gtgaagg                                         27

<210> SEQ ID NO 78
<211> LENGTH: 29
<212> TYPE: DNA
<213> ORGANISM: Artificial Sequence
<220> FEATURE:
<223> OTHER INFORMATION: Primer

<400> SEQUENCE: 78
tgctatcatg gaacatacta tgtagatca                                       29

<210> SEQ ID NO 79
<211> LENGTH: 20
<212> TYPE: DNA
<213> ORGANISM: Artificial Sequence
<220> FEATURE:
<223> OTHER INFORMATION: Primer

<400> SEQUENCE: 79
aggaacaggc aaggcagctt                                                 20

<210> SEQ ID NO 80
<211> LENGTH: 25
<212> TYPE: DNA
<213> ORGANISM: Artificial Sequence
<220> FEATURE:
<223> OTHER INFORMATION: Primer

<400> SEQUENCE: 80
tcactggtac cctgttttcct tatct                                          25

<210> SEQ ID NO 81

```
<211> LENGTH: 28
<212> TYPE: DNA
<213> ORGANISM: Artificial Sequence
<220> FEATURE:
<223> OTHER INFORMATION: HS2 target DNA

<400> SEQUENCE: 81
taccactgtc caagggcaga ggaggtta                                              28

<210> SEQ ID NO 82
<211> LENGTH: 28
<212> TYPE: DNA
<213> ORGANISM: Artificial Sequence
<220> FEATURE:
<223> OTHER INFORMATION: Bmaj promoter target DNA

<400> SEQUENCE: 82
actcactggc ttaggagtct cagctctg                                              28

<210> SEQ ID NO 83
<211> LENGTH: 7
<212> TYPE: PRT
<213> ORGANISM: Artificial Sequence
<220> FEATURE:
<223> OTHER INFORMATION: pol II peptide

<400> SEQUENCE: 83

Tyr Ser Pro Thr Ser Pro Ser
1               5
```